(12) United States Patent
Morris et al.

(10) Patent No.: US 9,918,849 B2
(45) Date of Patent: Mar. 20, 2018

(54) COILED IMPLANTS AND SYSTEMS AND METHODS OF USE THEREOF

(71) Applicant: Institute for Musculoskeletal Science and Education, Ltd., Wayne, PA (US)

(72) Inventors: Robert Morris, Gwynedd Valley, PA (US); William Duffield, Collegeville, PA (US); Edward McShane, Collegeville, PA (US); Megan Stauffer, Wayne, PA (US)

(73) Assignee: INSTITUTE FOR MUSCULOSKELETAL SCIENCE AND EDUCATION, LTD., Wayne, PA (US)

( * ) Notice: Subject to any disclaimer, the term of this patent is extended or adjusted under 35 U.S.C. 154(b) by 0 days.

(21) Appl. No.: 15/141,655

(22) Filed: Apr. 28, 2016

(65) Prior Publication Data

US 2016/0324656 A1 Nov. 10, 2016

Related U.S. Application Data

(60) Provisional application No. 62/301,546, filed on Feb. 29, 2016, provisional application No. 62/217,542, (Continued)

(51) Int. Cl.
*A61F 2/44* (2006.01)
*A61F 2/30* (2006.01)

(52) U.S. Cl.
CPC ........ *A61F 2/4455* (2013.01); *A61F 2/30744* (2013.01); *A61F 2002/30011* (2013.01); (Continued)

(58) Field of Classification Search
CPC ............... A61F 2/4455; A61F 2/30744; A61F 2002/30011; A61F 2002/30013;
(Continued)

(56) References Cited

U.S. PATENT DOCUMENTS 4,917,704 A * 4/1990 Frey .................. A61F 2/442
606/247
5,716,416 A 2/1998 Lin
(Continued)

FOREIGN PATENT DOCUMENTS

WO 2009051779 4/2009
WO 2010097632 9/2010
(Continued)

OTHER PUBLICATIONS

International Search Report and Written Opinion for PCT application PCT/US2016/029865 dated Aug. 19, 2016.
(Continued)

*Primary Examiner* — Pedro Philogene
*Assistant Examiner* — David C Comstock
(74) *Attorney, Agent, or Firm* — Plumsea Law Group, LLC

(57) ABSTRACT

Implants, systems and methods of making and using thereof are described herein. The implants are formed from one or more coils, preferably a plurality of coils. Optionally the coils are included in a set or group of more than one coil. Optionally, the implant is symmetric about one or more planes. Typically an implant includes at least two coils (or sets or groups of coils) that are adjacent to each other intersect with each other at one or more intersection regions. Two or more coils may intersect at a plurality of intersection regions, optionally along an array of intersection regions, within the implant or on the outer side wall of the implant. Optionally, the implants include one or more plates to aid in fixation and/or insertion. The implants may be used in a variety of different spaces in the body that require bone growth.

35 Claims, 35 Drawing Sheets

Related U.S. Application Data filed on Sep. 11, 2015, provisional application No. 62/154,599, filed on Apr. 29, 2015.

(52) U.S. Cl.
CPC .............. *A61F 2002/30013* (2013.01); *A61F 2002/3092* (2013.01); *A61F 2002/30289* (2013.01); *A61F 2002/30311* (2013.01); *A61F 2002/30622* (2013.01); *A61F 2002/30772* (2013.01); *A61F 2002/30774* (2013.01); *A61F 2002/30957* (2013.01); *A61F 2002/30985* (2013.01); *A61F 2002/4475* (2013.01); *A61F 2002/4495* (2013.01)

(58) Field of Classification Search
CPC .. A61F 2002/30289; A61F 2002/30311; A61F 2002/30622; A61F 2002/30772; A61F 2002/30774; A61F 2002/3092; A61F 2002/30957; A61F 2002/30985; A61F 2002/4475; A61F 2002/4495
USPC .......................................... 623/17.11–17.16
See application file for complete search history.

(56) References Cited

U.S. PATENT DOCUMENTS

| | | | |
|---|---|---|---|
| 6,206,924 B1 | 3/2001 | Timm | |
| 6,296,656 B1 | 10/2001 | Bolduc et al. | |
| 6,520,996 B1 | 2/2003 | Manasas | |
| 6,689,168 B2 | 2/2004 | Lieberman | |
| 7,261,739 B2 | 8/2007 | Ralph et al. | |
| 7,297,162 B2 | 11/2007 | Mujwid | |
| 7,485,134 B2 | 2/2009 | Simonson | |
| 7,621,952 B2 | 11/2009 | Truckai | |
| 7,628,814 B2 | 12/2009 | Studer | |
| 7,799,056 B2 | 9/2010 | Sankaran | |
| 7,879,100 B2* | 2/2011 | Denoziere | A61F 2/3094 623/17.11 |
| 7,879,103 B2 | 2/2011 | Gertzman | |
| 8,021,426 B2 | 9/2011 | Segal | |
| 8,092,536 B2 | 1/2012 | Ahrens | |
| 8,298,286 B2 | 10/2012 | Trieu | |
| 8,328,848 B2 | 12/2012 | Lowery | |
| 8,430,930 B2 | 4/2013 | Hunt | |
| 8,556,978 B2 | 10/2013 | Schaller | |
| 8,728,160 B2 | 5/2014 | Globerman et al. | |
| 8,740,981 B2 | 6/2014 | Tornier | |
| 8,771,368 B2 | 7/2014 | McKay | |
| 8,795,362 B2 | 8/2014 | Anderson | |
| 8,801,787 B2 | 8/2014 | Schaller | |
| 8,808,376 B2 | 8/2014 | Schaller | |
| 8,808,725 B2 | 8/2014 | Altschuler | |
| 8,900,310 B2 | 12/2014 | Carlson et al. | |
| 8,951,300 B2 | 2/2015 | Parrish | |
| 9,173,746 B2 | 11/2015 | Lowery | |
| 9,271,845 B2 | 3/2016 | Hunt | |
| 9,295,562 B2 | 3/2016 | Lechmann | |
| 9,421,108 B2 | 8/2016 | Hunt | |
| 2002/0123750 A1* | 9/2002 | Eisermann | A61B 17/68 606/285 |
| 2002/0177898 A1 | 11/2002 | Crozet | |
| 2003/0078660 A1 | 4/2003 | Clifford | |
| 2004/0225361 A1 | 11/2004 | Glenn | |
| 2006/0041262 A1 | 2/2006 | Calvert | |
| 2006/0052872 A1 | 3/2006 | Studer | |
| 2006/0052873 A1* | 3/2006 | Buck | A61F 2/442 623/17.16 |
| 2006/0058881 A1* | 3/2006 | Trieu | A61F 2/442 623/17.16 |
| 2006/0212118 A1 | 9/2006 | Abernathie | |
| 2006/0293753 A1 | 12/2006 | Thramann | |
| 2008/0306595 A1 | 12/2008 | McLeod | |
| 2009/0048678 A1 | 2/2009 | Saal | |
| 2009/0112321 A1 | 4/2009 | Kitchen | |
| 2009/0149958 A1 | 6/2009 | Prewett | |
| 2010/0137990 A1* | 6/2010 | Apatsidis | A61L 27/56 623/17.16 |
| 2011/0066192 A1 | 3/2011 | Frasier | |
| 2011/0166660 A1 | 7/2011 | Laurence | |
| 2011/0190895 A1 | 8/2011 | Segal | |
| 2011/0245926 A1 | 10/2011 | Kitchen | |
| 2011/0270401 A1 | 11/2011 | McKay | |
| 2011/0313532 A1 | 12/2011 | Hunt | |
| 2012/0296431 A1 | 11/2012 | Kim | |
| 2013/0030529 A1 | 1/2013 | Hunt | |
| 2013/0123935 A1 | 5/2013 | Hunt | |
| 2013/0158672 A1 | 6/2013 | Hunt | |
| 2013/0190880 A1 | 7/2013 | Schaller | |
| 2013/0218282 A1 | 8/2013 | Hunt | |
| 2013/0218288 A1 | 8/2013 | Fonte | |
| 2013/0304211 A1 | 11/2013 | Trautwein | |
| 2014/0052260 A1 | 2/2014 | McKenny et al. | |
| 2014/0058513 A1 | 2/2014 | Gahman | |
| 2014/0114418 A1 | 4/2014 | Landry et al. | |
| 2014/0121776 A1 | 5/2014 | Hunt | |
| 2014/0142707 A1 | 5/2014 | Compton | |
| 2014/0195005 A1 | 7/2014 | McKay | |
| 2014/0243980 A1 | 8/2014 | Sack | |
| 2014/0277457 A1 | 9/2014 | Yeung | |
| 2014/0277464 A1 | 9/2014 | Richter | |
| 2014/0277569 A1 | 9/2014 | Lange | |
| 2014/0288649 A1 | 9/2014 | Hunt | |
| 2014/0288650 A1 | 9/2014 | Hunt | |
| 2014/0303745 A1 | 10/2014 | Anderson | |
| 2014/0309743 A1 | 10/2014 | Falahee | |
| 2014/0358246 A1 | 12/2014 | Levy | |
| 2015/0282933 A1 | 10/2015 | Hunt | |
| 2015/0282945 A1 | 10/2015 | Hunt | |
| 2015/0282946 A1 | 10/2015 | Hunt | |
| 2016/0045230 A1 | 2/2016 | Lowery | |
| 2017/0042697 A1 | 2/2017 | McShane et al. | |
| 2017/0156879 A1 | 6/2017 | Janowski | |

FOREIGN PATENT DOCUMENTS

| | | |
|---|---|---|
| WO | 2011159587 | 12/2011 |
| WO | 2013019543 | 2/2013 |

OTHER PUBLICATIONS

International Search Report and Written Opinion dated Jan. 18, 2018 for International Patent Application No. PCT/US2017/58100.
"FDA Clears Camber Spine Technologies; 3D Printed SPIRA Open Matrix ALIF", Orthopedic Design & Technology, Aug. 15, 2017, https://www.odtmag.comjcontents/view_breaking-news/2017-08-IS/fda-dears-camber-spine-technologies-3d-printed-spira-ope. Last accessed Dec. 15, 2017.

\* cited by examiner

COILED IMPLANTS AND SYSTEMS AND METHODS OF USE THEREOF

CROSS REFERENCE TO RELATED APPLICATIONS

The present application claims priority to U.S. Application No. 62/154,599, filed on Apr. 29, 2015; U.S. Application No. 62/217,542, filed on Sep. 11, 2015; and U.S. Application No. 62/301,546, filed on Feb. 29, 2016, the disclosures of which is incorporated herein by reference in their entirety.

FIELD OF THE INVENTION

The invention is generally directed to implants for supporting bone growth in a patient.

BACKGROUND OF THE INVENTION

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. A device, the spinal fusion cage, may be placed between the vertebra to maintain spine alignment and disc height. The fusion, i.e. bone bridge, occurs between the endplates of the vertebrae.

However, providing space within the implant for the bone ingrowth can compromise the strength and stability of the implant.

There is a need for improved implants that maintain their shape under pressure and tension, and provide sufficient openings for bone ingrowth.

An object of the present invention is to provide improved implants.

It is a further object of the present invention to provide systems for repairing bone or creating a bone fusion in a patient.

It is a still further object of the present invention to provide methods of manufacturing such implants.

SUMMARY OF THE INVENTION

Implants, systems and methods of making and using such implants are described herein. The implants are formed from one or more coils, preferably a plurality of coils. In some embodiments, the walls of the implant are formed from a plurality of coils, optionally the coils are included in a set or group of more than one coil.

The coils in each set of coils are aligned such that they do not contact each other. However, typically an implant includes at least two coils (or sets or groups of coils) that are adjacent to each other intersect with each other at one or more intersection regions, typically at regular intervals. The coils may intersect at a plurality of intersection regions, optionally along an array of intersection regions. The intersection regions are generally not located on the superior or inferior surfaces of the implant, which contact an adjacent superior or inferior bony surface. Rather, the intersection regions are generally located in the inside of the implant and/or the side walls of the implant.

Optionally, the implants include one or more plates to aid in fixation and/or insertion. In some embodiments, the implant contains a plate in place of one of the side walls. In other embodiments, the one or more plates are attached to and integral with a side wall or corner of an implant. In these embodiments, the plate is only in a portion of the wall. The plate may include one or more regions into which an insertion tool fits. Alternatively or additionally, the plate may include one or more holes for bone screws or other fixation devices. The plates are preferably integral with the cage. For example, the plate(s) and cage can be fabricated in one process using 3-D printing. Optionally, the plates are fabricated separately, and configured for attachment to the cages.

The systems contain one or more implants, optionally with one or more fixation elements. Optionally, the system includes a bone graft or bone graft substitute inside the implant.

The implants can be configured to be used in a variety of different spaces in the body that require bone growth to repair the site. In one embodiment, the implants are configured for use in the spine, such as in spinal fusion. In another embodiment, the implants are configured for use in a joint. Optionally, the implants are configured for use in the ankle or foot, such as to repair a fracture in this region. Alternatively, the implant can be configured for other sites in the body, such as for use in or adjacent to a large joint (e.g., a hip and/or knee implant), a small joint (e.g., shoulder, elbow and/or ankle implants), at a site of trauma (e.g., shoulder fracture, long bone reconstruction implants and/or intermedullary rod/nail implants), craniomaxillofacial (e.g., implant for use in jaw replacement, or cranial reconstruction), or in the mouth (e.g. dental implants).

BRIEF DESCRIPTION OF THE DRAWINGS

FIG. 3A is a side elevation view. FIG. 3B is a front axial view.

FIG. 4A is a side elevation view. FIG. 4B is a front axial view.

FIG. 5A is a side elevation view. FIG.

5B is a top plan view. FIG. 5C is a side view. FIG. 5D is a magnified view of a portion of the outer wall of the implant depicted in FIG. 5C.

FIG. 6A is a top plan view. FIG. 6B is a side elevation view. FIG. 6C is a side view (the opposite side is substantially a mirror image). FIG. 6D is another side view taken from a side that is adjacent to the front portion of the side depicted in FIG. 6C (the opposite side is substantially a mirror image). FIG. 6C depicts one side of a bi-convex implant, and FIG. 6D depicts the adjacent side.

FIG. 7A is a side elevation view. FIG. 7B is a side view, showing the convexity of the implant, where one surface is convex and the opposite surface is concave.

FIG. 8A is a side elevation view. FIG. 8B is a side view, showing the convexity of the level. FIG. 8C is a side view, of another side of the level showing the bi-convexity of the level. FIG. 8D is a top plan view.

FIG. 9A is a side elevation view. FIG. 9B is a top plan view. FIG. 9C is a front view of the implant. FIG. 9D is a cross-sectional view of the implant taken about the line A-A in FIG. 9C.

FIG. 10A is a side elevation view. FIG. 10B is a side elevation view of the implant. FIG. 10C is a top plan view. FIG. 10D is a side view of the implant at the corner between the two plates.

FIG. 11A is a plan view, FIG. 11B is a posterior end view, FIG. 11C is an isometric view, FIG. 11D is an anterior end view, and FIG. 11E is a side elevation view, of the implant.

FIG. 12A is a plan view, FIG. 12B is a posterior end view, FIG. 12C is an isometric view. FIG. 12D is an anterior end view, and FIG. 12E is a side view of the implant.

FIG. 13A is a plan view, and FIG. 13B is a side view.

FIG. 14A is a top view, FIG. 14B is a side elevation view, FIG. 14C is a posterior end view, FIG. 14D is an anterior end view, FIG. 14E is a top posterior perspective view showing one quarter of the implant, where the implant is cut along both the median plane M and the transverse plane T. FIG. 14F is a bottom perspective view of the same portion of the implant illustrated in FIG. 14E. FIG. 14G is one top perspective view of the implant taken from one side relative to the median plane M. FIG. 14H is another top perspective view of the implant taken from the opposite side relative to the median plane M. FIG. 14I is a partial view of the implant, showing the central support portion attached to the anterior and posterior ends of the implant.

FIG. 15A is a top view, and FIG. 15B is a top posterior perspective view showing one quarter of the implant, where the implant is cut along both the median plane M and the transverse plane T. FIG. 15C is a partial view of the implant, showing the central support portion attached to the anterior and posterior ends of the implant.

FIG. 16A shows a 3-D printing method using an electron beam melting (EBM) method. FIG. 16B shows a 3-D printing method using a direct metal laser sintering (DMLS) method.

DETAILED DESCRIPTION OF THE INVENTION

Figure 1:
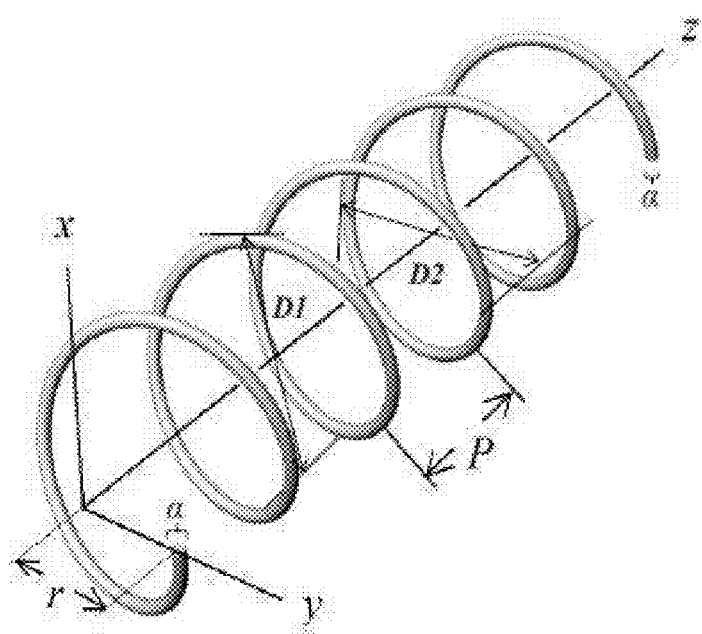
FIG. 1 is an illustration of an exemplary single helical coil with the helical axis (z), the largest diameter of the coil, also referred to as its major diameter (D1), the smallest diameter of the coil, also referred to as its minor diameter (D2), pitch (P), largest dimension of the cross section of the coil (U), and length (I) labeled thereon. When the coil is in the form of a circle, D1=D2 and is referred to herein as "D". When the material that forms the coil has a cross section of a circle, the largest dimension of the cross section of the coil ($\alpha$) is its diameter, which is referred to herein as "d".

I. Implants
  A. Structure

The implant is configured to provide sufficient open space within the implant for bone growth, while providing sufficient strength and stability, even when under high compressive forces in the body.

The implants are formed from one or more coils, typically from a plurality of coils. Preferably the coils in the implant are oriented with respect to each other in a sufficient amount and packing density to provide sufficient structural support so that the implant resists deflection under a constant load over time, such as when subjected to the standard loads applied to the human spine. Preferably the implant resists deflection when subjected to higher loads, such as loads of up to about 630-940 lb$_f$, which generally corresponds with the compressive breaking point for cervical spine, or even higher loads, such as loads of up to about 8 kN (1,800 lb$_f$), which generally corresponds with the compressive strength of a single vertebral body and with the compressive breaking point for lumbar spine.

The implant can have any suitable shape and size for the particular site in which it will be used. For implants used in the cervical spine, widths for the implant in the coronal plane range from approximately 10 mm to 22 mm; dimensions for the implant in the sagittal plane range from approximately 8 mm to 16 mm; and heights for the implant range from about 5 mm to 40 mm. For implants used in the thoracic spine, widths for the implant in the coronal plane range from approximately 23 mm to 34 mm; dimensions for the implant in the sagittal plane range from approximately 16 mm to 27 mm; and heights for the implant range from about 6 mm to 53 mm. For implants used in the lumbar spine, widths for the implant in the coronal plane range from approximately 24 mm to 46 mm; dimensions for the implant in the sagittal plane range from approximately 20 mm to 40 mm; and heights for the implant range from about 6 mm to 60 mm.

For implants used in other parts of the body, such as for use in a large joint (e.g., a hip and/or knee implant), a small joint (e.g., shoulder, elbow and/or ankle implants), at a site of trauma (e.g., shoulder fracture, long bone reconstruction implants and/or intermedullary rod/nail implants), craniomaxillofacial (e.g., implant for use in jaw replacement, or cranium reconstruction), or in the mouth (e.g. dental implants), typical dimensions generally correspond with current implants used in these sites.

The implant may be symmetrical about one or more planes. As used herein, the term "median plane" refers to a vertical plane which passes from the anterior end to the posterior end of the implant, dividing the implant into right and left halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the median and the transverse plane.

Optionally, one or more portions of the implant contain a textured or porous surface to increase friction against bone surfaces, and/or promote growth of bone graft. In some embodiments, the superior and inferior surfaces, any interior surfaces including on the supports and the interior walls may be 3D printed with textured or porous surfaces. In further embodiments, the entire implant is 3D printed with a textured or porous surface, optionally, with the exception of the exterior surfaces of the peripheral ring which contains the anterior plate, the posterior plate and/or the side wall(s).

1. Coil(s)

The implant contains one or more coils. Typically the implant contains a plurality of coils. For example, two or more, optionally all of the coils may have the same dimensions (e.g. major and minor diameters of the coil (D1 and D2), pitch (p), largest dimension of the cross section of the coil ($\alpha$), and length (l), see FIG. 1). In other embodiments, the coils in the implant may have different dimensions. In some embodiments, one or more smaller diameter coils are located inside and surrounded by one or more larger coils in the implant.

In yet other embodiments, one or more of the dimensions in a given coil may vary, for example, the major and/or minor diameters (D1 and D2) of the coil may vary over the length of the coil. In one embodiment, where the coil is a circular helical coil and D1=D2 (referred to herein as D), the diameter (D) tapers with the greatest diameter in the center of the coil and the smallest diameters on each of the ends of the coil. In another embodiment, the diameter of the coil tapers, with the greatest diameter (D) for one or more coils in the implant at the anterior end of the implant and the smallest diameter at the posterior end of the implant. In still other embodiments, the greatest diameter for one or more coils in the implant is at the posterior end of the implant and the smallest diameter is at the anterior end of the implant. In still other embodiments, the greatest diameter (D) of the coil may be located near one end of the implant, but not be located precisely at the end of the implant. For example, the greatest diameter (D) of the coils may be located between the center of the implant and the anterior end of the implant in an interbody fusion spacer, such as an ALIF, with the diameter decreasing from this region until the coils reach the anterior and posterior ends. In this embodiment, the anterior end has a greater diameter (D) than the posterior end.

Further the pitch may vary over the length of the coil, for example at each of the ends, the coil may be tightly wound so that each of the turns touches the proximal turn.

One or more coils, sets of coils or groups of coils in an implant may contain one or more flat portions, typically corresponding to the portion of the coil that is located in the inferior or superior surface of the implant. The outer surface of one or more coils may be configured to conform to the shape of the adjacent bony surface when the implant is implanted in a patient's body.

Typical lengths for the coils depend on the size of the implant and location of the coil within the implant. For example, a coil that winds around multiple times to form the implant can be quite long. Lengths can range from 5 mm to 100 mm. However, coils with shorter or longer lengths may be used to form the implant.

The largest dimension of the cross section of the material that forms the coils ($\alpha$) in the implant can be the same for each coil or set or group of coils or vary between coils or sets or groups of coils. Further different coils may have different cross-sectional geometries or the same cross-sectional geometries.

The diameter (d) of the material that forms the coils in the implant can be the same for each coil or set or group of coils or vary between coils or sets or groups of coils. In some embodiments, the material that forms the coils in the sets of exterior coils has a greater diameter ($d_{ec}$) than the diameter of the material that forms the coils in the sets of interior coils ($d_{ic}$). In other embodiments, the material that forms the coils in the sets of exterior coils a smaller diameter ($d_{ec}$) than the diameter of the material that forms the coils in the sets of interior coils ($d_{ic}$). In still other embodiments, $d_{ec}$ and $d_{ic}$ are equal. Preferably the material that forms the coils in the sets of exterior coils has a diameter ($d_{ec}$) that is greater than or equal to the diameter of the material that forms the coils in the sets of interior coils ($d_{ic}$) ($d_{ec} \leq d_{ic}$), more preferably $d_{ec}$ is greater than $d_{ic}$.

Typically the diameter of the material (d) that forms the coil ranges from about 0.25 mm to about 5 mm, preferably from 1 mm to 3 mm.

Typical pitches range from about 2 to about 30 mm.

Suitable diameters (D) for the coils that are used to form the implant are typically at least 0.7 mm, optionally at least 1 mm or at least 2 mm in diameter. However, other diameters and ranges thereof are also envisioned. In some embodiments, the diameter of the coil (D) ranges from about 1 mm to about 13 mm. In some embodiments, the diameter of the coil (D) varies along the length of the coil. Optionally the diameter (D) changes incrementally over the length of the coil from a greatest diameter at one end to a smallest diameter at an opposite end. For example, at one end, the coil may have a diameter (D) of about 1 mm, and at the opposite end the coil may have a diameter (D) of about 13 mm, with the diameter increasing from the first end to the second end over the length of the coil to increase contact with the surrounding/adjacent bony anatomy.

The coils can be in any form, such as continuous closed loops, which do not contain an end, or coils with at least a first end and a second end (also referred to herein as "coiled segments"). The term "exterior coil(s)" refers to a coil, group of coils or set of coils positioned on the outermost position of the implant relative to the center of the implant. The term "interior coil(s)" refers to any coil, group of coils or set of coils positioned closest/closer to the center of the implant, including those located or intersecting with the center of the implant relative to the exterior coils.

The term "coiled segment" refers to a segment of any geometrical shape formed of one or more coils, preferably two or more congruent coils in a set of coils, or two or more coils in a group of coils. Suitable geometric shapes include, but are not limited to circle, oval, lines, and irregular shapes, typically including one or more curved portions, optionally including a combination or one or more curved portions and one or more straight portions. The term "coiled segments" includes interrupted loops. i.e. otherwise continuous loops that intersect with a plate or peripheral ring or an adjacent coil or set or group of coils. Each coiled segment has at least a first end and a second end. The term "exterior coiled segment" refers to a coiled segment positioned on the outermost position of the implant relative to the center of the implant. The term "interior coiled segment" refers to any coiled segment positioned closest/closer to the center of the implant relative to the exterior coiled segment.

Coiled segments that are in the form of an arc are often referred to herein, as "coiled arcs". The arc may represent any part of the circumference of any circle, on any part of any curve. The coiled are typically has a first end and a second end. The first end and the second end of the coiled arc may be positioned along any part of the circumference of any circle, on any part of any curve. The curve may be concave or convex. The term "exterior coiled arc" refers to a coiled arc positioned on the outermost position of an implant relative to the center of the implant. The term "interior coiled arc" refers to a coiled are positioned closest to center of the implant. The term "intermediate coiled arc" refers to any coiled arc positioned between the interior coiled arc and the exterior coiled arc.

In some embodiments, the implant contains a plurality of coils that are stacked on top of each other to define the outer lateral surfaces, i.e. walls, of the implant. For example, each of the coils that forms the outer walls may be in the form of a continuous closed loop. In some embodiments, one or more optionally all, of the coils that form the outer walls of the implant are coiled segments, such as interrupted loops, and are attached at two or more ends to a plate or more than one plate. The inside of the implant may also be filled with a plurality of coils, which are stacked on top of each other. In some embodiments, each coil in the inside of the implant has two ends and each end contacts one or more wall-forming coils. In one embodiment, the inside of the implant also contains coils in the form of continuous closed loops, where for a given level (i.e. the width of one coil) at least one coil with smaller dimensions than the outer coil is concentric with, located inside and adjacent to the outer coil. Optionally, each level of coils contains two or more concentric coils, or sets or groups of coils.

The openings within and between the coils provide open spaces for bone in growth following implantation. Optionally, a bone graft substitute or bone graft material is present or inserted into the openings prior to implantation, at the time of implantation, or even following implantation. In some embodiments, the coils define a relatively large open space, typically located in the center of the implant, herein referred to as a central opening. The central opening may be one large open space. Alternatively a central opening can be divided into two or more smaller open spaces. The dividers may be in the form of coils, typically a plurality of stacked coils, or any other suitable shape.

i. Amount

The number of coils can vary depending on the application for the implant.

a. Set of Coils

Figure 3A:
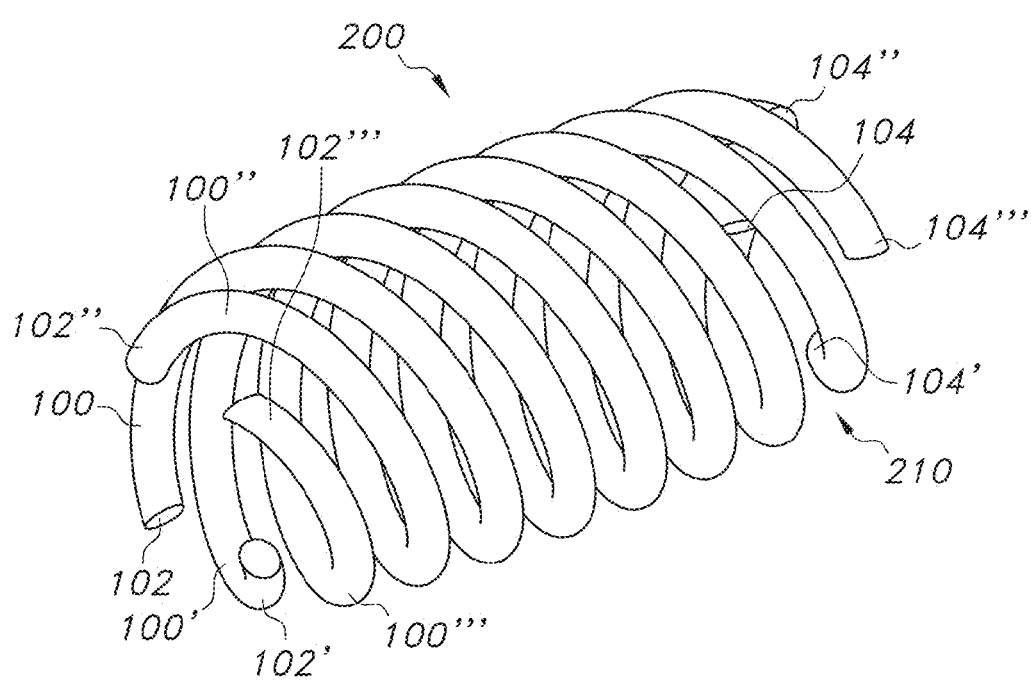
FIGS. 3A and 3B are two views of an exemplary set of coils, which can be used in an implant. The set of coils contains four helical coils, where the coils have substantially the same diameter and pitch.
Figure 3B:
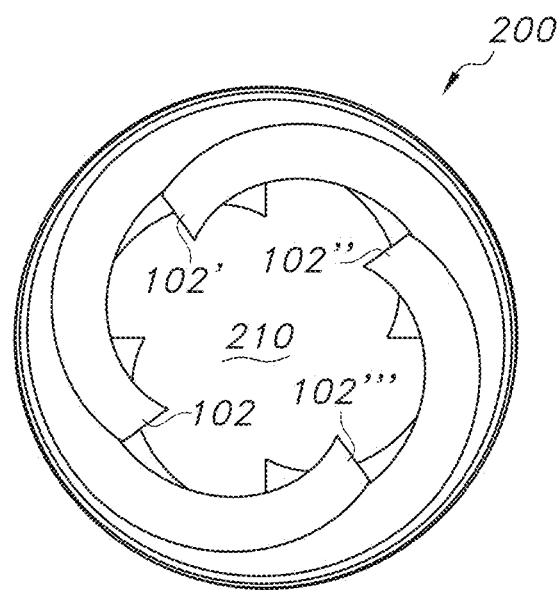

As used herein the term "set of coils" refers to two or more coils that are aligned along a common helical axis or path, where the coils do not intersect or contact each other. As used herein "helical axis" refers to a straight line that lies in the center of the coils, and about which the coils rotate (identified as "Z" on FIG. 1). As used herein "helical path" refers to a straight or curved line that lies in the center of the coils, and about which the coils rotate. In some embodiments, the coils in a set of coils are congruent. For example, FIGS. 3A and 3B depict a set 200 of coils that contains four congruent coils 100, 100', 100", and 100'''.

The coils in a set of coils are typically equally spaced apart from each other. For example, as shown in FIG. 3A, four coils form a set of coils, where all of the coils in the set are equally spaced 90° apart from each other. The end 102 of each coil is located 90° apart from the end 102' of an adjacent coil. As shown in FIG. 3A, the end 102 is 90° apart from the end 102' and the end 102"; the end 102" is 90° apart from the end 102'''. The same can be seen at the opposite end of the set of coils, see, e.g. ends 104, 104', 104" and 104''' of the coils 100, 100', 100", and 100''', respectively. Equal spacing for a given number (n) of coils can be calculated by dividing 360° by n; thus for a set containing three coils, the coils are spaced 120° apart and for a set containing six coils, the coils are spaced 60° apart.

Figure 6A:
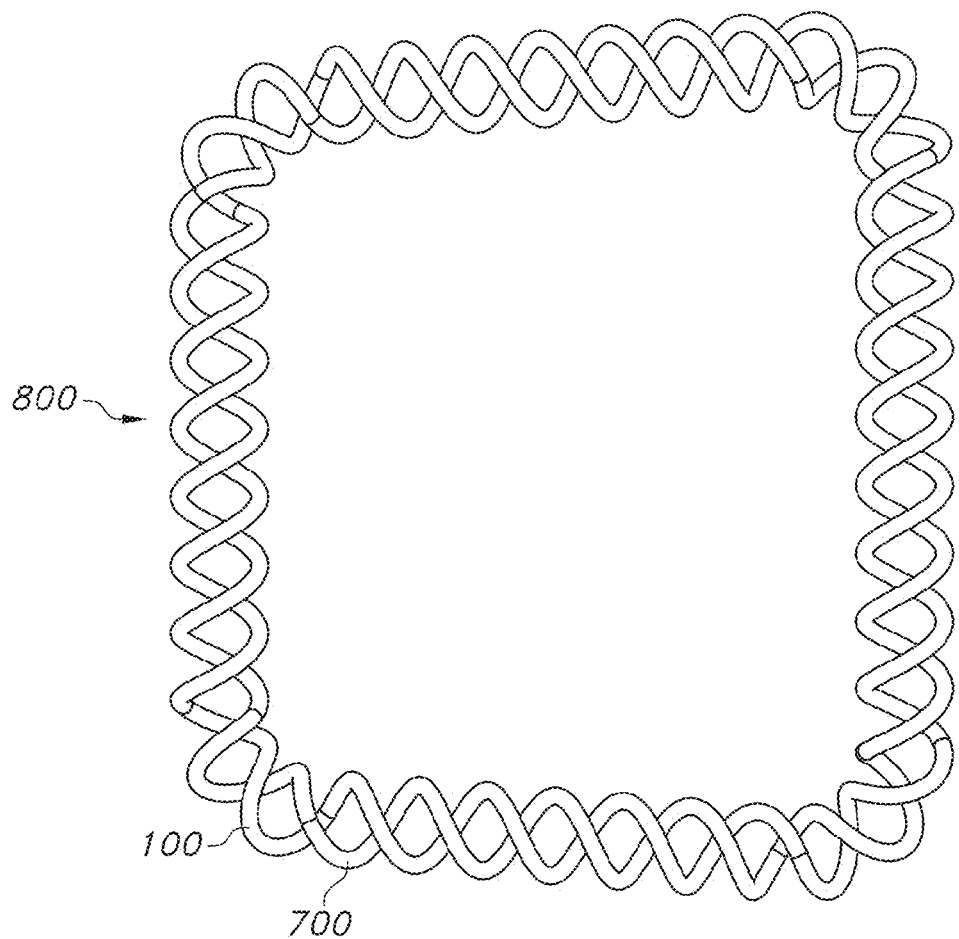
FIGS. 6A-6D are four views of an exemplary set of coils containing two congruent coils in the form of a continuous loop.
Figure 6B:
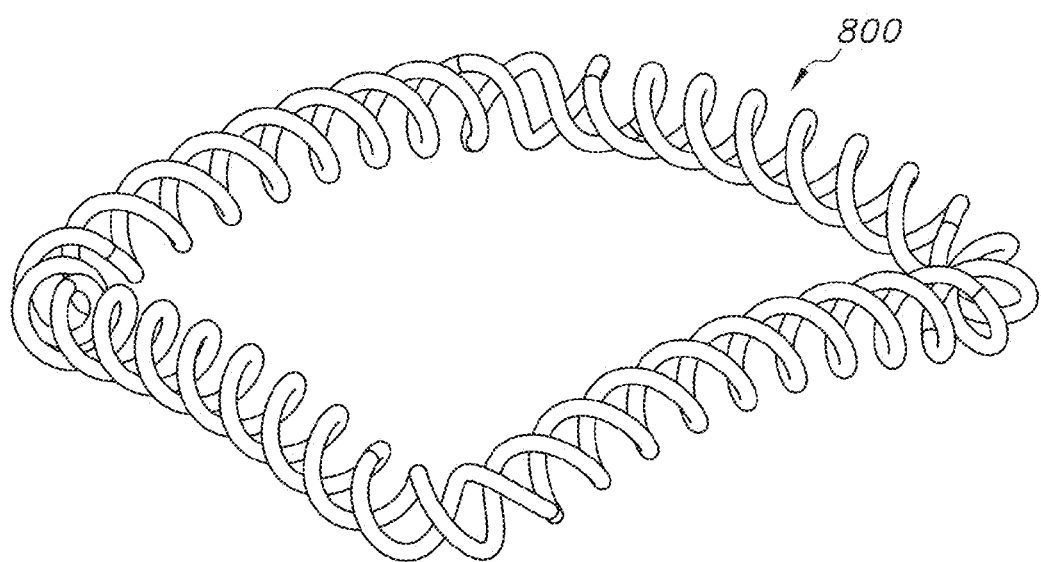

Similarly, as shown in FIG. 6A, two coils form a set of coils, where all of the coils in the set are equally spaced 180° apart from each other. Neither of the coils touches the other in a set of coils. In this embodiment, the set of coils is in the form of a continuous loop, which can be used to form part of an implant.

In some embodiments, the coils in a set of coils are not spaced apart from each other equal intervals.

b. Group of Coils

Figure 2:
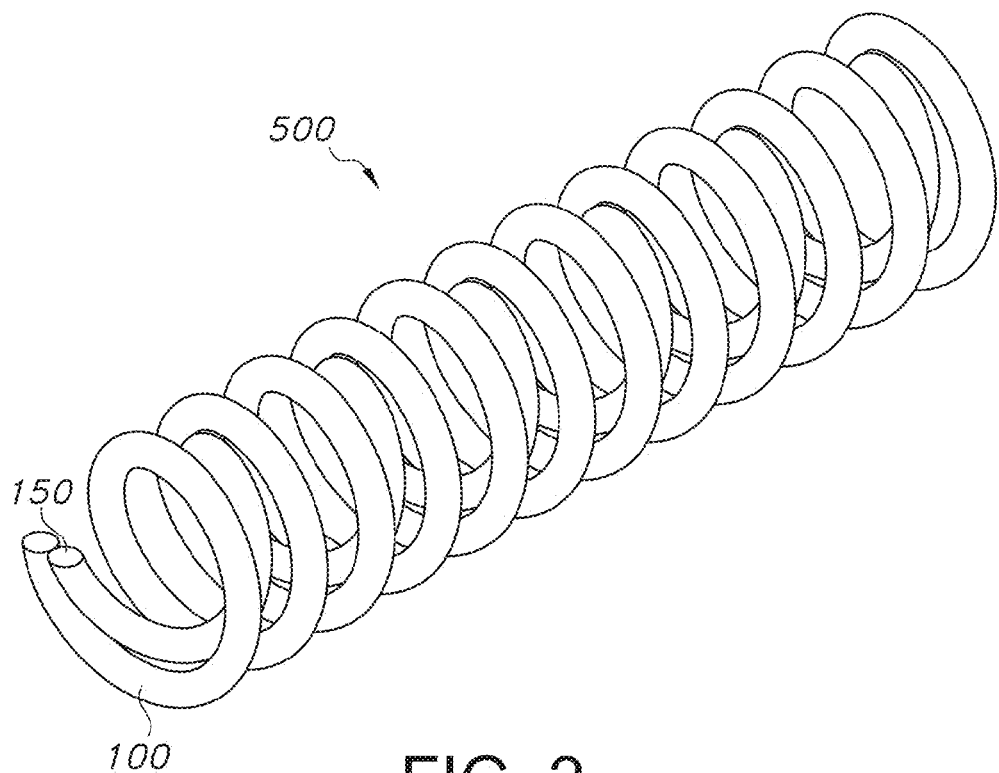
FIG. 2 is an illustration of an exemplary group of coils containing an outer coil and an inner coil.

As used herein the term "group of coils" refers to more than one coil, where at least one coil has a larger diameter than at least another coil, and wherein the coil(s) with a smaller diameter (referred to as the "inner coils") are inside the one or more coils with a larger diameter (referred to as the "outer coils"). For groups of coils containing two or more outer coils surrounding two or more inner coils, the number of outer coils is typically the same as the number of inner coils. FIG. 2 illustrates an exemplary group of coils 500 that contains a single outer coil 100 and a single inner coil 200. The group of coils depicted in FIG. 2 contains a total of two coils.

The outer coils and the inner coils in a group of coils preferably have different pitches, most preferably the inner and outer coils are aligned in a staggered or offset manner, preferably the coils are aligned so that the coils are about 180° apart. See, e.g. FIG. 2.

If tight packing is required for the coils to provide a strong implant that resists deflection under a constant load, the number of coils could range from about 10 to about 100, preferably from about 30 to about 60. Additionally, the implant may contain a first set of about 30 to about 60 outer congruent coils, and a second set of about 30 to about 60 inner congruent coils.

Figure 4A:
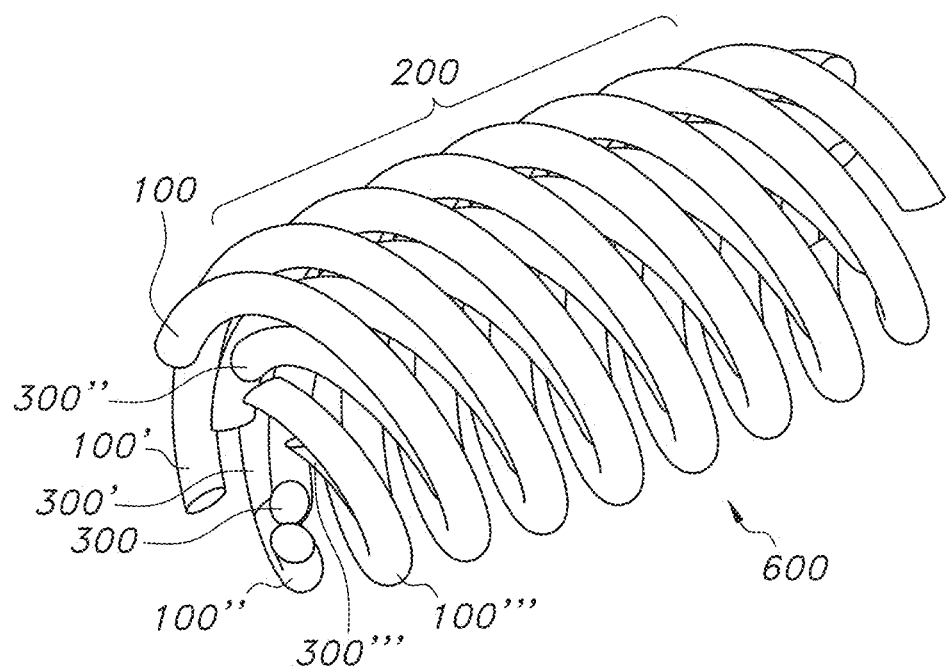
FIGS. 4A and 4B are two views of an exemplary group of coils, which can be included in an implant. The group of coils contains a first set of four outer helical coils and a second set of four inner helical coils. The second set of coils is inside the first set of coils.
Figure 4B:
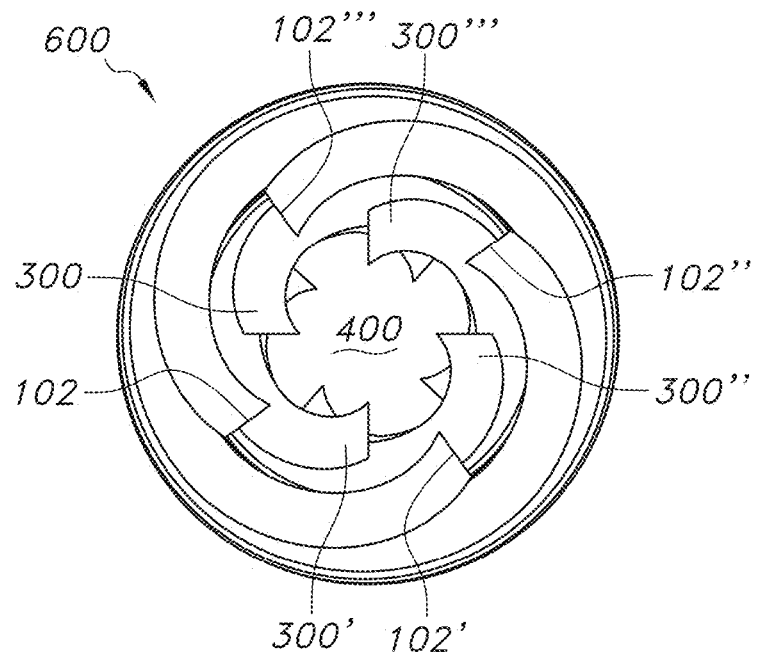

For example, FIGS. 4A and 4B shows a group of coils that can be used to form an implant. The group 600 contains a first set 200 of four outer helical coils 100, 100', 100", and 100''' and a second set 400 of four inner helical coils 300, 300', 300", and 300'''. The second set of coils 400 is inside the first set of coils 200. The coils in each set are congruent. The group of coils depicted in FIGS. 4A and 4B contains a total of eight coils.

Optionally, an implant may contain one or more additional sets of congruent coils within the first and second sets of coils (not shown in Figures).

ii. Size

Different coils in an implant may have different diameters. For example, in a group of coils, the outer coils have a larger diameter than the inner coils.

Additionally, diameters for a given coil may vary along the coil, such as where the greatest diameters are in the center of the coil and the smallest are at the distal and proximal ends of the same coil. Alternatively, the greatest diameter may correspond with one end of the coil and the smallest diameter may correspond with the opposite end of the coil.

ii. Shapes

One or more of the coils can have major and minor diameters (D1 and D2) with different values, such that the coil is an elliptical coil. One or more of the coils, have the same major and minor diameters, such that the coil is a circular helical coil. In yet other embodiments, one or more of the dimensions in a given coil may vary, for example, the major and/or minor diameters (D1 and D2) of the coil may vary over the length of the coil.

The cross-section of each coil can have any suitable shape. Exemplary cross-sectional shapes include but are not limited to circles, ellipses, stars, squares, rectangles, ovals, hexagons, octagons, and non-symmetric shapes. The largest dimension ($\alpha$) of the cross-section for the coil is generally more than or equal to 0.7 mm. For example, when the cross-section of the coil is in the shape of a circle, the diameter (d) of the circle is typically less than or equal to 0.7 mm. See, e.g. FIG. 1.

B. Configuration of Implant

The implant can have any suitable configuration depending on the desired use for the implant.

Typically an implant includes at least two coils (or sets or groups of coils) that are adjacent to each other and intersect with each other at one or more intersection regions. The coils may intersect at a plurality of intersection regions, optionally along an array of intersection regions. The intersection regions are generally not located on the outer surfaces of the implant that contact an adjacent bony surface, such as the outer inferior or superior surfaces in an interbody fusion spacer. Rather, the intersection regions are generally located in the inside of the implant and/or the side walls of the implant.

In one embodiment, the implant is formed from a plurality of coils, such as closed loop coils. Typically the implant contains more than one level, where each level contains more than one closed loop coils. For example, in a level containing two or more closed loops, the sets or groups of coils are concentric closed loops that are aligned one within the other to form the level. Typically, each closed loop contains two or more congruent coils in the form of a set of coils. Optionally, the implant contains one or more plates and one or more sets of interrupted loops, where one end of a coil is in contact with one side of a plate and another end of the same coil is in contact with another side of the same plate or a side of a second plate.

In an alternative embodiment, the implant contains a plurality of coils, such as in the form of coiled segments, optionally in the form of coiled arcs, further optionally in contact with one or more plates.

In an alternative embodiment, the side walls of the implant contain a plurality of stacked closed loops, and the inside portion of the implant is formed from stacks of coils. The center of each stack of coils typically has a larger diameter than the other coils in the stack. Typically the coils that form the stack of coils are in the form of a set or group of two or more coils, which is stacked with a plurality of sets or groups of two or more coils.

In yet a further alternative embodiment, the implant comprises a plurality of coils or sets of coils comprising at least two coils and an opening between and/or inside the coils, wherein the implant comprises one or more outer walls, a superior surface and an inferior surface, and a central support portion. The central support portion is inside the outer wall(s). The superior surface and inferior surface are formed from the plurality of coils or sets of coils. The outer wall is formed from the intersection of two or more exterior coils or sets of exterior coils at intersection regions. The outer wall(s) is preferably in the form of a smooth peripheral ring.

In preferred embodiments, the implant is symmetric about one or more planes of symmetry. In preferred embodiments, the implant is symmetric about both the median plane M and the transverse plane T.

In some embodiments, the exterior and interior surfaces of the implant are not smooth, rather they are textured or porous. However, typically, the side wall, such as a peripheral ring and the plates attached thereto or incorporated therein are smooth, i.e. they are not textured and/or porous.

1. Side Wall(s)

The outer surfaces of the implant generally include one or more side walls, typically four side walls, or more than four side walls, a superior outer surface and an inferior outer surface. In some embodiments, the one or more side walls are formed from a plurality of coils, where the coils are in the form closed loops or interrupted loops. For example, a plurality of coils, such as closed loops or interrupted loops, may be stacked on top of each other to form the side walls of the implant. In some embodiments, the one or more side walls are formed from a plurality of coiled segments, optionally in the form or one or more coiled arcs.

Optionally, the side wall(s) are substantially smooth to prevent injury to tissues during insertion of the implant.

In some embodiments the side wall is in the form of a smooth peripheral ring, or two or more peripheral ring segments. The smooth peripheral ring offers further strength to an implant during impaction and helps distribute impaction forces. For example, in implants where the exterior sets of coils are expected to support most pressure load, such as in an interbody fusion spacer, where the exterior coils or sets of coils rest on the apophyseal ring, the peripheral ring adds additional axial mechanical strength to the exterior sets of coils. Additionally, the smooth surface provided by a smooth peripheral ring can minimize shearing nearby tissues when the implant is in contact with tissues at various stages of placement, including the impaction stage.

2. Plate(s)

The side wall (s) of the implant may include one or more plates. In some embodiments one of the side walls, or a portion thereof, is replaced with a plate that is integral with the rest of the implant.

The term "plate" as used here in generally refers to a portion of the implant that is located at an exterior surface or forms part or all of an exterior surface of the implant. It can be a flat or rounded surface. A plate is generally not formed from one or more coils.

In embodiments containing more than one outer wall, optionally, one of the plates defines one of the walls of the implant and is connected with two other walls of the implant. In some embodiments, the outer wall is in the form of a peripheral ring that contains an anterior plate at the anterior end of the implant and a posterior plate at the posterior end of the implant.

When a plate is present in an implant, it may intersect with one or more coils to form one or more of the side wall(s) or a portion of a side wall.

3. Open Spaces

The implants described herein contain open spaces, such as in the center of the implant, between and/or within the coils, and/or between the coils and the central support portion to facilitate bone growth in and through the implant. A portion or all of the open spaces is optionally filled with a bone graft or bone graft substitute prior to or after insertion of the implant in the site in a patient to facilitate bone growth.

The total volume of the open spaces within any particular implant is dependent on the overall dimension of the implant as well as the size and dimension of individual components within the implant including coils, central support (if present), anterior plate, posterior plate, etc. The void volume typically ranges from about 20% to 80% of the volume of the implant. Optionally, the void volume of an implant is at least 20%, 25%, 30%, 35%, 40%, 45%, 50%, 55%, 60%, 65%, 70%, 75%, or 80% of the volume of the implant. Preferably for an interbody fusion spacer, such as an ALIF implant, the percent void volume is at least about 25%, more preferably at least about 40% of the total volume of the implant and at most 80% of the implant's total volume, preferably the void volume ranges from about 25% to 75%, more preferably from about 40% to 75%.

4. Different Uses for the Implants

The implants for use in the spine have overall dimensions suitable for insertion in the spine, typically between two vertebral bodies. The shape of the implant and dimensions depends on the site into which it is inserted. For example, for ALIF devices, the implant typically has an anterior-posterior depth of 18 mm or greater, preferably from about 20 mm to about 40 mm; a lateral width of 24 mm or greater, such as from about 24 mm to about 46 mm; and a height (at its highest point) ranging from 6 mm to 60 mm. Suitable diameters for the coils that are used to form the implant are typically at least 0.79 mm in diameter.

i. Exemplary Embodiment of Implant with Rows of Stacked Coils Surrounded by Walls Formed from Stacks of Closed Loops In some embodiments, the inside portion of the implant is typically filled with rows of stacked coils. In each row of stacked coils, all of the coils align along a single axis (z). The number of coils (or sets of coils) in each row may be the same or different. Additionally, the number of coils (or sets of coils) in each of the rows that form the inside of the implant may be the same as the number of coils (or sets of coils) that are stacked to form the side walls. The top and inferior portions of the plurality of rows of stacked coils form the superior outer surface and inferior outer surface, respectively. Typically, in the central row of the plurality of rows the central coil (set of coils or group of coils) has a greater diameter than the other coils in the same row (referred to herein as the "central support coil" 850). The 3-D printing process builds the implant from the bottom up or top down (as it needs a support structure to builds layers on top of each other).

The packing density for the coils varies depending on the use for the implant.

As depicted in FIGS. 5A-5D, the implant 1000 contains four side walls 1100, 1200, 1300, and 1400, and an inside portion 1600.

The side walls are formed from a plurality of stacked closed loop coils. For example, the implant depicted in FIGS. 5A-5C contains six rows of sets of closed loop coils, where each set 800 of coils contains two congruent coils 100 and 700.

Figure 5A:
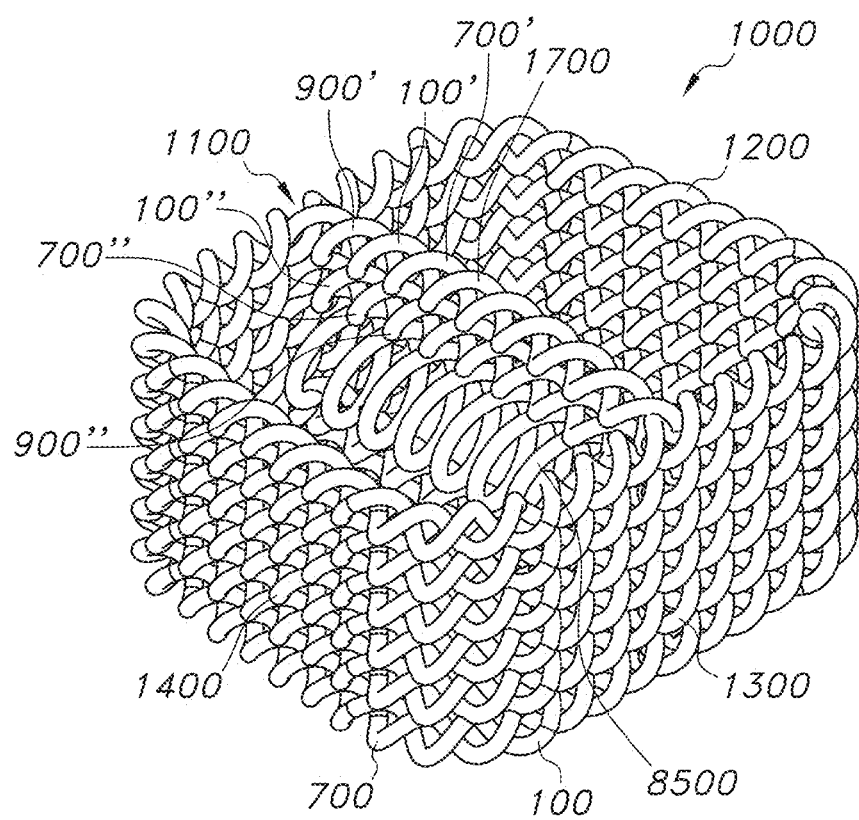
FIGS. 5A-5D are three views of a partially formed implant, showing the outer walls and a single stack of coils in the inside portion of the implant. A complete implant typically contains a plurality of stacks of coils in the inside portion of the implant.
Figure 5B:
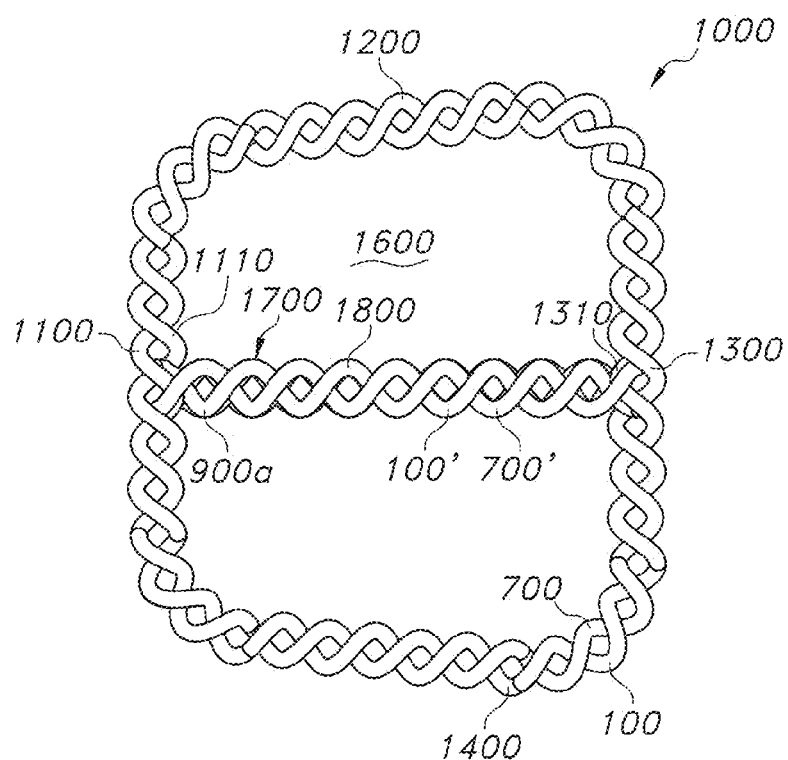
Figure 5C:
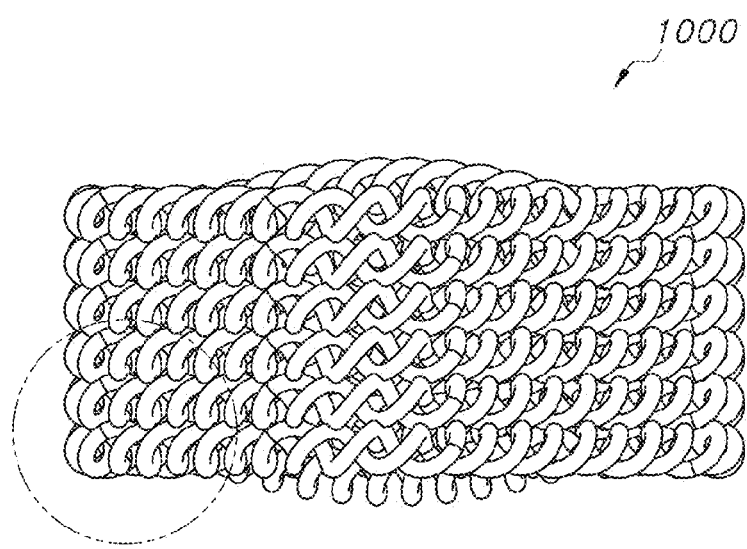
Figure 5D:
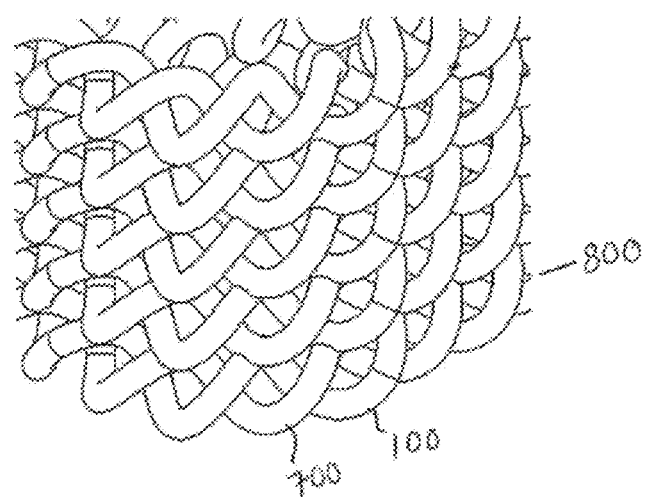

Only one row 1700 of stacked coils is shown in the inside portion 1600 of the implant depicted in FIGS. 5A-5C for ease of viewing. As shown in the figures, the superior outer surface 1800 and inferior outer surface (not shown in figure) are defined by the superior and inferior portions of the row 1700 of coils. However, typically the implant contains a plurality of rows of stacked coils, where the superior portions of each of the rows forms the complete superior outer surface and the inferior portion of each of the rows forms the complete inferior outer surface.

Similar to the side walls, the row 1700 of coils preferably contains a stack of six sets of coils, where each set of coils 900' and 900" contains two congruent coils 100' and 700'. The ends of each coil attach to the inner portion 1110 and 1310 of a side wall 1100 or 1300, respectively. Optionally, in place of a stack containing sets of coils, the stack may contain single coils or groups of coils, such as depicted in FIGS. 3A-3B and 4A-4B, or combinations or variations of such sets and groups of coils.

ii. Exemplary Implant Formed from Plurality of Closed Loop Coils and/or Interrupted Loops In another embodiment, such as depicted in FIGS. 7A and 7B, FIGS. 9A-D, and FIGS. 10A-D, the implant contains a plurality of closed loop coils and/or interrupted loops, such as in the form of stacked loops that form the side walls and substantially concentric loops that form the superior and inferior surfaces of the implant along with the inside of the implant.

The implants can have any suitable size and shape, which depends on the use for the implant. The implant contains a plurality of side walls, typically at least four side walls, optionally more than four side walls, a superior surface and an inferior surface. The closed loop coils typically contain more than one coil, in the form of a set of coils or a group of coils. In a preferred embodiment, each of the closed loop coils is a set of coils. The implant preferably contains more than one level of closed loop coils, where each level contains at least one and preferably more than one closed loop coil. In a preferred embodiment, each level contains a plurality of concentric closed loop coils where the outermost closed loop coil has the greatest dimensions (e.g. diameter) and the dimensions of each adjacent closed loop coil moving towards the interior of the implant is smaller than the adjacent outer closed loop coil.

Figure 7A:
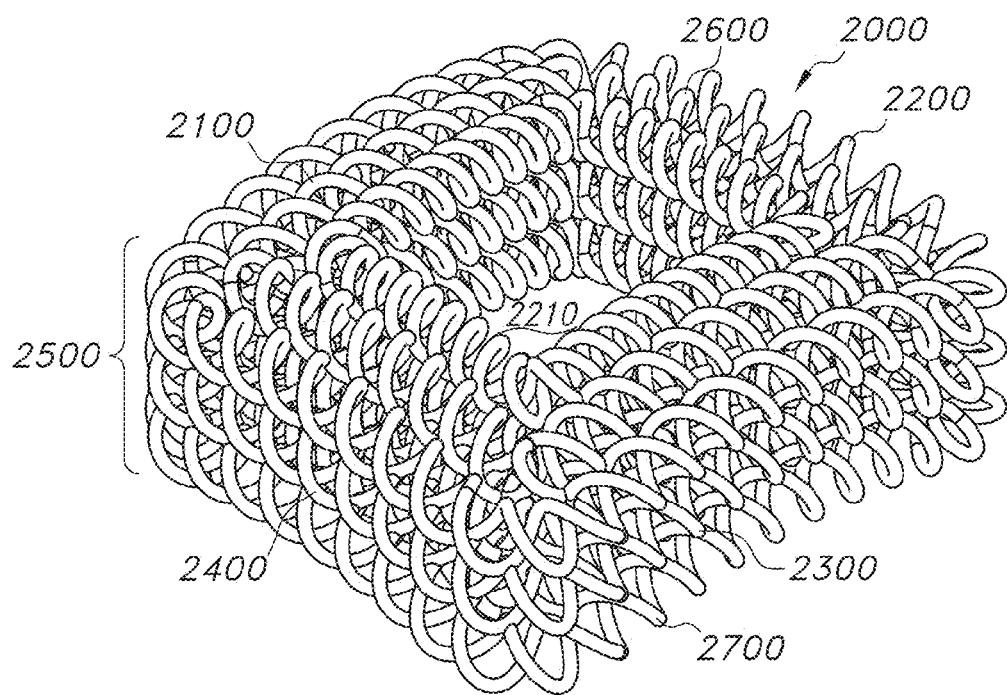
FIGS. 7A and 7B are two views of an exemplary implant. In these figures, the exemplary implant contains three levels of coils, where each level contains three sets of coils, and each set contains two congruent coils.
Figure 7B:
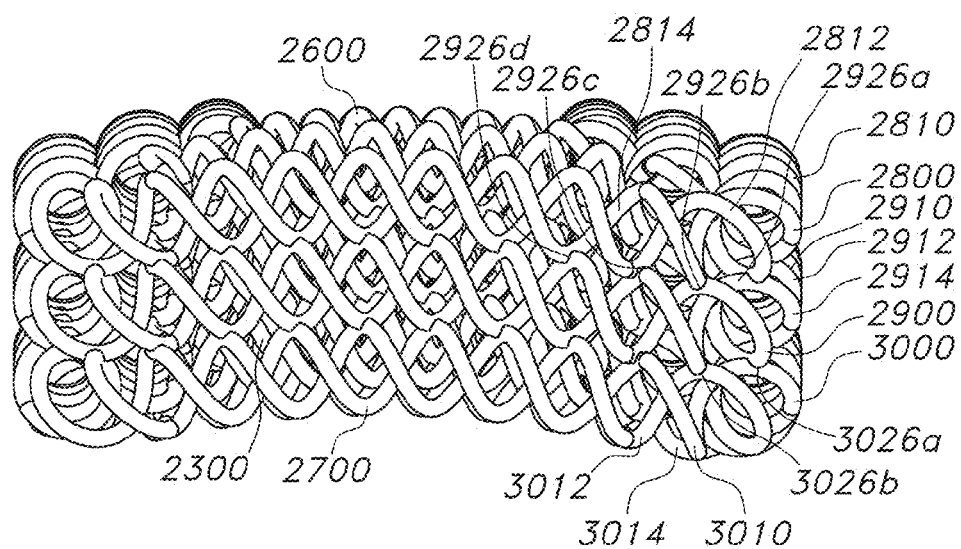

As depicted in FIGS. 7A and 7B, the implant 2000 contains four side walls 2100, 2200, 2300, and 2400, an superior surface 2600, and an inferior surface 2700.

The side walls are defined by the outer surfaces of a plurality of stacked closed loop coils. For example, the implant depicted in FIGS. 7A and 7B contains three levels of coils, where each level contains three sets of coils, and each set contains two congruent coils.

a. Set of Coils in the Form of a Closed Loop

A single set 800 of coils in the form of a continuous closed loop is shown in FIGS. 6A-6D for ease of viewing. As shown in FIGS. 6A-6D, each set of coils 800 contains two congruent coils 100 and 700. The number of coils in each set is merely for illustrative purposes, and one of skill in the art would understand that each set can have the same number of congruent coils or different numbers of congruent coils. Additionally the number of congruent coils in each set can vary as needed, such as at least 1, 2, 3, 4, 5, 6, 7, 8, 9, or, 10 or more congruent coils in each set. Other amounts, such as 15 or more, 20 or more, or even greater numbers of congruent coils in each set are also envisioned.

Figure 6C:
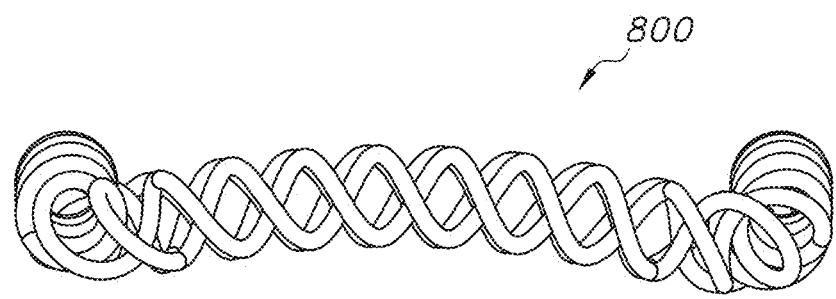
Figure 6D:
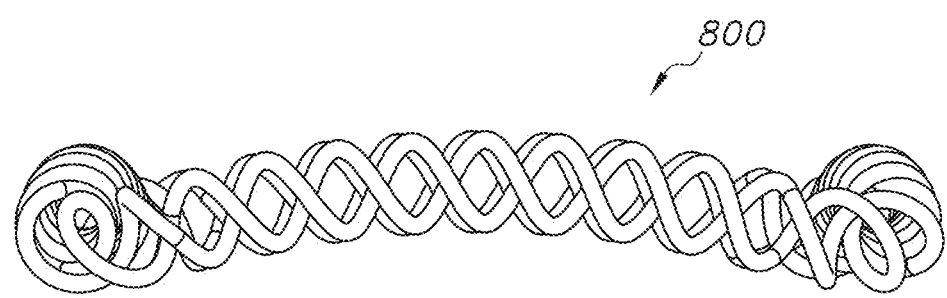

The curvature for a single closed loop can be seen in the side views (FIGS. 6C and 6D). In some embodiments, each set of coils may have a profile that generally corresponds with the convexity or concavity of the surface inside the body that will be adjacent to the superior or inferior surface of the implant. For example, as depicted in FIG. 6C and FIG. 6D, the closed loop may have the profile of a convex or concave surface. The convex surface shape is particularly useful for spinal fusion implants.

In some embodiments, only the superior or inferior surfaces have a profile that corresponds with the convexity or the concavity of the adjacent surface in the body. For example, the one or more sets of coils in the level, that forms the superior or inferior surface of the implant, may have a modified shape, such that the superior surface of the implant is flatter than the regular coil, and generally corresponds with an adjacent concave surface, such as the end of a vertebral body.

b. Levels of Concentric Coils

The implant may have any suitable number of levels, and each level may contain any suitable number of concentric loops of coils. Suitable numbers of levels range from 2 to 100 or even more, depending on the radius of the loops and the overall size of the implant. Typically for spinal implants, the number of levels ranges from 2 to about 40, preferably from 2 to 30, more preferably from 2 to about 10, preferably from 2 to 6.

Only one level 2800 of concentric coils (or concentric sets of coils) is depicted in FIGS. 8A-8D for ease of viewing. As shown in these figures, the level is formed from three sets 2810, 2820, and 2830 of coils, where each set of coils contains two congruent coils, e.g. 2812 and 2814 in set 2810. The number of sets of coils in each level is merely for illustrative purposes, and one of skill in the art would understand that each level can have the same number of concentric coils or different numbers of concentric coils. Additionally the number of concentric coils in each level can vary as needed. For example, each level can contain at least 1, 2, 3, 4, 5, 6, 7, 8, 9, or, 10 or more concentric coils. Other amounts, such as 15 or more, 20 or more, or even greater numbers of concentric coils in each level are also envisioned.

The superior outer surface 2850 and inferior outer surface (not shown in figure) are defined by the superior and inferior portions of the level 2800 of coils.

Figure 8A:
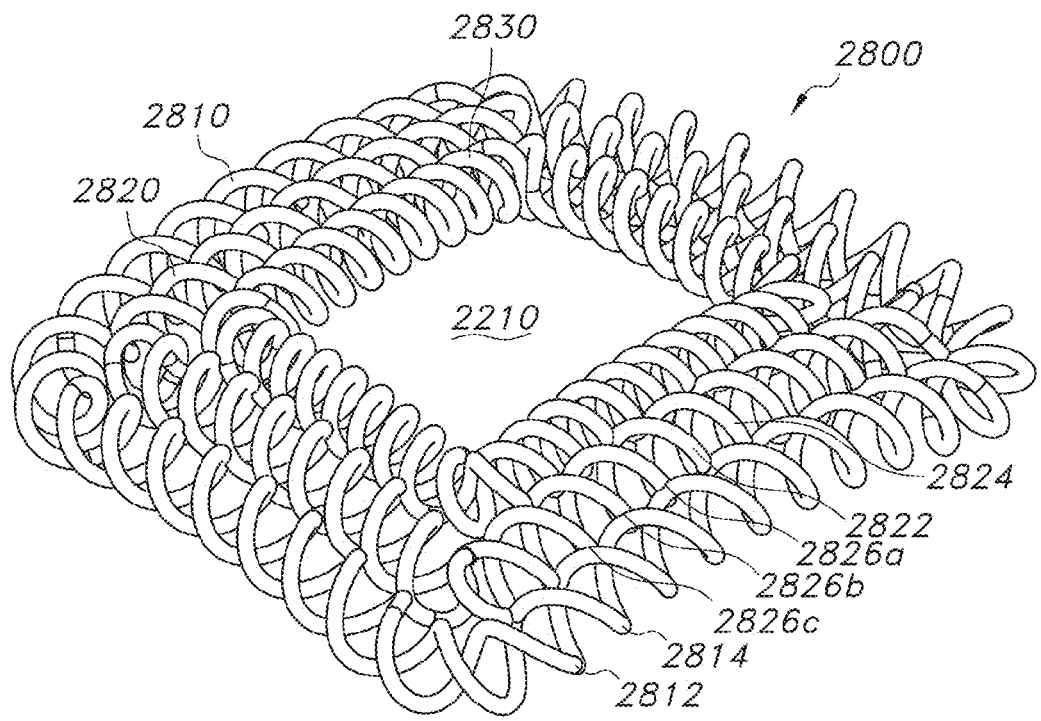
FIGS. 8A-8D are four views of one exemplary level in an exemplary implant. In these figures, the level contains three sets of coils, and each set contains two congruent coils.
Figure 8B:
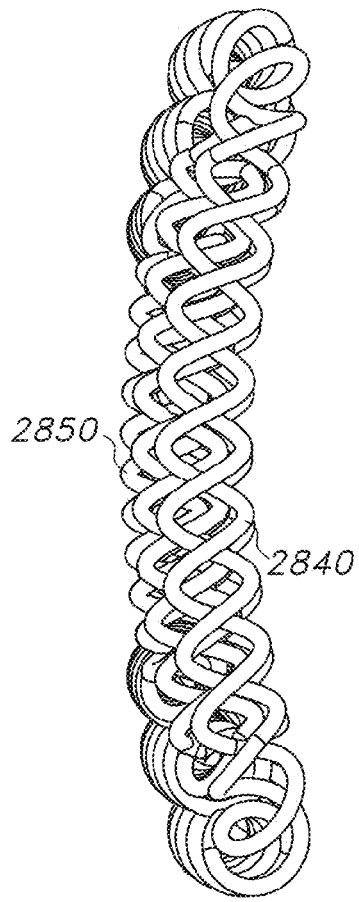
Figure 8C:
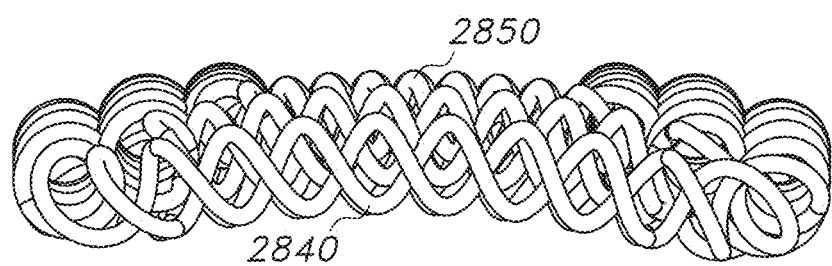
Figure 8D:
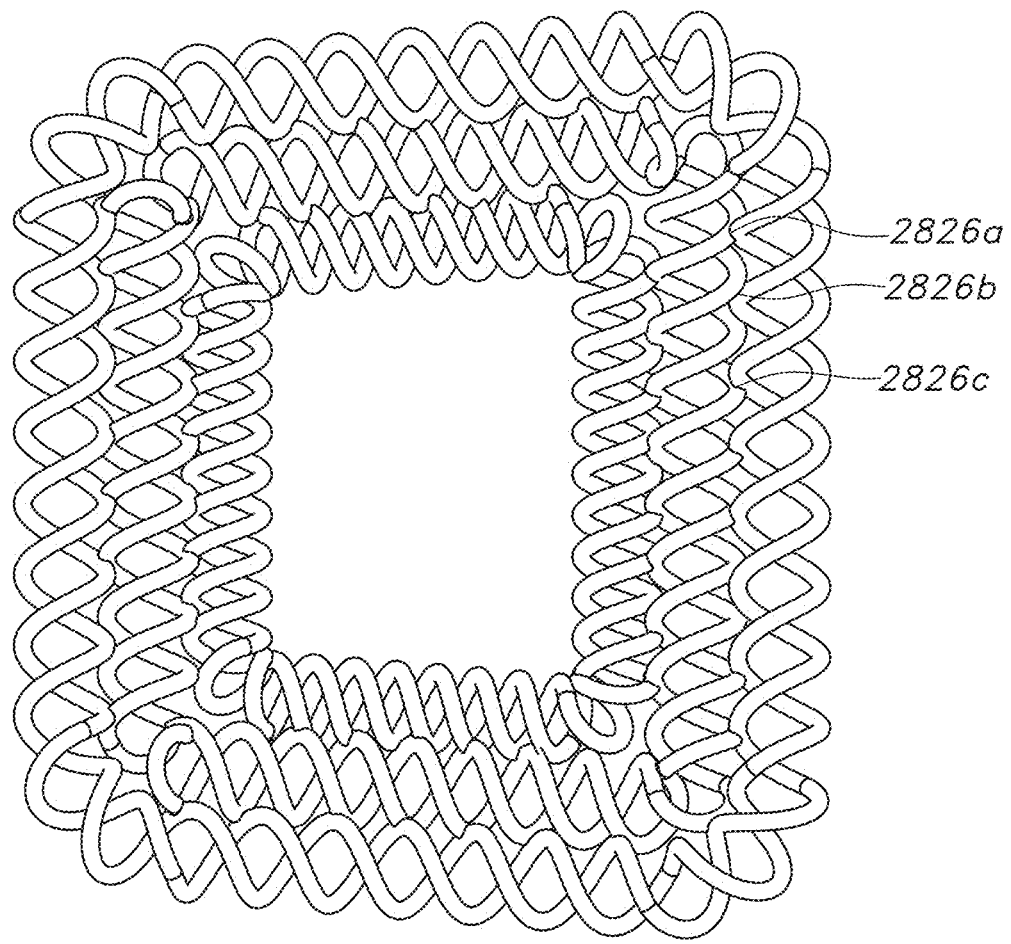

Coils in adjacent sets of coils within a given level or on adjacent levels intersect with each other at intersection regions at regular intervals, i.e. the same angle within the rotation of the coil 2810. As shown in FIGS. 8A and 8C, coils 2812 and 2814 in the outer set of coils 2810 insect at regular intervals with the coils 2822 and 2824 in the adjacent set of coils 2820 at intersection regions 2826a, 2826b, and 2826c. The intersection regions are located at the same relative position with respect to each connecting coil. For example, connecting coils 2812 and 2822 connect at intersection regions when 2812 is at the 0° position and 2822 is at the 180° position. Similarly, connecting coils 2814 and 2824 connect at intersection regions when 2814 is at the 0° position and 2824 is at the 180° position.

c. Exemplary Bi-Convex Implant

Typically, an implant contains a plurality of levels of concentric coils and the superior portions of each of the interior levels intersect with the inferior portion the adjacent level of coils at regular intersection regions, as discussed above. As shown in FIGS. 7A and 7B, the implant contains three levels of concentric closed loops 2800, 2900, and 3000. The number of levels in the implant is merely for illustrative purposes, and one of skill in the art would understand that each implant can have a different number of levels, depending on the size of the implant and the size of the coils in the implant. For example, the number of levels in an implant can be 2 or greater, such as 10 or greater, 15 or greater, 20 or greater, or up to 40 levels. In some embodiments, the implant may contain an even greater amount of levels, such as up to 100 or up to 1000.

Looking at the outer closed loop (2810, 2910 and 3010) in each level, the outer set of coils 2910 contains two coils 2912 and 2914, which connect with the outer set of coils 2810 and 3010 in the adjacent levels at regular intervals. For example, each of the coils 3012 and 3014 in the outer set of coils 3010 connects with one of the coils in the outer set of coils 2910 at intersection regions 3026a, 3026b, and 3026c, located at the same relative location along the coil at regular intervals. Similarly, each of the coils in the outer set of coils 2810 connects with one of the coils in the outer set of coils 2910 at intersection regions 2926a, 2926b, 2926c, and 2926d located at the same relative location along the coil at regular intervals.

iii. Exemplary Implant Formed from Plurality of Coiled Arcs

In another embodiment, such as depicted in FIGS. 11A-11E, the implant contains a plurality of coiled arcs, such as in the form of stacked coiled arcs that form the side walls and substantially concentric coiled arcs that form the superior and inferior surfaces of the implant along with the inside of the implant.

As alternatives to coiled arcs, coiled segments of any geometrical shape may be used in the implant.

The implants can have any suitable size and shape, which depends on the use for the implant. The implant contains a plurality of side walls, typically at least four side walls, optionally more than four side walls, a superior surface and an inferior surface. The coiled arcs typically contain more than one coil, in the form of a set of coils or a group of coils. In a preferred embodiment, each of the coiled arcs is a set of coils. The implant preferably contains more than one level of coiled arcs, where each level contains at least one and preferably more than one coiled arc. In a preferred embodiment, each level contains a plurality of concentric coiled arcs where the exterior coiled are has the greatest dimensions (e.g. radius) and the dimensions of the interior coiled arc are the smallest. Similarly, each intermediate coiled arc has a greater radius than the interior coiled arc, with the radius of the intermediate coiled arcs increasing moving outward relative to the center of the implant.

In some embodiments, the implant contains a plurality of coils or sets of coils that contain at least two congruent coils and an opening between and/or inside the coils, wherein the implant comprises outer side walls, a superior surface and an inferior surface, and an inside portion, wherein the inside portion is inside the outer side walls, wherein the outer side walls, superior surface and inferior surface are formed from the plurality of coils or sets of coils, and wherein the side walls are formed from a stack of a plurality of coils or sets of coils, wherein the coils or sets of coils are in the form of coiled arcs.

Optionally, the inside portion of the implant contains a plurality of rows of stacked coils or stacked sets of coils. Optionally, the number of coils or sets of coils in each row is the same as the number of coils or sets of coils in the stack of coils that forms the outer side walls.

The implant may further contain one or more plates, wherein the one or more plates are integral with the walls of the implant. Optionally, one of the plates serves as one of the walls of the implant and is connected at its sides with the other walls of the implant.

In some embodiments, one or more of the coils or sets of coils has a diameter (D) that varies over the length of the coil. Optionally, the diameter (D) is greatest at the anterior end of the implant and smallest at the posterior end. In other embodiments, the diameter (D) is greatest in the center of the implant and decreases moving from the center of the implant towards the anterior and the posterior ends of the implant. In some preferred embodiments, the implant is an anterior lumbar interbody fusion (ALIF) device.

As depicted in FIGS. 11A-11E, the implant 6000 contains side walls and superior and inferior surfaces defined by coiled arcs: the exterior sets of coiled arcs 6100, 6100' are symmetrical opposites of each other, with the median plane M of the implant as a plane of symmetry. The implant has another plane of symmetry in the transverse plane T, such that one level 6710 is the symmetrical opposite of the other level 6720 along the transverse plane T of the implant.

The side walls are defined by the outer surfaces of a plurality of sets of coiled arcs. For example, the implant depicted in FIGS. 11A-11E contains two levels 6710 and 6720, where each level contains six sets of coiled arcs, with three sets in one level on one side of the median plane M and the other three sets on the other side of the median plane M.

a. Set of Coiled Arcs

As shown in FIGS. 11A-11E, each set of coils 6100 contains two congruent coils 6110 and 6120. The number of coils in each set is merely for illustrative purposes, and one of skill in the art would understand that each set can have the same number of congruent coils or different numbers of congruent coils. The number of congruent coils in each set can vary as needed, such as at least 1, 2, 3, 4, 5, 6, 7, 8, 9, or, 10 or more congruent coils in each set. Other amounts, such as 15 or more, 20 or more, or even greater numbers of congruent coils in each set are also envisioned.

In some embodiments, each set of coiled arcs may have a profile that generally corresponds with the convexity or concavity of the surface inside the body that will be adjacent to the superior or inferior surface of the implant. For example, as depicted in FIG. 11E, the curved arcs may have the profile of a typical ALIF implant. This shape is particularly useful for spinal fusion implants.

In some embodiments, only the superior or inferior surfaces have a profile that corresponds with the convexity or the concavity of the adjacent surface in the body. For example, the one or more sets of coils in the level that forms the superior or inferior surface of the implant, may have a modified shape, such that the superior surface of the implant is more flat or more curved than a regular coil.

b. Levels of Coiled Arcs

The implant may have any suitable number of levels, and each level may contain any suitable number of concentric coiled arcs. For example, the number of levels may range from 2 to 1000 or even more, depending on the radius of the arcs and the overall size of the implant. Typically for spinal implants, the number of levels ranges from 2 to about 30, preferably from 2 to 20, or 2 to 10.

As shown in these figures, level 6710 is formed from three sets 6100, 6120, and 6130 of coiled arcs, where each set of coiled arcs contains two congruent coils, e.g. 6110 and 6120 in set 6100. The number of sets of coiled arcs in each level is merely for illustrative purposes, and one of skill in the art would understand that each level can have the same number of concentric coiled arcs or different numbers of concentric coiled arcs. Additionally the number of concentric coiled arcs in each level can vary as needed. For example, each level can contain at least 1, 2, 3, 4, 5, 6, 7, 8, 9, or, 10 or more concentric coiled arcs. Other amounts, such as 15 or more, 20 or more, or even greater numbers of concentric coiled arcs in each level are also envisioned.

The superior outer surface 6510 and inferior outer surface 6530 are defined by the superior surfaces 6112a, 6112b, etc., 6122a, 6122b, etc., 6212a, 6212b, etc., 6222a, 6222b, etc., of congruent coils 6110, 6120, 6210, 6220, 6310, and 6320 and inferior surfaces 6112a'', 6112b'', etc., 6122a'', 6122b'', etc., 6212a'', 6212b'', etc., 6222a'', 6222b'', etc., and 6312a'', 6312b'', etc., 6322a'', 6322b'', of congruent coils 6110'', 6120'', 6210'', 6220'', 6310'', and 6320'' of the level 6710 and 6720 of coiled arcs.

Coils in adjacent sets of coiled arcs within a given level or on adjacent levels intersect with each other at intersection regions. As shown in FIG. 11E, the coils 6110 and 6120 of the coiled arc 6100 in a first level 6710 intersect with the coils 6110'' and 6120'' of the coiled arc 6100'' in a second level 6720 at intersection regions 6520a, 6520b. Also, the coils 6110 and 6120 of the coiled arc 6100 intersect with the coils 6210 and 6220 of the coiled arc 6200 in the same level 6710 at intersection regions 6250a, 6250b, etc.

c. Exemplary Intervertebral Implant

In one embodiment, such as depicted in FIGS. 11A-11E, the implant contains a plurality of coiled arcs in each level: exterior coiled arcs 6100, 6100', intermediate coiled arcs 6200, 6200' and interior coiled arcs 6300, 6300'. The coiled arcs are formed from two congruent coils. For example, the exterior coiled arc 6100 is formed of two congruent coils 6110 and 6120, the intermediate coiled arc 6200 is formed of two congruent coils 6210 and 6220, and the interior coiled arc 6300 is formed of two congruent coils 6310 and 6320.

Looking at one half of the level 6710 when the implant is divided by the median plane M, the half 6910 contains three (3) intersecting coiled arcs formed of exterior coiled arc 6100, intermediate coiled arc 6200, and interior coiled arc 6300, which are arranged in a concentric arrangement. A second half 6920 of the level is a mirror image of the first half 6910. Together, the interconnecting coiled arcs of both halves 6910 and 6920 form a level 6710.

The implant depicted in FIGS. 11A-11E includes two levels of opposing concentric coiled arcs, the upper level 6710 and the lower level 6720. Collectively, the levels of the implant are 6700. The lower level 6720 is a mirror image of the upper level 6710 along the transverse plane T of the implant. In this embodiment, the implant is symmetric along the median plane M and along the transverse plane T.

The superior and inferior surfaces of the implant can be of any shape that conforms to, i.e., mates with, the shape of the adjacent vertebral endplates when the implant is in a patient's body. For example, the superior and/or inferior surfaces can be convex, concave, or bi-convex, etc., in shape. This provides a secure and tight fitting of the implant in the intervertebral disc space. In this embodiment, the congruent coils 6110, 6120, 6210, 6220, 6310, and 6320 contain flattened superior surfaces 6112*a*. 6112*b*, etc. 6122*a*, 6122*b*, etc., 6212*a*. 6212*b*, etc., 6222*a*, 6222*b*, etc., collectively forming the superior surface 6510 of the implant. Similarly, in the lower level 6720, congruent coils 6110", 6120", which form the exterior coiled arc 6100", congruent coils 6210", 6220", which form the intermediate coiled arc 6200", and the two congruent coils of the interior coiled arc (not shown in Figures) contain flattened inferior surfaces 6112*a*", 6122*a*", etc. The flattened surfaces of the coils in the coiled arcs of the lower level 6720 collectively form the inferior surface 6530 of the implant.

The implant also includes an anterior plate 6600, and a posterior plate 6400. The coils connect to both of these plates via their connection ends. For example, coil 6110 connects at connection end 6111 with the interior side of plate 6400 and coil 6120 connects at connection end 6121 with the interior side of plate 6400. The anterior plate 6600 includes a hole 6620 configured to receive an insertion instrument, bone graft deployment instrument, or separate fixation to the adjacent bony anatomy. Viewed from the anterior A of the implant, the exterior coiled arcs 6100, 6100' the intermediate coiled arc 6200, 6200' and the interior coiled arc 6300, 6300' extend from the anterior plate 6600 in a curved manner towards the posterior plate. At the posterior P of the implant, the congruent coils 6110 and 6120 of the exterior coiled arc 6100 merge with the posterior plate 6400 at connection ends 6450*a*, 6450*b*, etc. At the posterior P of the implant, the congruent coils 6210 and 6220 of the intermediate coiled arc 6200 and the congruent coils 6310 and 6320 of the interior coiled arc 6300 merge with their respective mirror image congruent coils along the median plane M, at connection ends 6420*a*, 6420*b*, 6420*c*. As the coils extend from the anterior plate 6600 towards the posterior plate 6400, the diameter (D) of the coils decreases, reaching the smallest diameter at the posterior P of the implant.

Figure 11A:
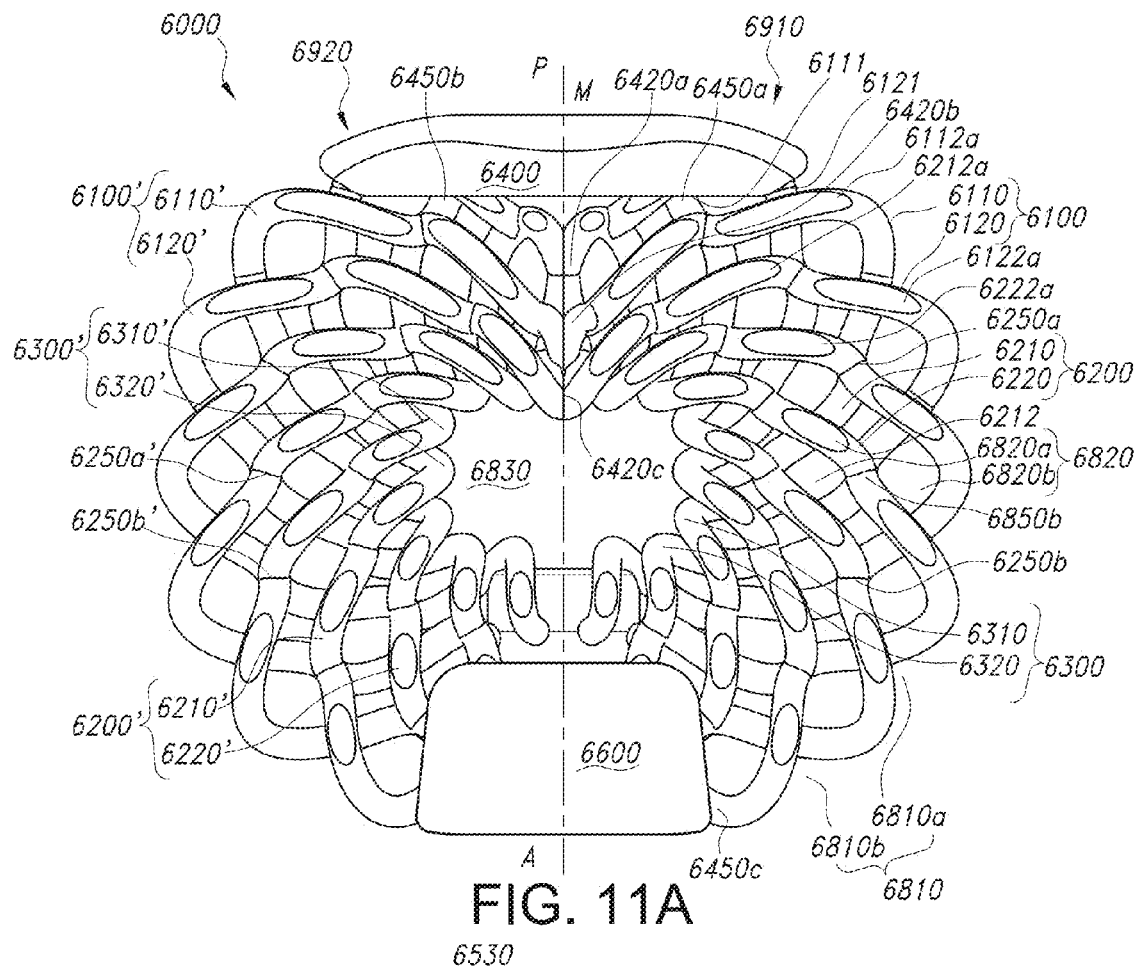
FIGS. 11A-11E are five views of an exemplary implant for use as an anterior cervical and/or anterior lumbar interbody fusion (ALIF) spinal fusion device. The exemplary implant contains an anterior plate integrated with the cage and configured to facilitate insertion of the cage into a patient, and a posterior plate, typically in the shape of a wedge with a rounded end. In these figures, the exemplary implant contains two levels of concentric sets of coiled arcs, where each level contains six sets of coils, and each set contains two congruent coils. Each set of coiled arcs in a level is a mirror image of the corresponding set of coiled arcs in the same level, where the axis of symmetry is along a line M that runs through the middle of the implant from the anterior end A to the posterior end P. Similarly the implant has plane of symmetry in the transverse plane T, such that one level is the symmetrical opposite of the other level along the transverse plane T of the implant.
Figure 11B:
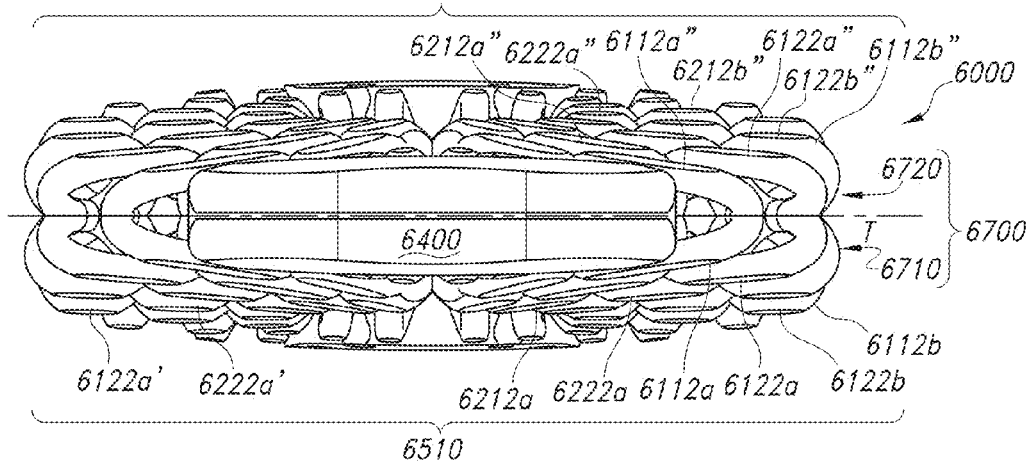
Figure 11C:
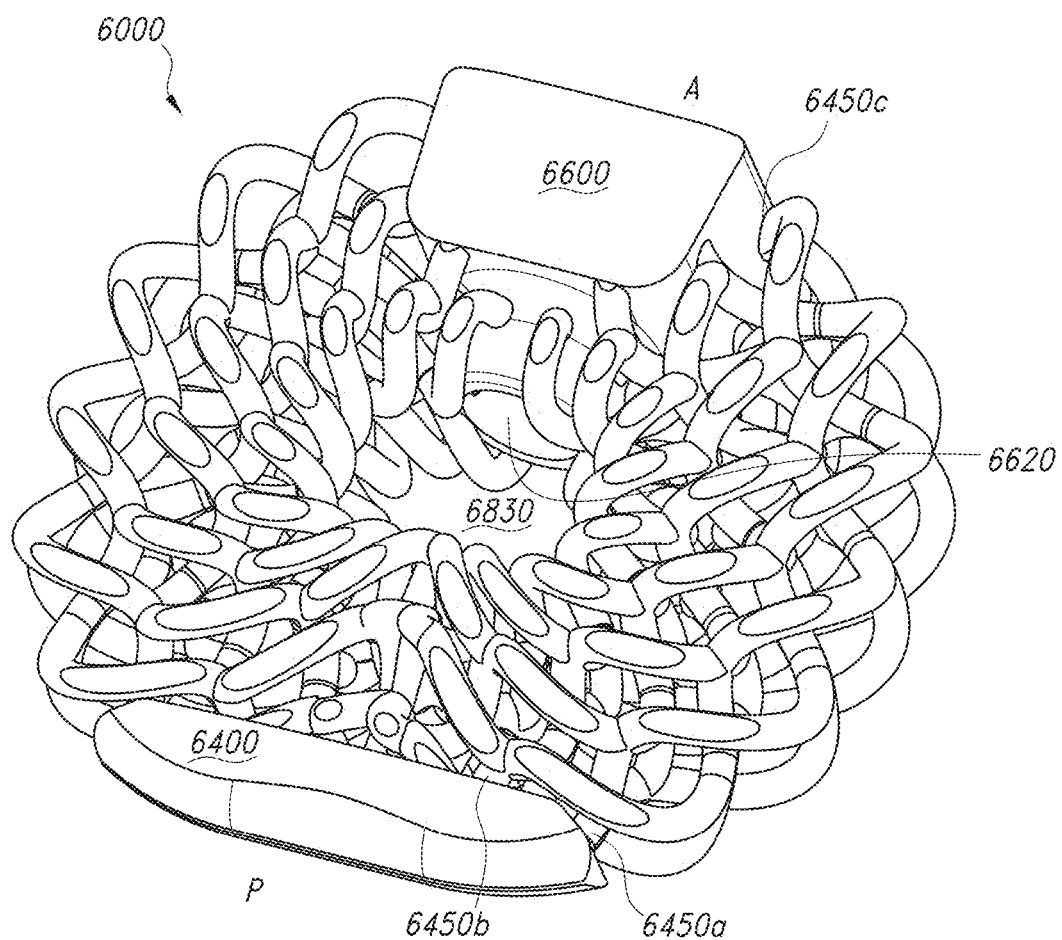
Figure 11D:
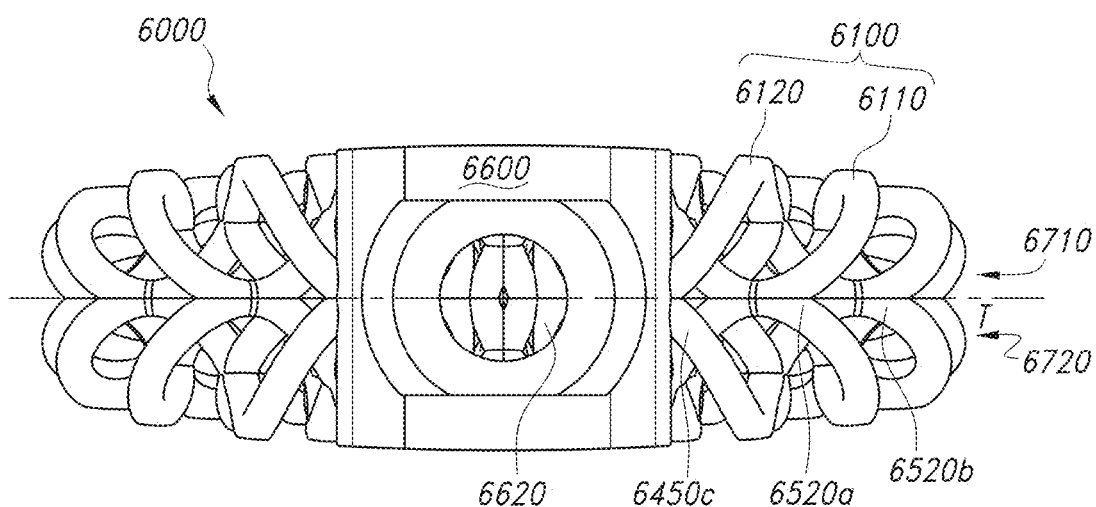
Figure 11E:
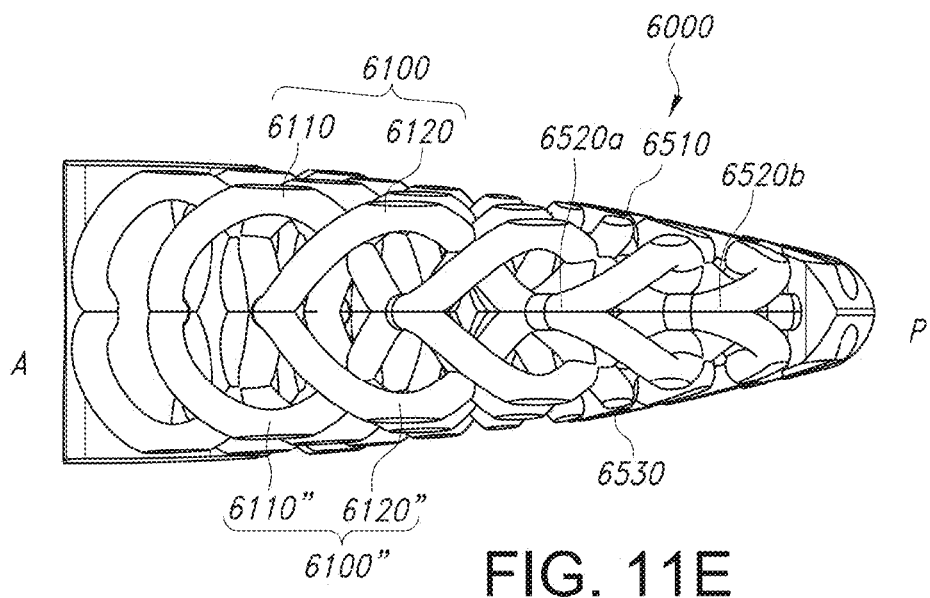

As shown in FIGS. 11A-11C, the implant may contain a large open space 6830 in the center of the implant. A portion or all of the large open space 6830 is optionally filled with a bone graft or bone graft substitute to facilitate bone growth. The implant 6000 also includes open spaces 6820*a*, 6820*b*, etc., collectively 6820, as well as open spaces 6810*a*, 6810*b*, etc., collectively 6810, formed inside and around the exterior coiled arc 6100. Any portion or all of the open spaces 6820, 6810, may optionally be filled with a bone graft or bone graft substitute to facilitate bone growth.

iv. Exemplary Implant Formed from Plurality of Interrupted Loops

In another embodiment, such as depicted in FIGS. 12A-12E, the implant contains a plurality of interrupted loops, such as in the form of a stack interrupted loops that form the side walls and substantially concentric loops that form the superior and inferior surfaces of the implant along with the inside of the implant. Optionally, the implant also contains one or more closed loop coils, typically as the interior coil or interior set or group of coils, optionally also as one or more intermediate coils, or intermediate sets or groups of coils.

The implants can have any suitable size and shape, which depends on the use for the implant. The implant contains a plurality of side walls, typically at least four side walls, optionally more than four side walls, a superior surface and an inferior surface. The interrupted loops typically contain more than one coil, in the form of a set of coils or a group of coils. In a preferred embodiment, each of the interrupted loop is a set of coils. The implant preferably contains more than one level of coils, where each level contains at least one and preferably more than one interrupted loop. In a preferred embodiment, each level contains a plurality of concentric interrupted loop where the exterior loop has the greatest dimensions (e.g. diameter) and the interior loop has the smallest dimensions. Any interior loop, if present, has a greater diameter than the interior loop, but a smaller diameter than the exterior loop, with diameters decreasing as the loops move towards the interior of the implant.

As depicted in FIGS. 12A-12E, the implant 7000 contains an anterior plate 7600 integrated with the cage and configured to facilitate insertion of the cage into a patient, and a posterior plate 7400, typically in the shape of a wedge with a rounded end. In these figures, the exemplary implant contains two levels (7710 and 7720) of concentric sets of interrupted loops, where each level contains two sets of interrupted loops (7810 and 7820 in the upper level 7710 and 7810' and 7820' in the lower level 7720), and each set contains two congruent coils (7812 and 7814 collectively forming an exterior set of interrupted loops 7810, and 7822 and 7824 collectively forming an interior set of interrupted loops 7820), a superior surface 7850, and an inferior surface 7830. The implant has an anterior end 7200 and a posterior end 7300. The implants may have a different height at the anterior end 7200 and the posterior end 7300. Typically, the shape of the implant changes with the changes in the diameter the diameter D of the coils.

a. Set of Coils in the Form of Closed Loops and/or Interrupted Loops

Figure 13A:
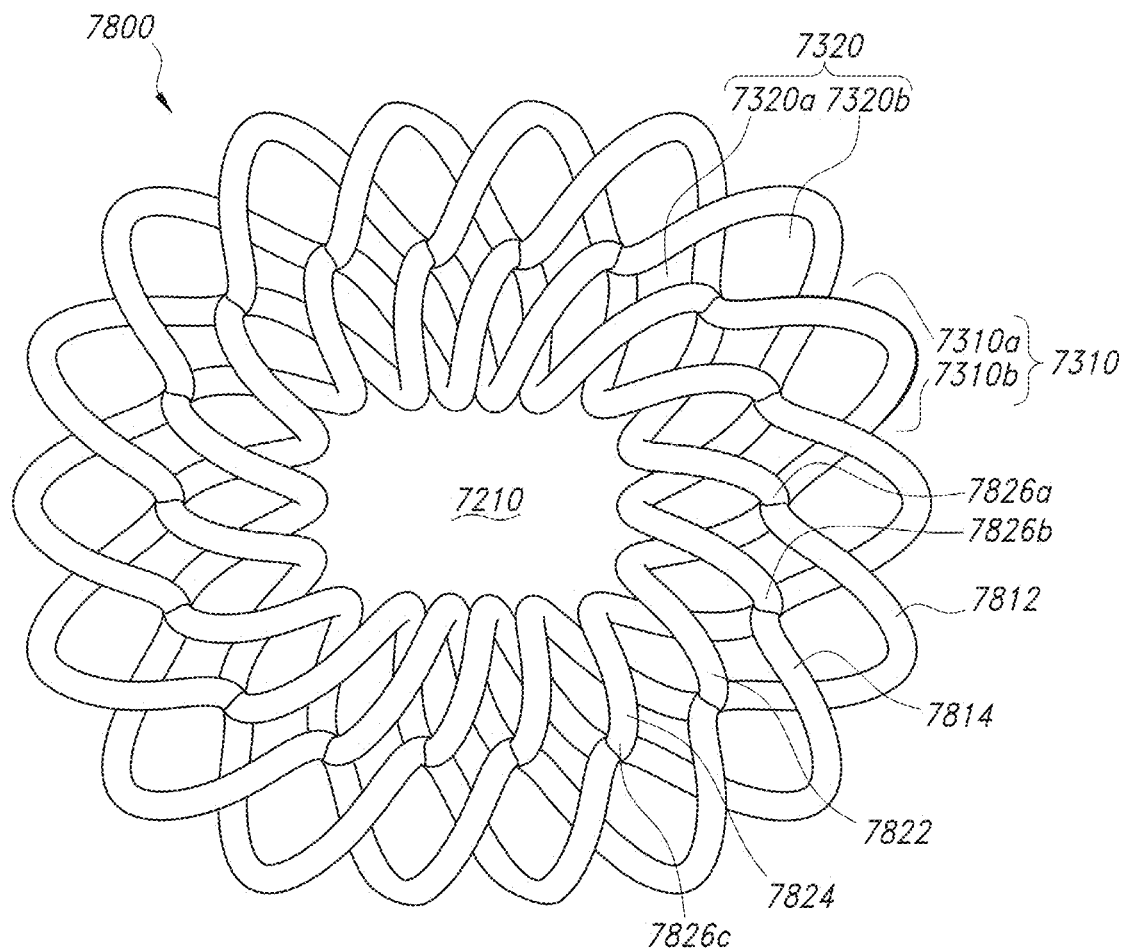
FIGS. 13A and 13B are two views of the closed loops in a single level of the implant depicted in FIGS. 12A-12E, without the plates. No plates are included in these views, thus, closed loops (not coiled segments) are depicted in these figures.
Figure 13B:
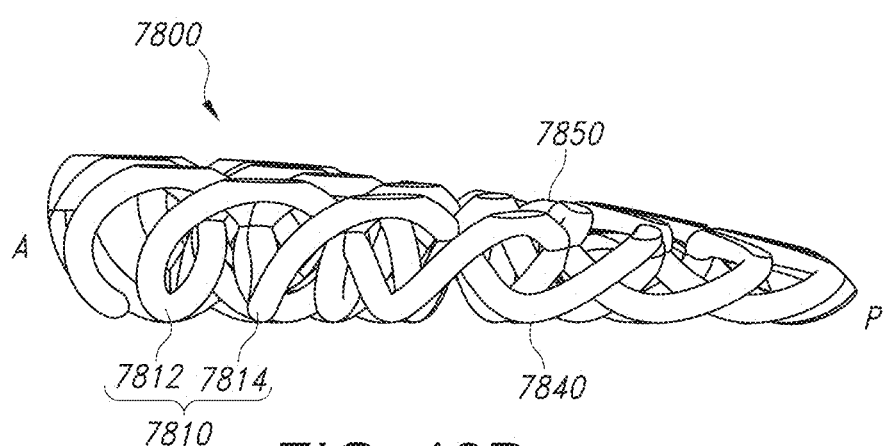

Two sets of coils. 7810 and 7820, collectively forming the level 7710, in the form of a continuous closed loop, are shown in FIGS. 13A and 13B for ease of viewing. As shown in FIGS. 13A and 13B, the set of coils 7810 contains two congruent coils 7812 and 7814, and the set of coils 7820 contains two congruent coils 7822 and 7824. The number of coils in each set is merely for illustrative purposes, and one of skill in the art would understand that each set can have the same number of congruent coils or different numbers of congruent coils. Additionally the number of congruent coils in each set can vary as needed, such as at least 1, 2, 3, 4, 5, 6, 7, 8, 9, or, 10 or more congruent coils in each set. Other amounts, such as 15 or more, 20 or more, or even greater numbers of congruent coils in each set are also envisioned.

Figure 12A:
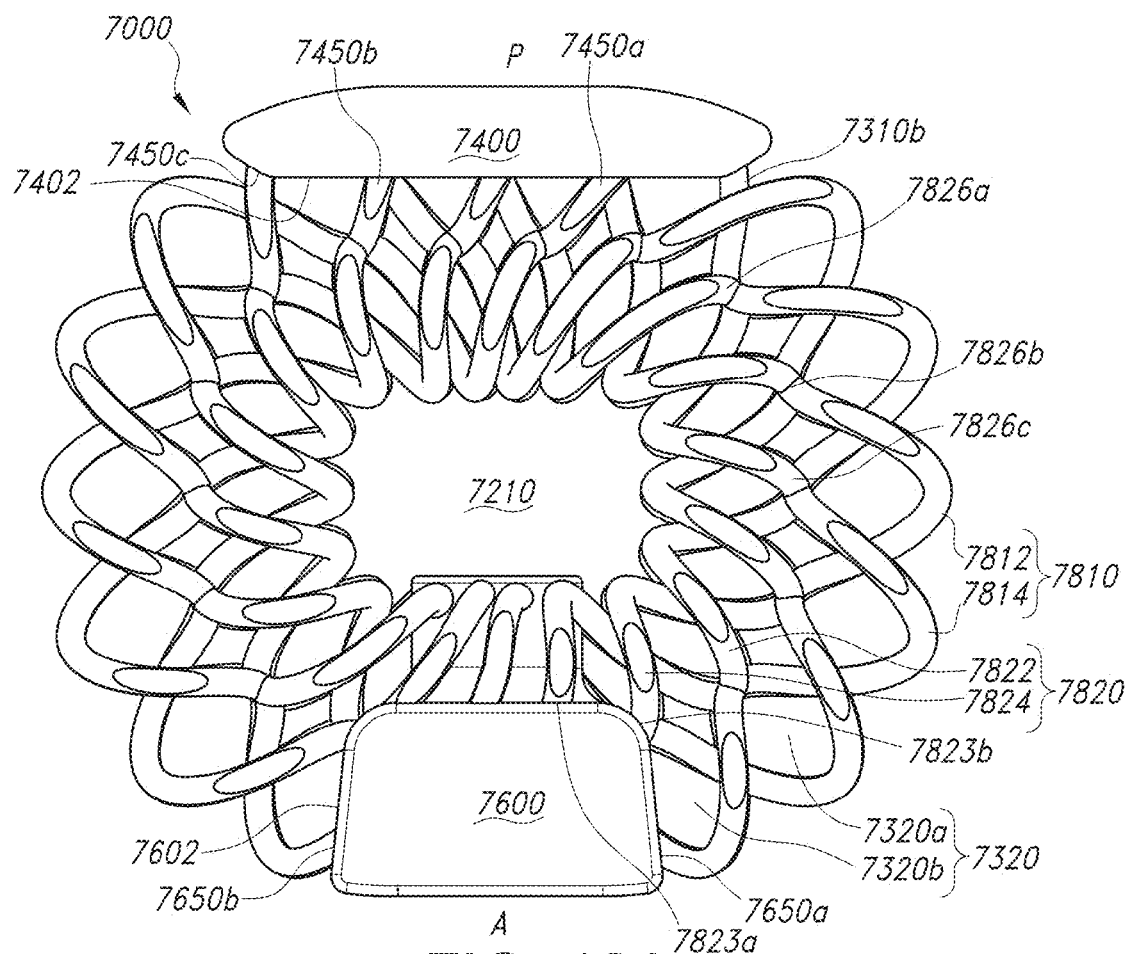
FIGS. 12A-12E are five views of an exemplary implant for use as an anterior cervical and/or anterior lumbar interbody fusion (ALIF) spinal fusion device. The exemplary implant contains an anterior plate integrated with the cage and configured to facilitate insertion of the cage into a patient, and a posterior plate, typically in the shape of a wedge with a rounded end. In these figures, the exemplary implant contains two levels of concentric sets coils, where each level contains two sets of coils, and each set contains two congruent coils. The implant has plane of symmetry in the transverse plane T, such that one level is the symmetrical opposite of the other level along the transverse plane T of the implant.
Figure 12B:
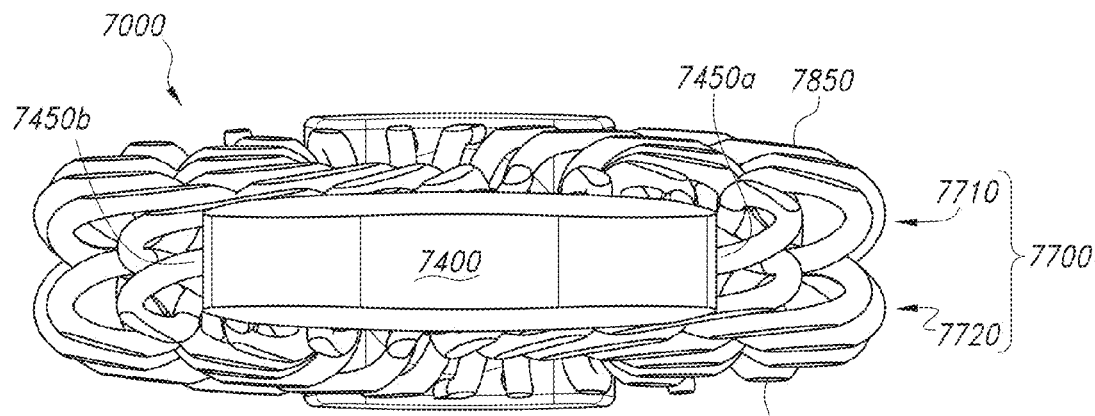

The curvature for a single closed loop can be seen in the side view (FIG. 13B). In some embodiments, each set of coils may have a profile that generally corresponds with the convexity or concavity of the surface inside the body that will be adjacent to the superior or inferior surface of the implant. In the current example, the sets of coils are formed of coils with varying diameter D, so that the coils at the anterior end 7200' of the implant have a larger diameter than the coils at the posterior end 7300' of the implant, with the implant tapering in diameter from the anterior end to the posterior end. The greatest diameter D may be up to 13 mm, up to 9 mm, up to 8 mm, up to 7 mm, up to 6 mm, preferably 5 mm, and the smallest diameter (D) in a given coil is smaller than the largest diameter for the coil, and preferably ranges from 0.7 mm to 4 mm, or about 1 mm, more preferably 2 mm. For example, as depicted in FIG. 12E, the implant may have a wedge shape. This shape is particularly useful for spinal fusion implants.

In some embodiments, the superior or inferior surfaces of the implant have a profile that corresponds with the convexity or the concavity of the adjacent surface in the body. For example, the one or more sets of coils in the superior or inferior surface of the implant, may have a modified shape, such that the superior surface of the implant is flatter than the regular coil, and generally corresponds with an adjacent concave surface, such as the end of a vertebral body. In FIGS. 12A-12E this is demonstrated by the superior surface 7850 and the inferior surface 7830 of the implant 7000.

b. Levels of Concentric Coils

The implant may have any suitable number of levels, and each level may contain any suitable number of concentric loops of coils. Suitable numbers of levels range from 2 to 1000 or even more, depending on the radius of the loops and the overall size of the implant. Typically for spinal implants, the number of levels ranges from 2 to about 30, preferably from 2 to 20, or 2 to 10.

Only one level 7800 of concentric coils (or concentric sets of coils) is depicted in FIGS. 13A and 13B for ease of viewing. As shown in these figures, the level is formed from two sets 7810 and 7820 of coils, where each set of coils contains two congruent coils, e.g. coils 7812 and 7814 in a first set 7810, and coils 7822 and 7824 in a second set 7820. The number of sets of coils in each level is merely for illustrative purposes, and one of skill in the art would understand that each level can have the same number of concentric coils or different numbers of concentric coils. The number of concentric coils in each level can vary as needed. For example, each level can contain at least 1, 2, 3, 4, 5, 6, 7, 8, 9, or, 10 or more concentric coils. Other amounts, such as 15 or more, 20 or more, or even greater numbers of concentric coils in each level are also envisioned.

The superior surface 7850 and inferior surface 7840 are defined by the superior and inferior portions of the level 7800 of coils.

Coils in adjacent sets of coils within a given level or on adjacent levels intersect with each other at intersection regions. Optionally, the intersection regions are spaced at regular intervals, i.e. the same angle within the rotation of the coil 7810. As shown in FIGS. 12A and 13A, coils 7812 and 7814 in the exterior set of coils 7810 intersect at regular intervals with the coils 7822 and 7824 in the adjacent interior set of coils 7820 at a plurality of intersection regions 7826a. 7826b, and 7826c.

c. Exemplary Implant Formed of Sets of Closed Loops of Coils, the Outer Set of Loops Interrupted by One or More Plates.

Typically, an implant contains a plurality of levels of concentric coils and the superior portions of each of the interior levels intersect with the inferior portion of the adjacent level of coils at regular intersection regions, as discussed above. As shown in FIGS. 12A-12E, the implant contains two levels 7710 and 7720 of concentric loops. The number of levels in the implant is merely for illustrative purposes, and one of skill in the art would understand that implants can be provided with a different number of levels. For example, the number of levels in an implant can be 2 or greater, such as 10 or greater, 15 or greater, 20 or greater, or up to 100 or up to 1000 levels.

In the implant depicted in FIGS. 12A-12E, the superior level 7710 is symmetrical with the inferior level 7720 about a transverse plane T.

The exterior set 7810 of coils in the superior level 7710 contains two congruent coils 7812 and 7814; similarly, the exterior set 7810' of coils in the inferior level 7720 contains two congruent coils 7812' and 7814'. The coils 7812 and 7814 in the exterior set 7810 of coils in the superior level 7710 connect with at regular intervals with the coils 7812' and 7814' of the exterior set of coils 7810' in the adjacent level. For example, the coils 7812 and 7814 in the exterior set of coils 7810 connect with the two coils 7812' and 7814' of the exterior set of coils 7810' at intersection regions 7520a, 7520b, and 7520c, located at the same relative location along each coil at regular intervals.

Similar intersection regions connect the coils 7822 and 7824 of the interior set 7820 of coils in the superior level 7710 with the coils of the interior set (not labeled on figures) in the second, inferior level 7720.

The exterior set of coils 7810 extends from the anterior plate 7600 in a curved manner towards the posterior plate 7400. At the posterior plate 7400, the congruent coils 7812 and 7814 of the exterior set of coils 7810 merge with the posterior plate 7400 at connection ends 7450a, 7450b. 7450c, etc., collectively designated as 7450. As shown in FIG. 12A, the connection ends merge with the posterior plate on the interior side (back) 7402 of the plate. The congruent coils 7812 and 7814 of the exterior set of coils 7810 merge with the anterior plate 7600 at connection ends 7650a. 7650b, etc., collectively designated as 7650. Similarly, the congruent coils 7822 and 7824 of the interior sect of coils 7820 merge with the anterior plate 7600 at connection ends 7823a, 7823b, etc.

As the coils extend from the anterior plate 7600 towards the posterior plate 7400, the diameter D of the coils decreases, reaching the smallest diameter at the posterior of the implant. The greatest diameter (D) may be up to 9 mm, up to 8 mm, up to 7 mm, up to 6 mm, preferably 5 mm, and the smallest diameter D in a given coil is smaller than the largest diameter for the coil, and preferably ranges from 1 mm to 4 mm, or about 1 mm, more preferably 2 mm.

Figure 12C:
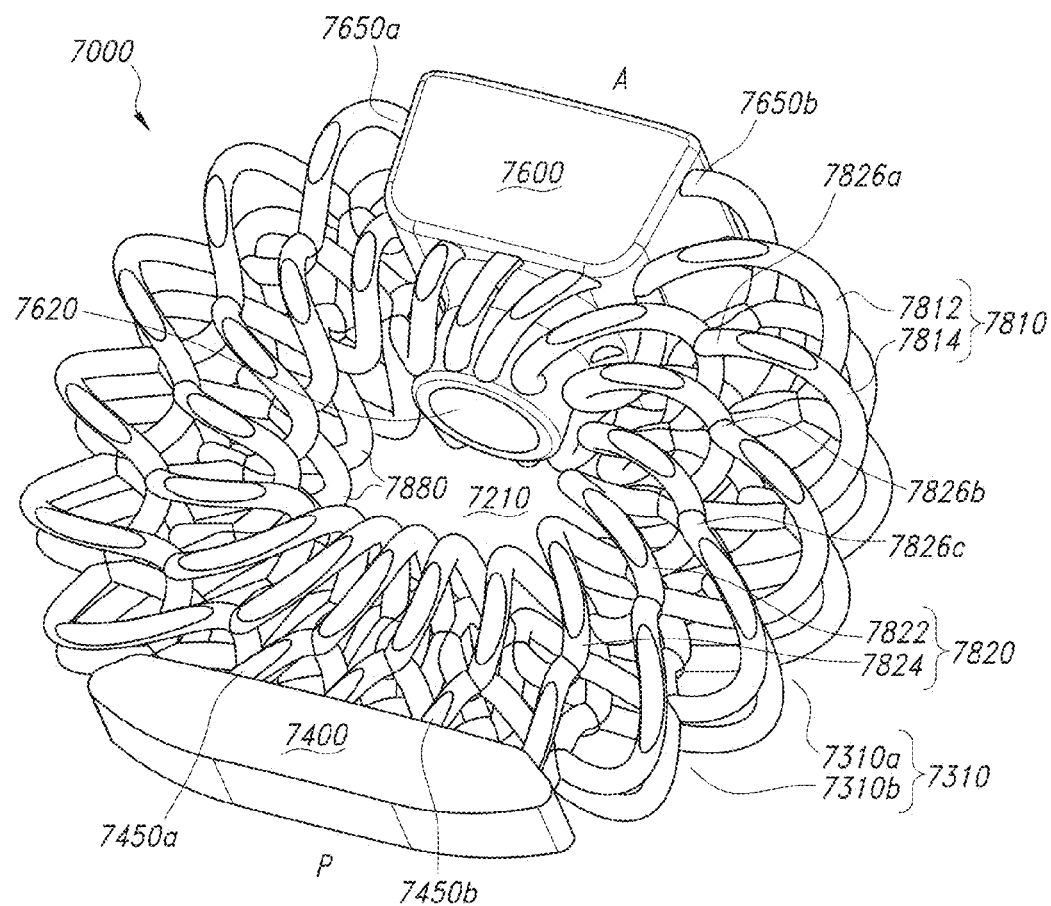
Figure 12D:
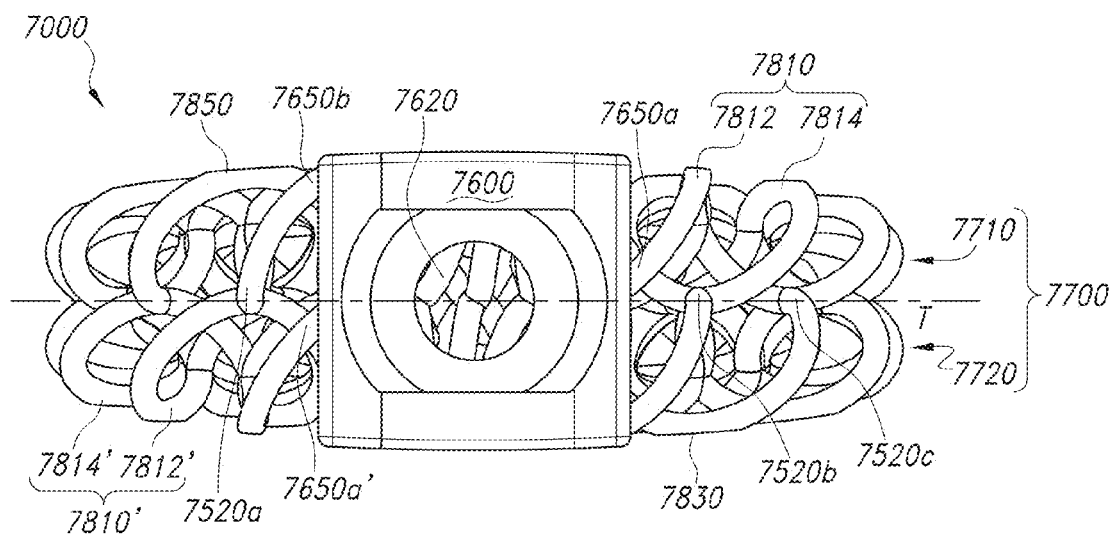
Figure 12E:
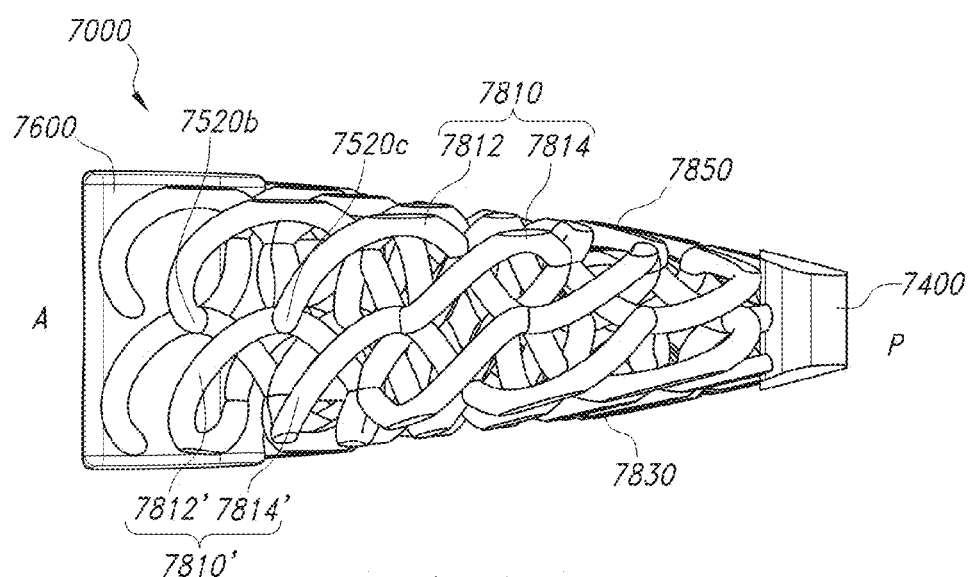

As shown in FIGS. 12A and 12C, the implant may contain a large open space 7210 in the center of the implant. A portion or all of the large open space 7210 is optionally filled with a bone graft or bone graft substitute to facilitate bone growth. The implant 7000 also includes open spaces 7320a, 7320b, etc., collectively 7320, as well as open spaces 7310a, 7310h, etc., collectively 7310, formed inside and around the exterior set of coils 7810. Any portion or all of the open spaces 7320, 7310, may optionally be filled with a bone graft or bone graft substitute to facilitate bone growth.

5. Plates for Insertion and/or Fixation

In some embodiments, the system or implant includes one or more plates configured to aid in insertion or fixation of the cage in the desired site in a patient's body. One or more plate(s) may be present at any location in the implant. Typically, plates merge with the ends of coils, sides of coils, or both.

An end (also referred to herein as a "connection end") of a coil or set or group of coils may connect with any side or portion of the plate, such as the interior side (back) of the plate, the superior or inferior surface of the plate, or a lateral side surface of the plate. In some embodiments, an end of a coil or set or group of coils connects with an exterior side (front) of the plate.

In some embodiments, the plate is located on the anterior portion of the implant. In others, the plate(s) may be located substantially on a corner of the implant, such as when used to facilitate insertion of the implant. In yet other embodiments, the plate may be located on the posterior side or a portion thereof of the implant.

The plate(s) may be integral with the rest of the implant. In this embodiment, the plate and the rest of the implant are printed together via 3-D printing. Alternatively, they may be formed by other suitable methods. In alternative embodiments, the plate(s) are provided separate from the rest of the implant, but are attachable to the implant prior to insertion in the patient.

The plates may have one or more regions configured to receive and attach to an insertion tool to facilitate insertion of the implant into the patient's body desired location.

Alternatively, or additionally, the plates may contain one or more holes configured to receive a bone screw to aid in fixation at the desired site. The plate may contain one or more bores having a suitable diameter for the body of the head of the screw to fit inside the bore. Optionally, the holes in the fixation plate are configured to receive other fixation elements, such as fluted nails.

Additionally, one or more plates may be included in the implant to increase the strength of the implant, and/or facilitate insertion of the implant. For example, a plate may be included at the posterior end of an ALIF in a suitable shape, such as a wedge shape, to increase the distance between the vertebral bodies during insertion of the implant.

i. Exemplary Standalone Implant Containing a Plate with Holes for Fixation Elements An exemplary implant containing a plate is depicted in FIGS. 9A-9D. As shown in these figures, the implant 4000 contains an implant body or cage 4100 and a plate 4200, where the plate is located on the anterior portion of the cage. The plate replaces one of the four side walls described above with respect to implants that do not contain a front plate, such that the implant body contains three side walls (4160, 4170, and 4180) and superior (4190) and inferior surfaces (not shown) (see FIGS. 9A, B, and D).

The implant body 4100 is formed from six levels of concentric closed loops of coils 4110, 4120, 4130, 4140, 4150, and 4155, which connect at their anterior end with the plate 4200. For example, coil 4110 connects at connection ends 4112 and 4114 with the interior side 4202 of plate 4200 and coil 4120 connects at connection ends 4122 and 4124 with the interior side 4202 of plate 4200. The number of levels in the implant is merely for illustrative purposes, and one of skill in the art would understand that each implant can have a different number of levels. For example, the number of levels in an implant can be 2 or greater, such as 10 or greater, 15 or greater, 20 or greater, or up to 100 or up to 1000 levels.

The implant also contains a central opening 4310 configured to receive a bone graft or bone graft substitute. The central opening is also configured to support bone ingrowth.

The plate 4200 contains two holes (4210a and 4210b) configured to receive bone screws 4300a and 4300b. One of skill in the art would understand that the number of holes is merely illustrative and that other amounts of holes for bone screws or other fixation elements may be present on an implant's plate.

Figure 9A:
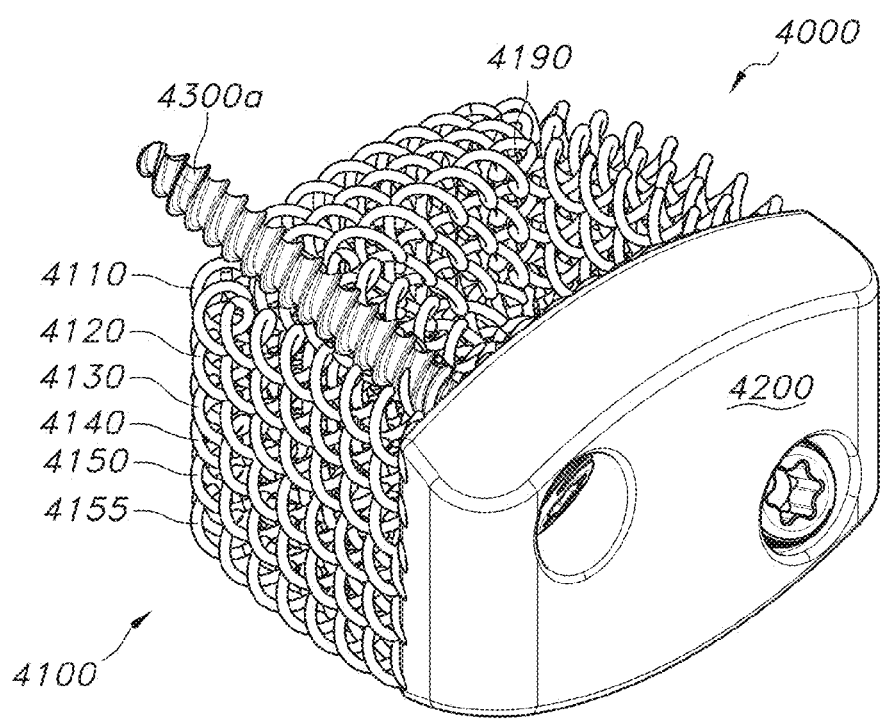
FIGS. 9A-9D are four views of an exemplary implant for use as a stand-alone anterior cervical and/or anterior lumbar interbody fusion (ALIF) spinal fusion device with a plate and screws for fixation to adjacent cranial and caudal vertebrae. In these figures, the exemplary implant contains six levels of coils, where each level contains three sets of coils, and each set contains two congruent coils.
Figure 9B:
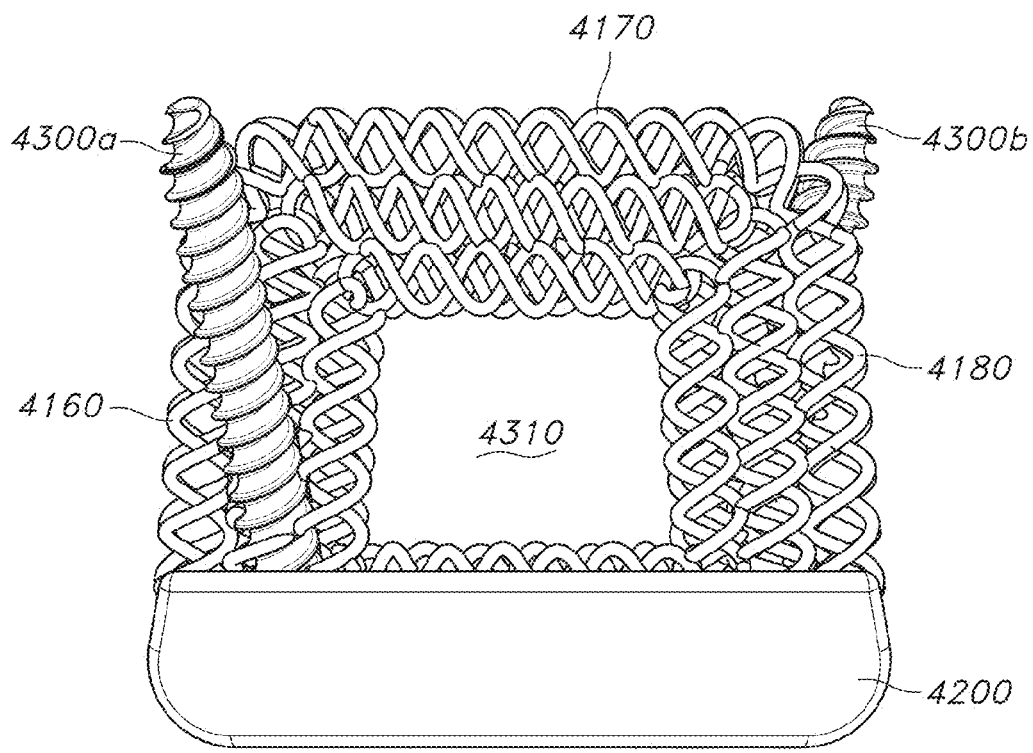
Figure 9C:
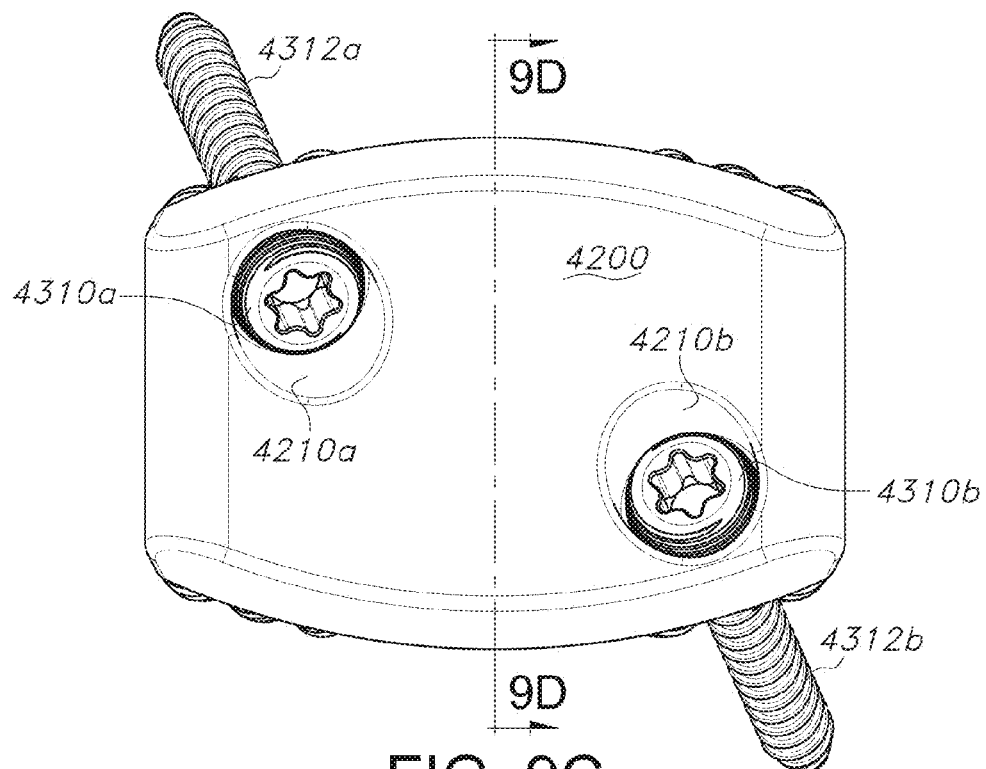
Figure 9D:
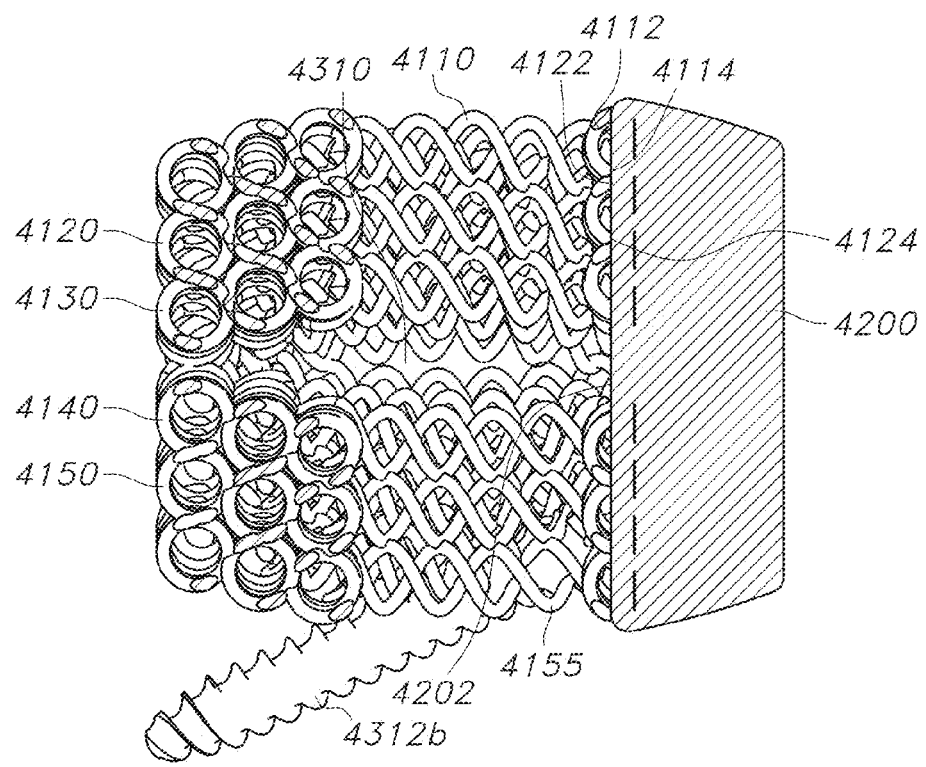

As shown in FIGS. 9A, 9B and 9C, when fully assembled, the screw head 4310a or 4310b sits in the hole in the plate. The hole is angled to guide the screw through the plate and over the superior or inferior surfaces of the implant body or cage, such that the body 4312a and 4312b of the screw does not contact or go through the implant body or cage.

ii. Exemplary Implant Containing Two Plates to Aid in Insertion

An exemplary implant containing two plates is depicted in FIGS. 10A-10D. As shown in these figures, the implant 5000 contains an implant body or cage 5100 and a two plates 5200a and 5200b, where one plate 5200a is located on a side wall 5190 and the other plate 5200b is located about a rounded corner 5300, where one side wall 5180 meets another side wall 5190.

The location of the corner plate is suitable for insertion into a patient's spine during an anterolateral procedure. The implant is particularly useful in cases where retraction on the bi-fortification of the vessels is not possible.

Each plate 5200a and 5200b contains one holes (5210a and 5210b, respectively) configured to receive an insertion tool. As shown in these figures, the holes are threaded to receive an insertion tool having complimentary threads. However, any suitable mechanism for receiving an insertion tool may be used in place of the threads. One of skill in the art would understand that the number of holes and shape of the holes, i.e. element for receiving and connecting with the insertion tool, is merely illustrative and that other amounts of holes or alternative shapes may be present on an implant's plate.

Figure 10A:
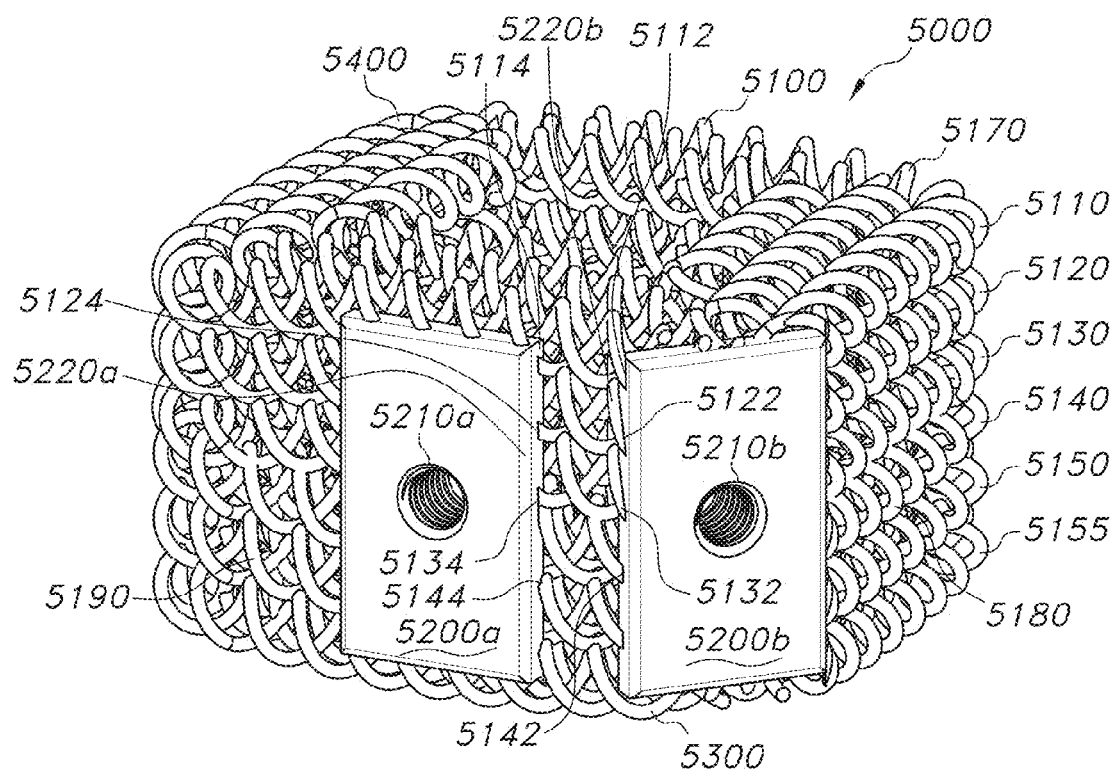
FIGS. 10A-10D are four views of an exemplary implant for use as an anterior cervical and/or anterior lumbar interbody fusion (ALIF) spinal fusion device. The exemplary implant contains two plates integrated with the cage to aid in insertion of the cage into a patient. In these figures, the exemplary implant contains six levels of coils, where each level contains three sets of coils, and each set contains two congruent coils.
Figure 10B:
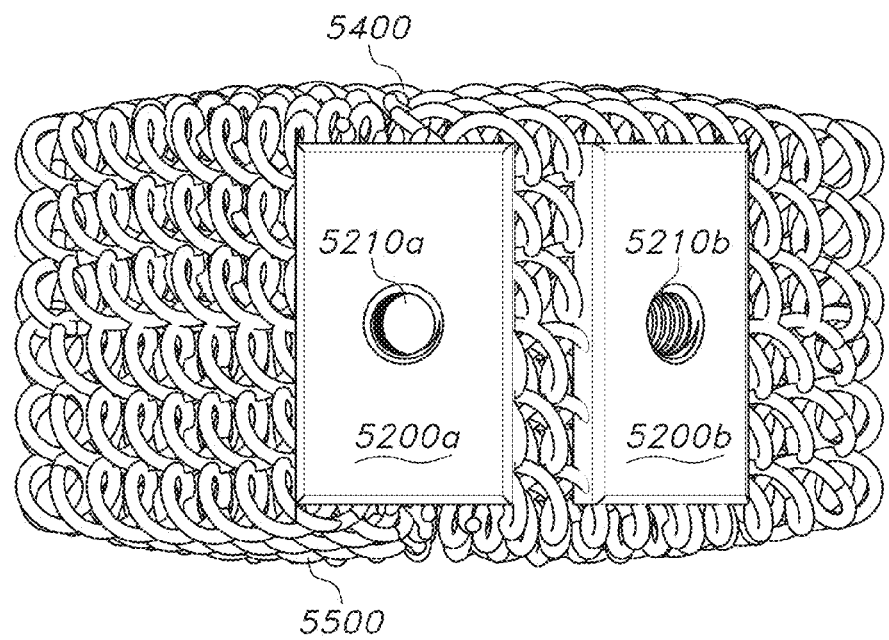
Figure 10C:
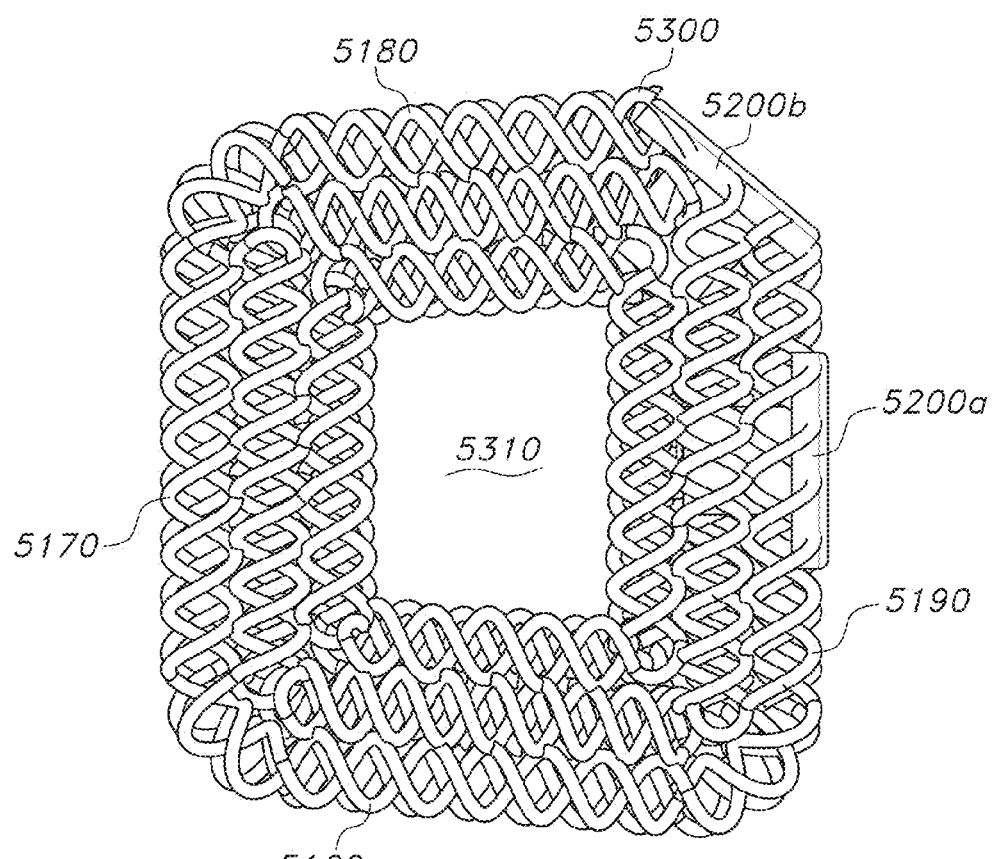
Figure 10D:
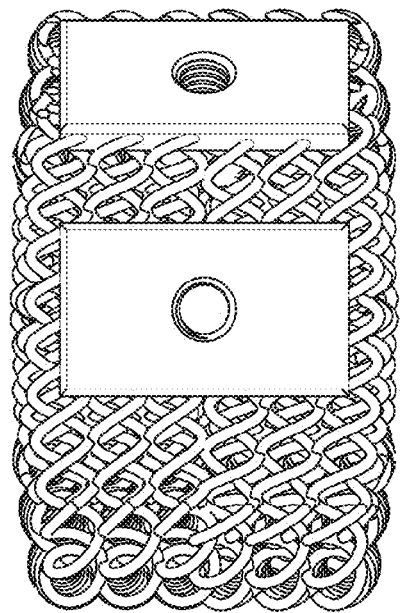

The implant body 5100 contains four side walls (5160, 5170, 5180, and 5190) and superior (5400) and inferior (5500) surfaces (see FIGS. 10A, B, and C). The implant is formed from six levels of concentric closed loops of coils 5110, 5120, 5130, 5140, 5150, and 5155. The number of levels in the implant is merely for illustrative purposes, and one of skill in the art would understand that each implant can have a different number of levels. For example, the number of levels in an implant can be 2 or greater, such as 10 or greater, 15 or greater, 20 or greater, or up to 100 or up to 1000 levels.

The plates 5200a, 5200b are integral with the side wall in which they are located. The coils can connect with any portion of the plate, such as the interior side (back) of the plate, the exterior side (front) of the plate, the superior or inferior surface of the plate, or a lateral side surface of the plate. For example, side wall 5180 contains coils 5110, 5120, 5130, 5140, 5150, and 5155. Each of these coils contains at least a first connection end 5112, 5122, 5132, and 5142, respectively, which connects with the plate 5200b on one of its lateral side surfaces 5220b. Similarly, side wall 5190 contains coils 5110, 5120, 5130, 5140, 5150, and 5155. Each of these coils contains at least a second connection end 5114, 5124, 5134, and 5144, respectively, which connects with the plate 5200a on one of its lateral side surfaces 5220a.

The implant also contains a central opening 5310 configured to receive a bone graft or bone graft substitute. The central opening is also configured to support bone ingrowth.

6. Exemplary Implants Formed from Plurality of Coiled Segments

In other embodiments, such as depicted in FIGS. 14A-14I and FIGS. 15A-15C, the implant contains a plurality of coiled segments that intersect with each other. The implant contains one or more outer walls, which defines the sides of the implant, a superior surface and an inferior surface.

Preferably, the outer wall is substantially smooth or includes substantially smooth portions. Preferably the sides of the implant are defined by a substantially smooth outer wall, such as in the form of a ring, optionally including an anterior end and a posterior end, which correspond with the anterior end and posterior end, respectively, of the implant.

At least a portion of the superior and inferior surfaces of the coiled segments form the superior and inferior surfaces, respectively, of the implant.

Preferably, the implant also contains a central support portion. Optionally, one or more of the interior coils intersects with the central support portion.

The implants can have any suitable size and shape, which depends on the use for the implant. In some preferred embodiments, the implant is a spacer for an interbody fusion, such as a spacer in the thoracic, cervical or lumbar region of the spine. In some embodiments, the spacer is an anterior lumbar interbody fusion (ALIF).

The sides of the implant may include one or more plates, wherein the one or more plates are integral with the outer wall(s) of the implant. Optionally, one of the plates serves as one of the walls of the implant and is connected at its sides with two other side walls of the implant.

In some embodiments, the implant contains an implant body that is defined by an outer side wall, in the form of a peripheral ring that contains an anterior plate at the anterior end of the implant and a posterior plate at the posterior end of the implant, and superior and inferior surfaces. The body of the implant contains plurality of coils, typically the coils are in the form of sets or groups of two or more coils, preferably sets of two coils. Preferably the implant has one or more planes of symmetry, such as the median plane M of the implant as a plane of symmetry and/or the transverse plane T as a plane of symmetry. In these embodiments, when the median plane M, which runs from the anterior end of the implant to the posterior end of the implant, is a plane of symmetry, one side of the implant relative to the median plane M is the symmetrical opposite (mirror image) of the other side. In embodiments in which the transverse plane T is a plane of symmetry, the superior half of the implant is the symmetrical opposite (mirror image) of the inferior half of the implant.

The implant may have any suitable number of levels, and each level may contain any suitable number of coils. Suitable numbers of levels range from 2 to 1000 or even more, depending on the radius of the coils and the overall size of the implant. Typically for spinal implants, the number of levels ranges from 2 to about 30, preferably from 2 to 20, or 2 to 10.

In some embodiments, the implant comprises a plurality of coils or sets of coils comprising at least two coils and an opening between and/or inside the coils, wherein the implant comprises one or more outer walls, a superior surface and an inferior surface, and a central support portion. The central support portion is inside the outer wall(s). The superior surface and inferior surface are formed from the plurality of coils or sets of coils. The outer wall is formed from the intersection of two or more exterior coils or sets of exterior coils. The outer side wall(s) is preferably in the form of a smooth peripheral ring.

Void Space in Implant

The implant contains open spaces, such as in the center of the implant, between and/or within the coils, and/or between the coils and the central support portion. A portion or all of the open spaces is optionally filled with a bone graft or bone graft substitute to facilitate bone growth.

The total volume of the open spaces within any particular implant is dependent on the overall dimension of the implant as well as the size and dimension of individual components within the implant including coils, anterior plate, posterior plate, central support portion (e.g. base, optionally with rings), and etc. The void volume typically ranges from about 20% to 80% of the volume of the implant. Optionally, the void volume of an implant is at least 20%, 25%, 30%, 35%, 40%, 45%, 50%, 55%, 60%, 65%, 70%, 75%, or 80% of the volume of the implant.

Preferably for an ALIF implant, the percent void volume is at least 40% of the total volume of the implant and at most 80% of the implant's total volume, preferably the void volume ranges from about 40% to 75%.

Sets of Coils

The implant preferably contains more than one level of coils, where each level contains at least one and preferably more than one sets of coils. In some embodiments, each set of coils contains two coils. One of skill in the art would understand that each set can have the same number of coils or different numbers of coils, depending on the particular implant and its proposed purpose. The number of coils in each set can vary as needed, such as at least 1, 2, 3, 4, 5, 6, 7, 8, 9, or 10 or more coils in each set. Other amounts, such as 15 or more, 20 or more, or even greater numbers of coils in each set are also envisioned.

In some embodiments, each set of coils has a profile that generally corresponds with the convexity or concavity of the surface inside the body that will be adjacent to the superior or inferior surface of the implant. For example, as depicted in FIGS. 14B and 14C the coils may have the profile of an ALIF implant. This shape is particularly useful for spinal fusion implants.

In some embodiments, only the superior or inferior surfaces have a profile that corresponds with the convexity or the concavity of the adjacent surface in the body. For example, the one or more sets of coils in a level, that forms the superior/inferior surface of the implant, may have a modified shape, such that the superior surface of the implant is flatter than a regular coil, referred to herein as a "flattened surface".

Coil Dimensions

The diameter (d) of the material that forms the coils in the implant can be the same for each coil or set or group of coils or vary between coils or sets or groups of coils. In some embodiments, the material that forms the coils in the sets of exterior coils has a greater diameter ($d_{ec}$) than the diameter of the material that forms the coils in the sets of interior coils ($d_{ic}$). In other embodiments, the material that forms the coils in the sets of exterior coils a smaller diameter ($d_{ec}$) than the diameter of the material that forms the coils in the sets of interior coils ($d_{ic}$). In still other embodiments, $d_{ec}$ and $d_{ic}$ are equal. Preferably the material that forms the coils in the sets of exterior coils has a diameter ($d_{ec}$) that is greater than or equal to the diameter of the material that forms the coils in the sets of interior coils ($d_{ic}$) ($d_{ec} \geq d_{ic}$), more preferably $d_{ec}$ is greater than $d_{ic}$.

Typically, the diameter of the material that forms the coils (d) in the implant ranges from about 0.7 mm to about 5.0 mm, preferably from about 1.5 mm to about 2.5 mm. However, coils with larger diameters for their cross sections may be used as well. In some embodiments, the diameter of the material that forms the coils ($d_{ec}$) in the sets of exterior coils is larger than the diameter of the material that forms the coils in the sets of interior coils ($d_{ic}$). The diameter of the material that forms the one or more rings ($d_{ring}$) of the central support portion can have a similar range to the diameters of the coils, such as from about 0.7 mm to about 5.0 mm, preferably from about 1.5 mm to about 2.5 mm, more preferably about 1.8 mm.

In some embodiments, one or more of the coils or sets of coils has a diameter (D) that varies over the length of the coil. Optionally, the diameter (D) is greatest at the anterior end of the implant and smallest at the posterior end. In other embodiments, the diameter (D) is greatest in the center of the implant and decreases moving from the center of the implant towards the anterior and the posterior ends of the implant.

i. Exterior Coils

Preferably, the first level in the implant contains two sets of exterior coils, a first set of exterior coils on the right side and a second set of exterior coils on the left side, relative to the median plane (M). The second level in the implant also contains two sets of exterior coils, a first set of exterior coils on the right side and a second set of exterior coils on the left side, relative to the median plane (M).

The convex surfaces of the first set of exterior coils in the first level and the convex surfaces of the first set of exterior coils in the second level intersect with each other to form one side of a peripheral ring 8550, which defines the outer wall of the implant. Similarly, the convex surfaces of the second set of exterior coils in the first level and the convex surfaces of the second set of exterior coils in the second level intersect with each other to form the opposite side of the peripheral ring 8550, which defines the outer wall of the implant.

The ends of the exterior coils terminate at the peripheral ring of the implant.

ii. Interior Coils

Preferably, the first level in the implant contains at two sets of interior coils, a first set of interior coils on the right side and a second set of interior coils on the left side, relative to the median plane (M). The second level in the implant also contains two sets of interior coils, a first set of interior coils on the right side and a second set of interior coils on the left side, relative to the median plane (M). The sets of interior coils are located between the central support and the sets of exterior coils.

The sets of interior coils intersect at a plurality of points with the sets of the exterior coils. One or more ends of the interior coils terminate at the outer wall of the implant or at the central support portion.

Optionally, the implant contains one or more coils, sets of coils and/or groups of coils between a set of interior coils and a set of exterior coils.

iii. Side Wall

The implant contains one or more side walls, which define the sides of the implant. Preferably, the side wall is substantially smooth or includes substantially smooth portions. Preferably the sides of the implant are defined by a substantially smooth side wall, such as in the form of a ring, optionally including an anterior end and a posterior end, which correspond with the anterior end and posterior end, respectively, of the implant.

In preferred embodiments, the outer wall contains two peripheral ring segments, the anterior plate and the posterior plate. The smooth peripheral ring offers further strength to the implant during impaction and helps distribute impaction forces. As the exterior sets of loops are expected to support most pressure load when resting on the apophyseal ring, the peripheral ring adds additional axial mechanical strength to the exterior sets of loops. Additionally, the smooth surface provided by the peripheral ring can minimize shearing nearby tissues when the implant is in contact with tissues at various stages of placement including the impaction stage.

The outer wall(s) of the implant may include one or more plates. In embodiments containing more than one outer wall, optionally, one of the plates defines one of the walls of the implant and is connected at its sides with two other walls of the implant. In some embodiments, the outer wall is in the form of a peripheral ring that contains an anterior plate at the anterior end of the implant and a posterior plate at the posterior end of the implant.

iv. Central Support Portion

In preferred embodiments, the implant also includes a central support portion, which provides support to the implant, particularly during insertion into a patient's body. The central support portion typically contains a base that connects two opposing sides of the implant, such as the anterior end and the posterior end or a portion of a side outer wall and the corresponding portion on the opposite side outer wall. Preferably the base of the central support portion lies along the median plane that connects the anterior end and the posterior end of the implant. Optionally the central support portion also contains one or more additional supports, such as one or more rings. The central support portion may contain one or more, such as two, three, four, five, six, seven, eight, nine, ten or greater amounts of, rings, which strengthen the connection between the base and the interior coils. The additional ring(s) provide support during impaction/insertion of the implant, and resistance to compression and/or shear force. Further the geometry of the rings, e.g. the smooth outer surfaces, provides a smooth perimeter during insertion for safety to adjacent tissue surfaces.

v. Particular Examples

As depicted in FIGS. 14A-14F and FIGS. 15A-15C, the implant 8000, 9000 contains an implant body that is defined by an outer wall, superior and inferior surfaces. The outer side wall is in the form of a peripheral ring 8550, 9550 that contains an anterior plate 8600 at the anterior end of the implant and a posterior plate 8400 at the posterior end of the implant. The peripheral ring 8550 runs alongside the outer convex surfaces of the sets of exterior coils.

The body of the implant 8000, 9000 contains plurality of coils, typically the coils are in the form of sets or groups of two or more coils, preferably sets of two coils.

Figure 14A:
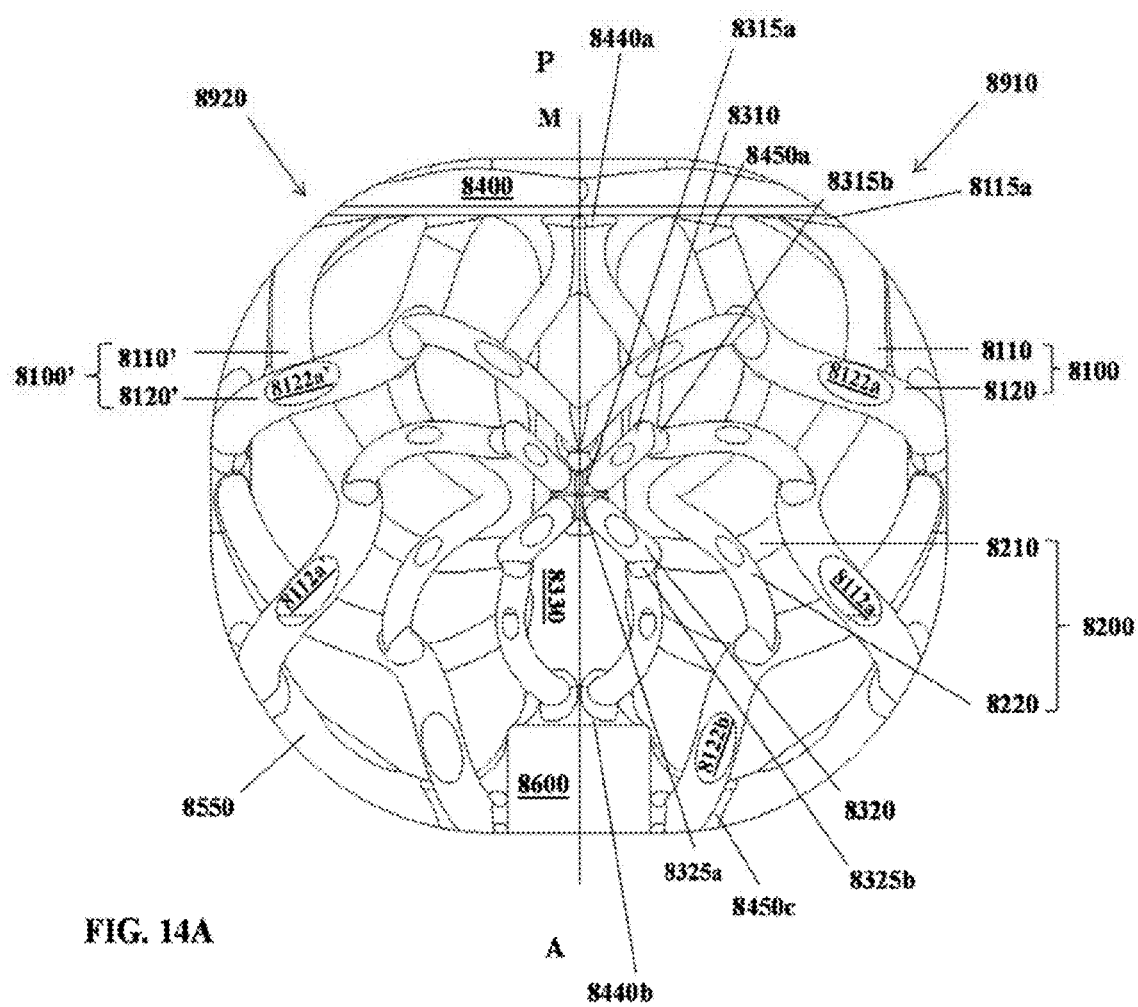
FIGS. 14A-14I are nine views of an exemplary implant for use as an anterior lumbar interbody fusion (ALIF) spinal fusion device.
Figure 14B:
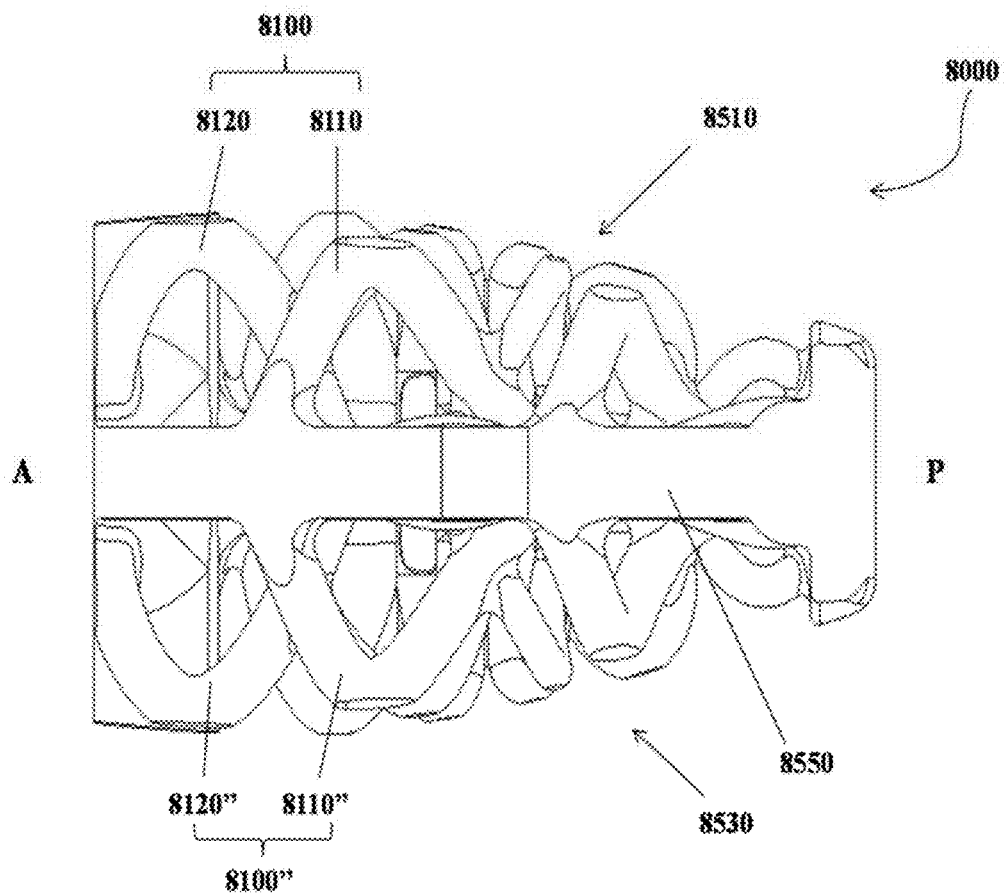
Figure 14C:
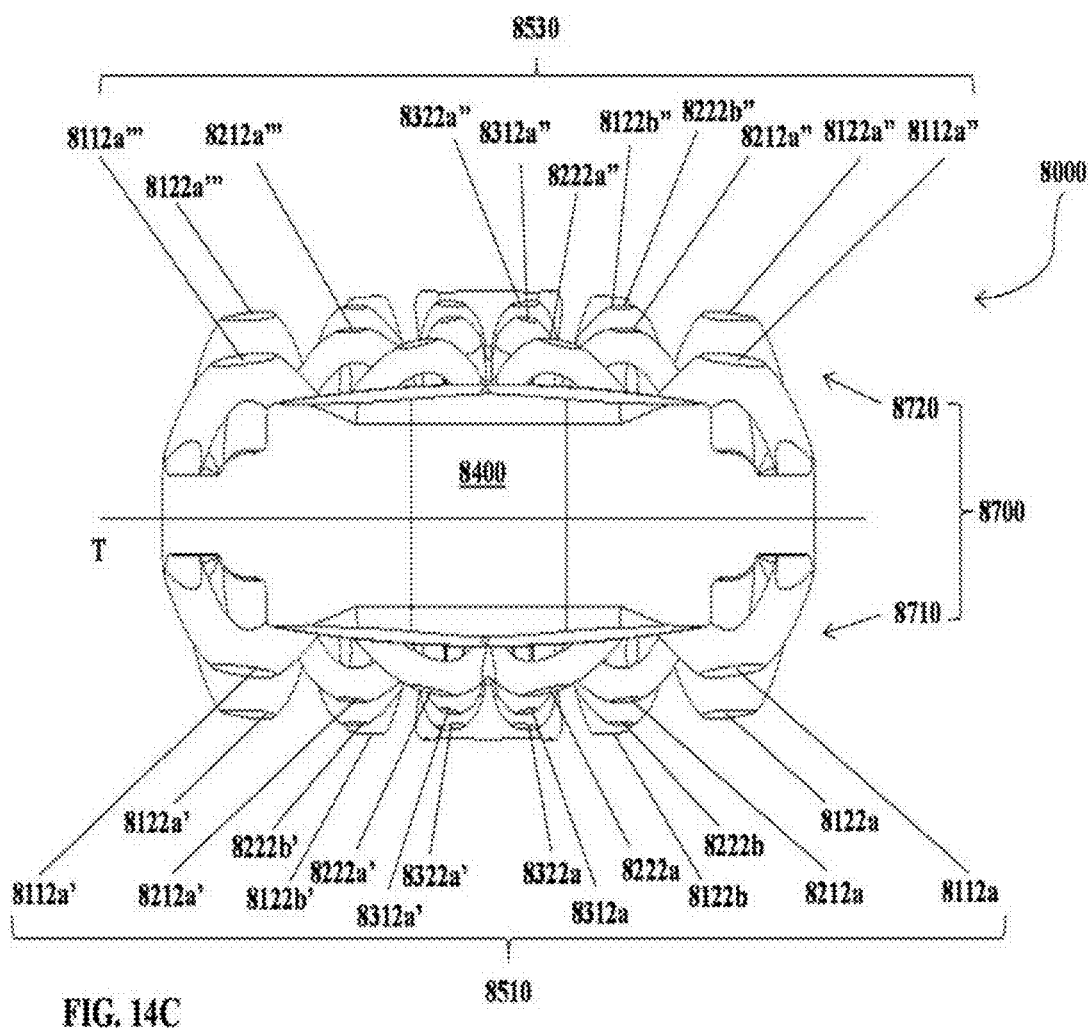
Figure 14D:
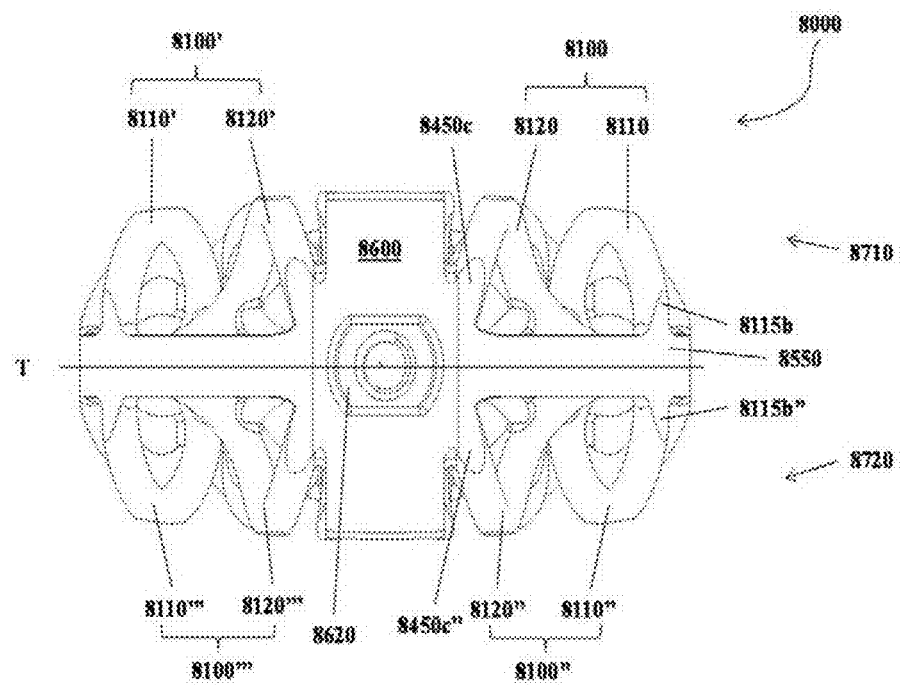

As depicted in FIGS. 14A-14F and FIGS. 15A-15C, the implant contains two sets of exterior coils, two sets of interior coils, and a central support portion. The sets of exterior coils 8100, 8100' are symmetrical opposites of each other, with the median plane M of the implant as a plane of symmetry (FIG. 14A). The implant has another plane of symmetry in the transverse plane T, such that a first level 8710 is the symmetrical opposite of a second level 8720 along the transverse plane T of the implant (FIGS. 14C and 14D). The coils in the sets of exterior coils and the sets of interior coils are substantially concentric within each set and form the superior and inferior surfaces of the implant along with central rings.

The central support portion 8300 contains a base 8330 spans the length of the implant connecting the anterior plate 8600 and the posterior plate 8400. The central support portion also contains additional supports, in the form of four rings 8310, 8320, 8310' and 8320'.

a. Exemplary ALIF

In one embodiment, such as depicted in FIGS. 14A-14I, the implant contains a plurality of coils in each level, in the form of two sets of exterior coils 8100, 8100' and two sets of interior coils 8200, 8200'. Each set of coils is formed from two coils. For example, a first exterior set 8100 of coils is formed of two exterior coils 8110 and 8120, a second interior set 8200 of coils is formed of two interior coils 8210 and 8220.

The implant further contains a central support portion 8300, which includes a base 8330 and support rings 8310, 8320, 8310', and 8320'.

In this embodiment, the implant is symmetric along the median plane M and along the transverse plane T. The implant contains two symmetric levels, the superior level 8710 and the inferior level 8720. Collectively, the levels of the implant are designated as 8700. The inferior level 8720 is a mirror image of the superior level 8710 along the transverse plane T of the implant. Therefore in the top view of the implant shown in FIG. 14A, only the superior level 8710 is visible.

Figure 14E:
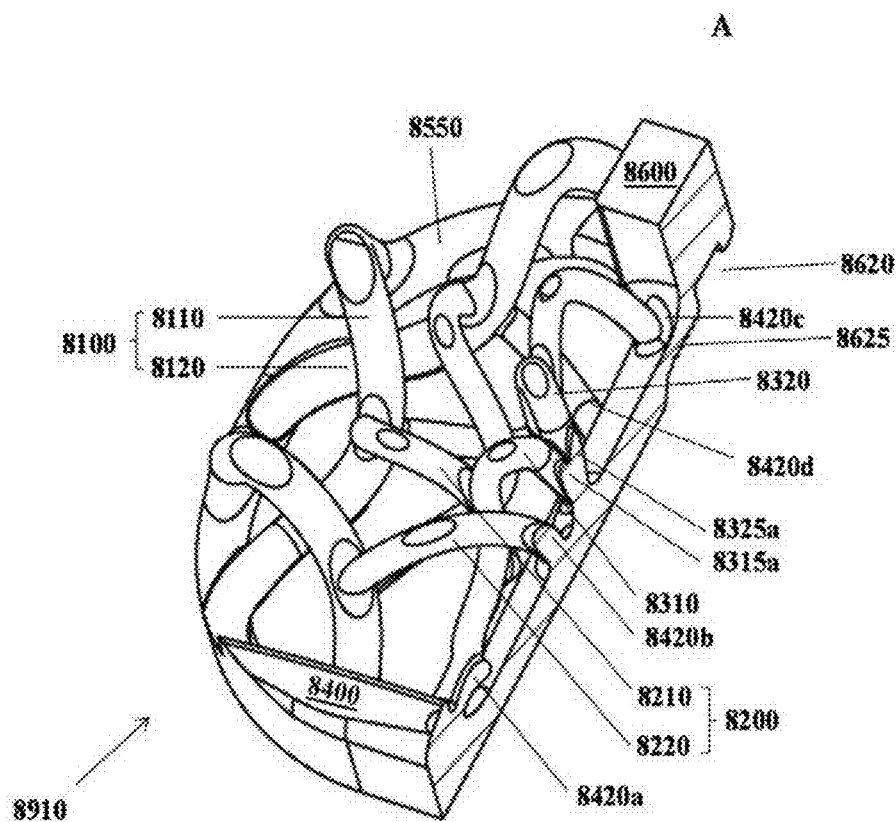

FIG. 14E illustrates one quarter of the implant, cut along the median plane M and the transverse plan T. i.e. one half 8910 of level 8710 cut along median plane M. The half 8910 of level 8710 contains two sets of intersecting coils formed of exterior set of coils 8100, and interior set of coils 8200, which are arranged in a concentric arrangement. In addition, one quarter of a central support portion 8300 lies along the median plane that connects the anterior plate 8600 and the posterior plate 8400. As shown in FIG. 14E, one half of a first support ring 8310 and one half of a second support ring 8320 intersect with the support base 8330 at intersecting region 8315a, 8325a.

A second half 8920 of level 8710 cut along median plane M is the symmetrical opposite (mirror image) of the first half 8910. The second half 8920 contains two sets, where one is an exterior set of coils 8100', and the other is an interior set of coils 8200', and one quarter of the central support, including a corresponding one quarter of the base and half of each of two support rings 8320' and 8310', each of which is a mirror image of the corresponding sets of coils and rings in the first half 8910.

Together, the coils and central support portion of both halves 8910 and 8920 form a first level 8710.

The outer wall of level 8710 is substantially smooth and generally corresponds with a first peripheral ring segment 8550 around the convex side of the exterior set of coils on one half 8910 and a second peripheral ring segment 8550' on the convex side of the exterior set of coils on second half 8920. Each of the two peripheral ring segments are joined to the anterior plate 8600 and the posterior plate 8400.

i. Sets of Coils

As show in FIGS. 14A-14F, each set of coils 8100, 8200, 8100', 8200', etc. contains two coils 8110 and 8120, 8210 and 8220, 8110' and 8120', and 8210' and 8220', respectively.

a. Exterior Coils

Superior level 8710, as shown in FIG. 14A, includes a first exterior set of coils 8100 which contains two exterior coils 8110 and 8120 and its mirror image, a second exterior set of coils 8100' which contains two exterior coils 8110' and 8120'. Similarly inferior level 8720, which is a mirror image along the transverse plane T of the implant of superior level 8710, includes a first exterior set of coils 8100" which contains two exterior coils 8110" and 8120" and its mirror image, a second exterior set of coils 8100''' which contains two exterior coils 8110''' and 8120'''.

b. Interior Coils

Superior level 8710 includes a first interior set of coils 8200 which contains two interior coils 8210 and 8220 and its mirror image, a second interior set of coils 8200' which contains two interior coils 8210' and 8220'. Similarly inferior level 8720, which is a mirror image along the transverse plane T of the superior level 8710, includes a first interior set of coils 8200" which contains two interior coils 8210" and 8220" and its mirror image, a second interior set of coils 8200''' which contains two interior coils 8210''' and 8220'''.

c. Flattened Surfaces of Coils

The superior and inferior surfaces of the implant can be of any shape that conforms to, i.e., mates with, the shape of the adjacent vertebral endplates when the implant is in a patient's body. This provides a secure and tight fitting of the implant in the intervertebral disc space.

In this embodiment, the coils 8110, 8120, 8210, 8220, 8110', 8120', 8210', and 8220', and support rings 8310, 8320, 8310', and 8320' contain flattened superior surfaces 8112a, etc., 8122a, 8122b, etc., 8212a, etc., 8222a, 8222b, etc., 8312a, etc., and 8322a, etc., which collectively form a flattened superior surface 8510 of the implant. Similarly, in the inferior level 8720, the coils 8110", 8120", 8210", 8220", 8110''', 8120''', 8210''', and 8220''', and support rings 8310, 8320, 8310', and 8320' contain flattened inferior surfaces 8112a", 8122a", 8122b", 8212a", 8222a", 8222b". 8222a", 8312a", etc., which collectively form a flattened inferior surface 8530 of the implant 8000 (See FIG. 14C).

d. Intersection Regions

Figure 14F:
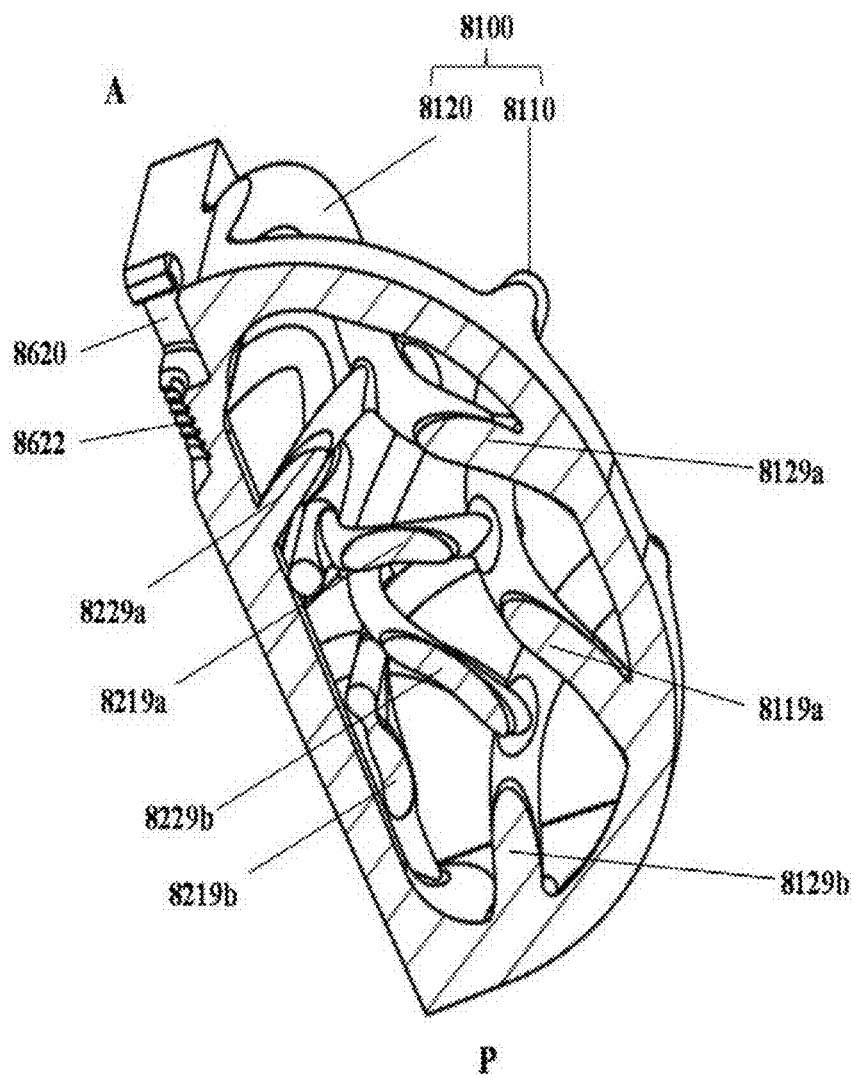
Figure 14G:
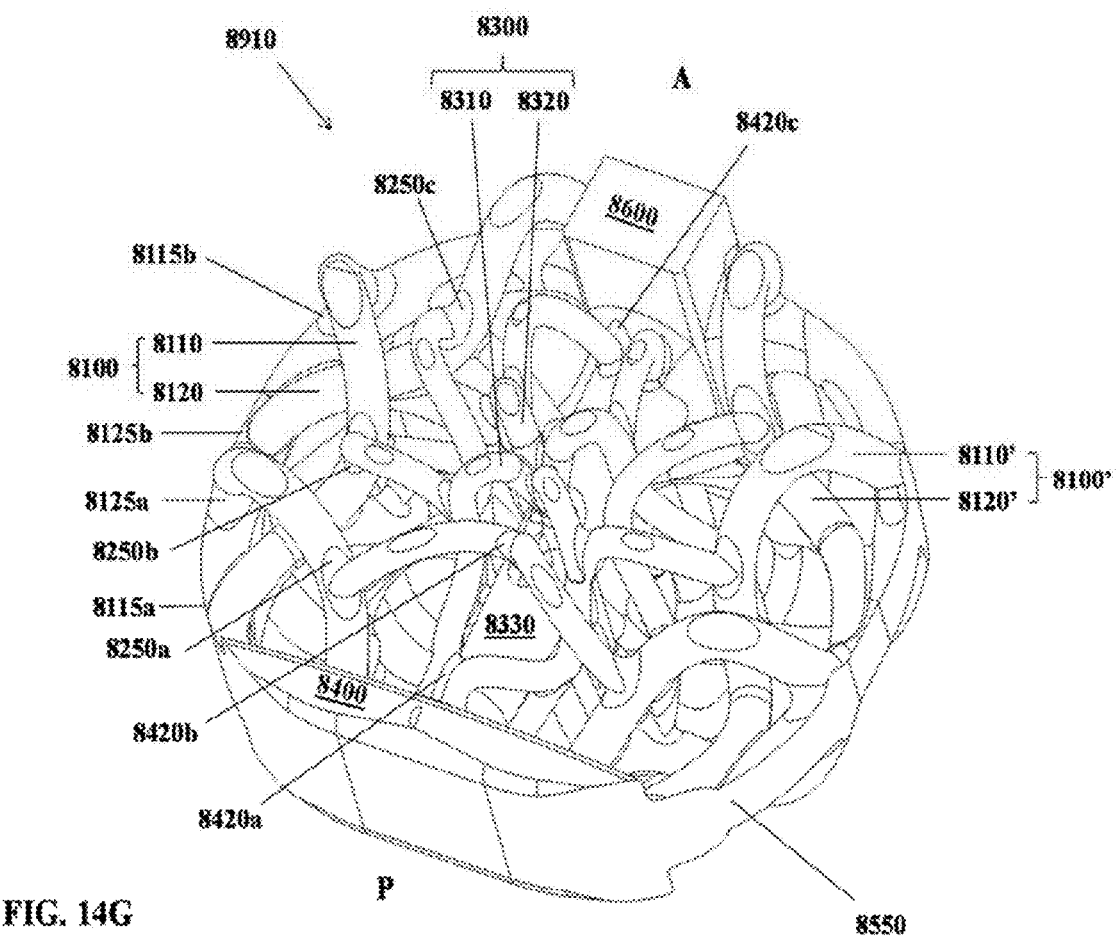
Figure 14H:
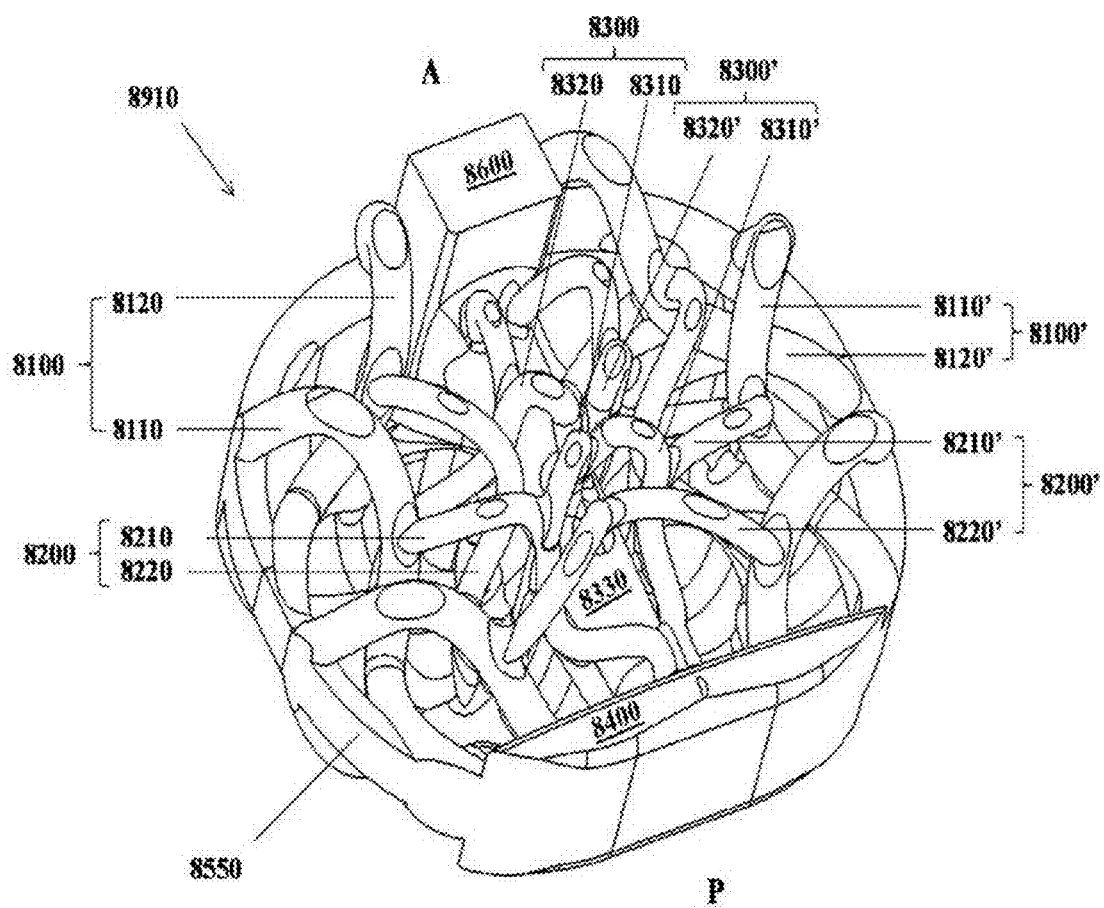

Coils in adjacent sets of coils within a given level intersect with each other at intersection regions. As shown in FIG. 14G, exterior coils 8110 and 8120 of the set of coils 8100 intersect with interior coils 8210 and 8220 of the set of coils 8200 in the same level 8710 at intersection regions 8250a, 8250b, and 8250c. The same intersection regions are present between the other sets of interior and exterior coils in levels 8710 and 8720.

Similarly, coils in adjacent levels intersect with each other at a plurality of intersection regions. As shown in FIG. 14F, the exterior coils 8110 and 8120 of the exterior set of coils 8100 in a first level 8710 intersect with the coils 8110" and 8120" of the coils 8100" in a second level 8720 (not shown in FIG. 14F) at intersection regions 8119a, 8129a, and 8129b.

The interior coils 8210 and 8220 of the interior set of coils 8200 in a first level 8710 intersect with the interior coils 8210" and 8220" of the interior set of coils 8200" in a second level 8720 at intersection regions 8219a, 8219b, 8229a, and 8229b.

ii. Outer Wall

As depicted in FIGS. 14A-14H, the implant 8000 contains an implant body that contains one or more outer walls, which define the sides of the implant. The outer wall is substantially smooth to prevent injury to adjacent tissues during insertion.

The outer wall contains a first peripheral ring segment 8550, which is located on the convex side of the exterior set of coils on one half 8910 of the implant and a second peripheral ring segment 8550' on the convex side of the exterior set of coils on second half 8920 of the implant. Each of the two peripheral ring segments connect with the anterior plate 8600 at one end and the posterior plate 8400 at the other end.

The peripheral ring segments 8550 and 8550' merge with the exterior sets of coils at a plurality of intersecting regions. For example, as shown in FIG. 14D, exterior coil 8110 of the exterior set of coils 8100 intersects with the peripheral ring segment 8550 at 8115a, and 8115b; the exterior coil 8120 of the exterior set of coils 8100 intersects with the peripheral ring segment 8550 at 8125a, 8125b, and 8450c. The same intersection regions are present between the other sets of interior and exterior coils in levels 8710 and 8720.

iii. Central Support

The implant also has a central support portion 8300 which include a base 8330 and one or more rings, which strengthen the connections between the base support and the interior sets of coils.

a. Base Support

The base support 8330 spans the length of the implant connecting the anterior plate 8600 and the posterior plate 8400. The base support intersects at a plurality of regions with the anterior plate, the posterior plate, the interior sets of coils, the central rings, and the perimeter ring.

b. Connecting Rings

Figure 14I:
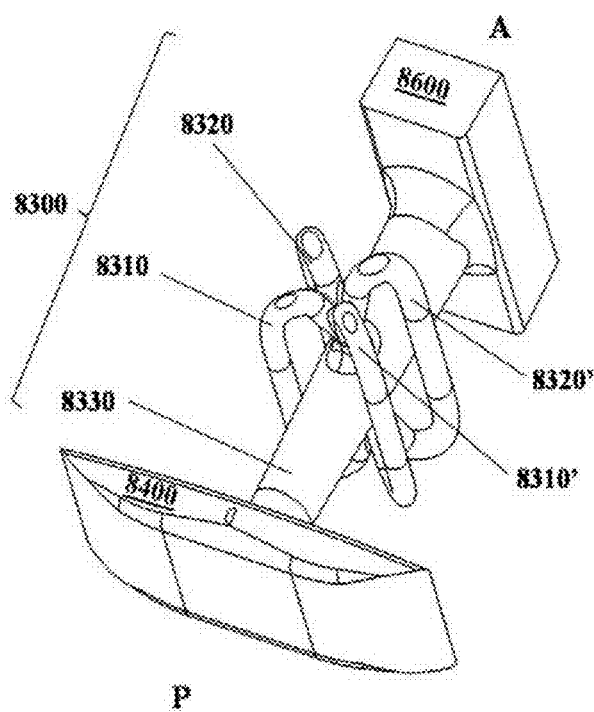

As shown in FIG. 14I, the central support portion contains four rings 8310, 8320, 8310' and 8320' or 9310, 9320, 9310' and 9320'. The rings traverse the depth of the implant, adopting an elongated shape. The rings traverse both the superior level 8710 and the inferior level 8720 of the implant. The rings optionally also include flattened surfaces such as 8312a. 8322a, etc. these flattened surfaces along with the flattened surfaces on the interior and exterior coils define the superior surface 8510 and inferior surface 8530 of the implant.

c. Intersecting Regions

The central support portion lies along the line of symmetry of the median plane M of the implant. One half of the central support portion is located in a first half 8910 of the implant; and its mirror image, the second half of the central support portion is located in a second half 8920 of the implant.

As shown in FIG. 14E, the anterior end of the interior coil 8210 of the set of coils 8200 intersects with the base 8330 at intersection region 8420c; the posterior end of the interior coil 8210 of the set of coils 8200 intersects with the base 8330 at intersection region 8420a and with its mirror image 8210' (not shown in FIG. 14E) along the median plane M of symmetry.

The anterior end of the interior coil 8220 of the set of coils 8200 intersects with the base 8330 at intersection region 8420d, and the posterior end of the interior coil 8220 of the set of coils 8200 intersects with the base 8330 at 8420b.

The same intersection regions are present between the other sets of interior coils and the base 8330 in levels 8710 and 8720.

iv. Anterior plate

The implant also includes an anterior plate 8600 and a posterior plate 8400. Viewed from the anterior end A of the implant, exterior sets of coils 8100, 8100' and the interior sets of coils 8200, 8200' generally extend in the direction from the anterior plate 8600 in a curved manner towards the plate end P of the implant. As the coils extend from the anterior plate 8600 towards the posterior plate 8400, the diameter (D) of the coils decreases, reaching the smallest diameter closest to the posterior P of the implant.

The diameter (D) for the coils also varies moving away from the center laterally to each side of the peripheral ring, where the diameter (D) of the interior set of coils is greater than the diameter (D) of the exterior set of coils.

Further, the diameter of the cross section of the coils (d) can vary between different coils or sets of coils. In the embodiment depicted in FIGS. 14A-14H, the cross section for the material forming the exterior sets of coils 8100, 8100' has a greater diameter (d) than the diameter (d) of the cross sections for the interior sets of coils 8200, 8200'.

As shown in FIG. 14A, none of the coils of the interior set or the exterior set of coils terminates at the anterior plate 8600. Although such intersections are envisioned, depending on the dimension of individual components, such as the size of the anterior plate, the diameter(s) (D1, and optionally D2, if the coil is not a circle) of the coils and the diameter of the cross section of the coil ($\alpha$, or d, for a circular cross section).

a. Insertion Region

The anterior plate 8600 preferably includes one or more insertion regions 8620 configured to receive a suitable insertion tool, which is used to insert the implant into the desired site between the adjacent vertebral bodies. In some embodiments, insertion region 8620 contains a threaded portion 8622, containing threads which mate with complimentary threads at an end of an insertion tool (see FIG. 14F). However, any suitable mechanism for receiving an insertion tool may be used in place of the threaded portion (e.g. friction fit). One of skill in the art would understand that the shape insertion region 8620, i.e. element for receiving and connecting with the insertion tool, is merely illustrative and that alternative shapes may be present on an implant to facilitate insertion. In some embodiments, insertion region 8620 is configured to receive a bone screw, and/or to attach a plate to allow for additional fixation. In yet other embodiments, more than one insertion region 8620 is present.

v. Posterior Plate

The implant includes a posterior plate 8400. At the posterior P of the implant, the coil 8120 of exterior sets of coils 8100 merges with the posterior plate 8400 at intersection regions 8450a. The exterior coil 8110 of exterior set of coils 8100 merges partially with the posterior plate 8400, and partially with the peripheral ring 8550 at intersection point 8115a. The interior coil 8210 of interior set of coils 8200 merges with the posterior plate 8400 at intersection point 8440a, additionally the coil 8210 of interior set of coils 8200 merges with its respective mirror image coil 8210' along the median plane M, at intersection point 8420a.

vi. Percent Void Spaces

As shown in FIGS. 14A-14H, the implant contains open spaces such as 8830a, 8830b, etc. A portion or all of the open spaces 8830a, 8830b, etc., is optionally filled with a bone graft or bone graft substitute to facilitate bone growth.

In the embodiment depicted in FIG. 14A, the percent void volume is about 75% of the total volume of the implant, and the structural components of the implant fill about 25% of the implant's total volume.

Variation

Figure 15A:
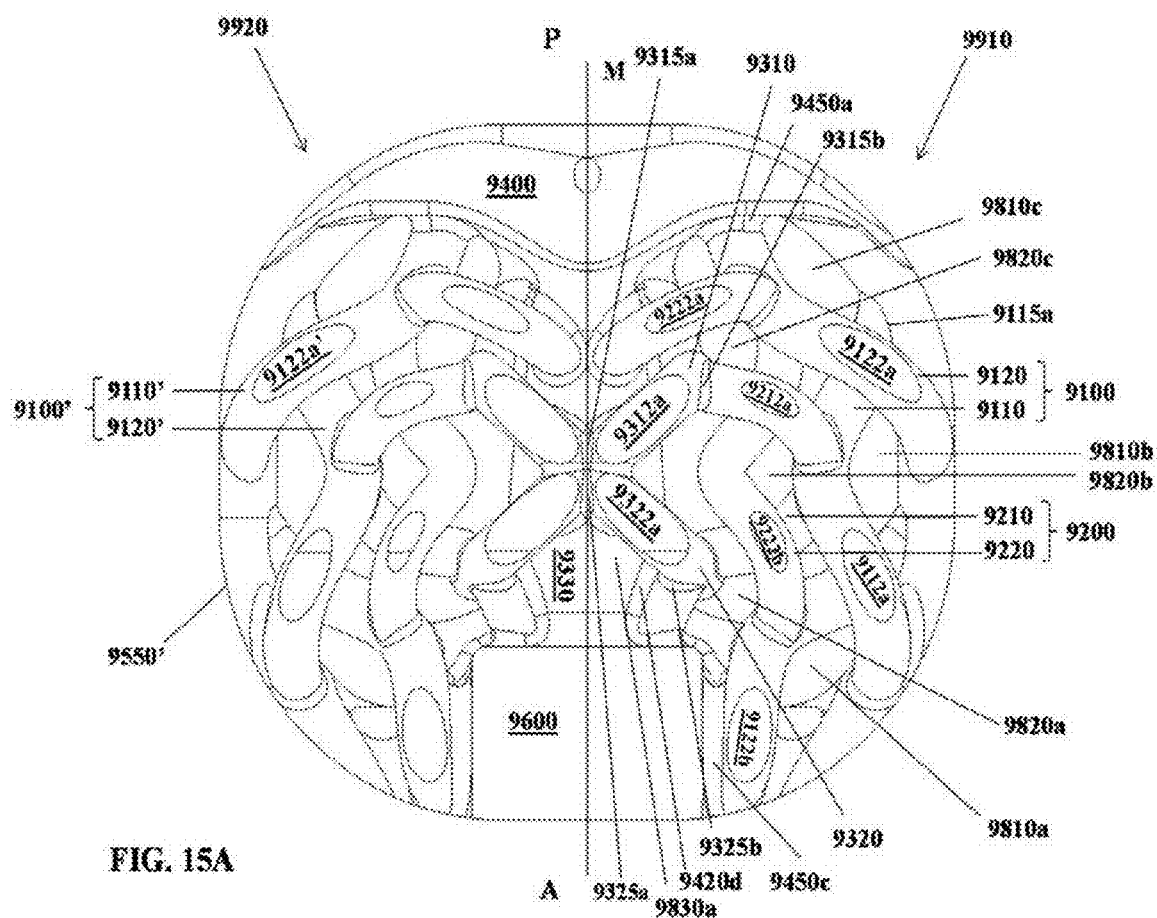
FIGS. 15A-15C are three views of an exemplary implant for use as an anterior lumbar interbody fusion (ALIF) spinal fusion device.
Figure 15B:
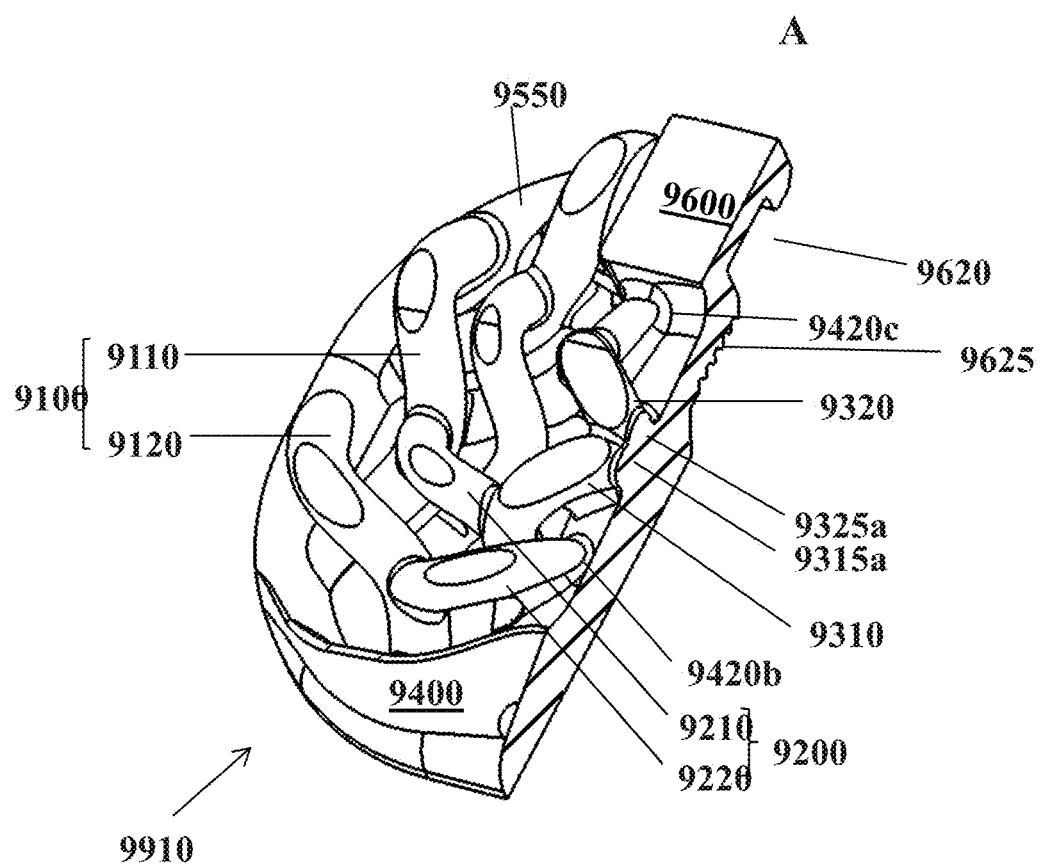
Figure 15C:
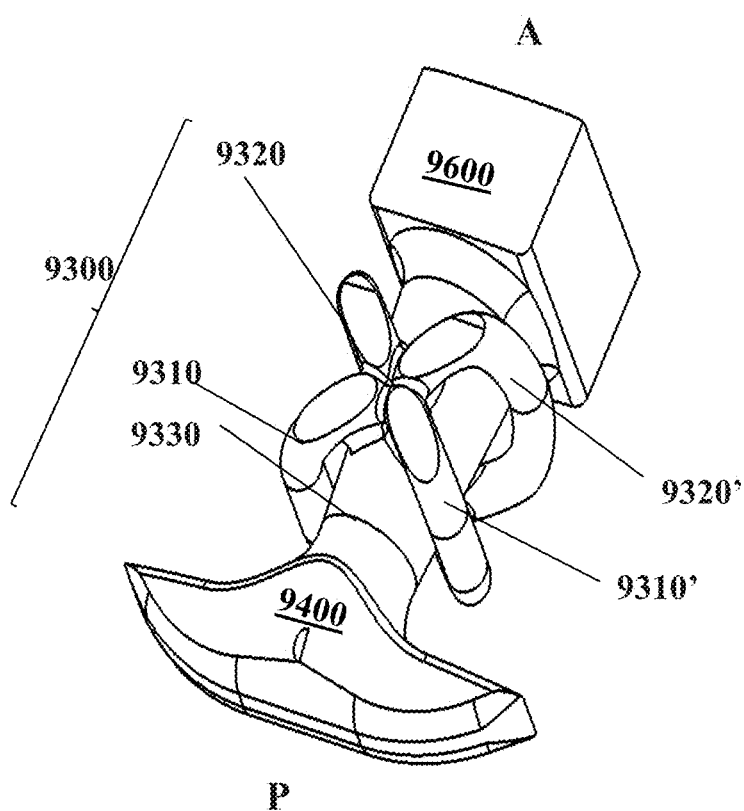

The implant depicted in FIGS. 14A-14I can be modified to fit into smaller or larger spaces, or spaces of various shapes. One example of such a modification is shown in FIGS. 15A-15C. The implants depicted in FIGS. 14A-14I and 15A-15C have the same general configuration, but differ in their overall size. Due to the size differences, the implants depicted in FIGS. 14A-14I and 15A-15C also differ in the thicknesses of their coils, the particular intersection regions of the coils, and the size and shape of the central support.

Preferred dimensions for these implants are about 36 mm and 23 mm, respectively, for the anterior-posterior depth (i.e. from the posterior plate to the anterior plate inclusive of these plates); about 42 mm and 26 mm, respectively, for the lateral width (i.e. the two furthest points on the opposing peripheral ring segments); and about 21 mm and 9 mm, respectively, for the height of the anterior plate or the height of the two levels of the stacked coils at the highest point.

For the implant depicted in FIGS. 14A-14H, preferred dimensions are about 36 mm for the anterior-posterior depth (i.e. from the posterior plate to the anterior plate inclusive of these plates), about 42 mm for the lateral width (i.e. two furthest points on the opposing peripheral ring segments), and about 21 mm in height (i.e. the height of the anterior plate or the height of the two levels of the stacked coils at the highest point).

The total volume of the open spaces within any particular implant is dependent on the overall dimension of the implant as well as the size and dimension of individual components within the implant including coils, rings, anterior plate, posterior plate, central support, etc.

In the embodiment depicted in FIG. 15A, the percent void volume is about 47% of the total volume of the implant, and the structural components of the implant fill about 53% of the implant's total volume.

The implants of FIGS. 14A-14I and 15A-15C also differ in that the coil 8210 of interior set of coils 8200 of FIGS. 14A-14I merges with its respective mirror image coil 8210' along the median plane M, at intersection point 8420*a*. In contrast, the interior coil 9210 of interior set of coils 9200 of FIGS. 15A-15C merges with its respective mirror image coil 9210' as well as the base 9330 of the central support portion along the median plane M, at intersection point 9219*b*.

The modifications shown in FIGS. 15A-15C are merely illustrative purposes, and one of skill in the art would understand that other suitable modifications can be made to form an implant for a different location in the body, or to form a larger or smaller intervertebral implant.

7. Openings in Implant

The implant contains open areas in the center of the coil(s), between coils in a set, group, and/or level, and optionally in the center region of the implant. A portion or all of the open area(s) is optionally filled with a bone graft or bone graft substitute to facilitate bone growth.

For the open areas inside a coil, a group of coils, or a set of coils, the size of open area is defined by the coil with the smallest diameter in the group or set.

As shown in FIGS. 3A and 3B, an open area 210 is located between the coils, 100, 100', 100", and 100"' and in the inside of the coils. A portion or all of the open area 210 can be filled with bone graft or bone graft substitute, optionally with one or more additional biologically active agents.

As shown in FIG. 7A, the implant may contain a large open space 2210 in the center of the implant. A portion or all of the large open space 2210 is optionally filled with a bone graft or bone graft substitute to facilitate bone growth.

In some embodiments, the large open space is separated into two or more smaller open spaces (not shown in Figures) by a divider, which may be formed of any suitable biocompatible material and may have any suitable shape. For example, the divider may be formed from one or more coils, such as from a plurality of coils in the form of a stack of coils.

C. Materials

The various components of the implant and implant system are fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$—$Al_4$—V ELI (ASTM F 136), or $Ti_6$—$Al_4$—V (ASTM F 1108 and ASTM F 1472)) and inert, biocompatible polymers, such as polyether ether ketone (PEEK) (e.g. PEEK-OPTIMA®, Invibio Inc). Optionally, the implant contains a radiopaque marker to facilitate visualization during imaging.

In some embodiments, the implant or system includes a wall or a portion thereof, through which the fixation elements are inserted or attached. This wall may be formed from a different material than the rest of the implant. For example, most of the implant may be formed from a first material, such as PEEK, while the wall or portion for attaching a bone screw or other fixation element is formed from a second, different material, such as titanium or another biocompatible material with a similar strength. Preferably, the wall is affixed to the rest of the implant in a permanent manner.

II. Systems and Kits

In some embodiments, multiple implants of different sizes may be constructed and delivered in a kit. A medical health professional may choose an implant (e.g., according to the needed size) during the surgery. In some embodiments, more than one implant may be inserted into the site in need of treatment in the patient's body.

Variations in implant heights, length and/or implant width are needed to accommodate the diversity in patients' anatomy. In preferred embodiments, kits are configured to provide a plurality of implants of various sizes. In some embodiments, the plurality of implants includes two to five implants of different sizes, in other embodiments the plurality of implants includes five to ten or more differently sized implants.

In some embodiments, the kits include tools for sizing the intervertebral disc space and selecting an implant of the right size and fit. These sizing tools include trial spacers of one or more sizes to facilitate selection of an appropriately sized implant. The trial spacer is typically inserted into the intervertebral space and removed therefrom prior to insertion of the implant.

A. Fixation Elements

Typically, the bone growth and/or repair system contains one or more implants and one or more fixation elements, such as fluted nails or bone screws. The one or more fixation elements may be placed through an end portion at each end of the implant.

One or more fixation elements are provided for insertion into and/or attachment to the implant. The fixation elements provide stabilization to the implant following implantation in the body. The fixation elements are attached to the implant in such a manner that they do not slip out of place following implantation, absent surgery or another method of intentional removal of the fixation elements.

Following insertion into a patient, and optionally deployment, the fixation elements anchor the implant into adjacent bone.

B. Bone Graft or Bone Graft Substitute

A bone graft or bone graft substitute is often needed to create the appropriate environment for bone growth. For example, in spinal fusion, a bone graft or bone graft substitute is generally needed for a solid bone bridge to form between the vertebrae.

A variety of materials may serve as bone grafts or bone graft substitutes, including autografts (harvested from the iliac crest of the patient's body), allografts, demineralized bone matrix, and various synthetic materials.

Autograft is the gold standard in spinal fusion because it has all of the characteristics necessary for a solid bridge of bone to grow. It provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient. However, limited supply of a patient's own bone, the risk of donor site pain and morbidity (blood loss, infection) in combination with long hospital stays and operation time, make autograft a less attractive option than bone graft substitutes.

The synthetic materials include calcium phosphates or hydroxyapatites, stem cell containing products which combine stem cells with one of the other classes of bone graft substitutes, and as the latest generation of bone graft substitutes, growth factor containing matrices such as INFUSE® (rhBMP-2-containing bone graft) from Medtronic, Inc.

C. Methods of Making Implants

The implant, components thereof, and/or implant system can be manufactured via various methods. For example, the coils in the implant and or the entire implant may be manufactured and assembled via injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations.

In some embodiments, multiple parts of the implant may be cast or injection molded and joined together (e.g., through welding, melting, etc.). In some embodiments, individual coils that form the implant may be generated separately (e.g., by casting, injection molding, etc.) and welded together to form the implants described herein.

Optionally, one or more portions of the implant are printed via 3-D printing to contain a textured or porous surface. In some embodiments, the superior and inferior surfaces, any interior surfaces including on the supports and the interior walls may be 3D printed with textured or porous surfaces. In further embodiments, the entire implant is 3D printed with a textured or porous surface, optionally, with the exception of the exterior surfaces of the peripheral ring which contains the anterior plate, the posterior plate and the outer wall(s).

Figure 16A:
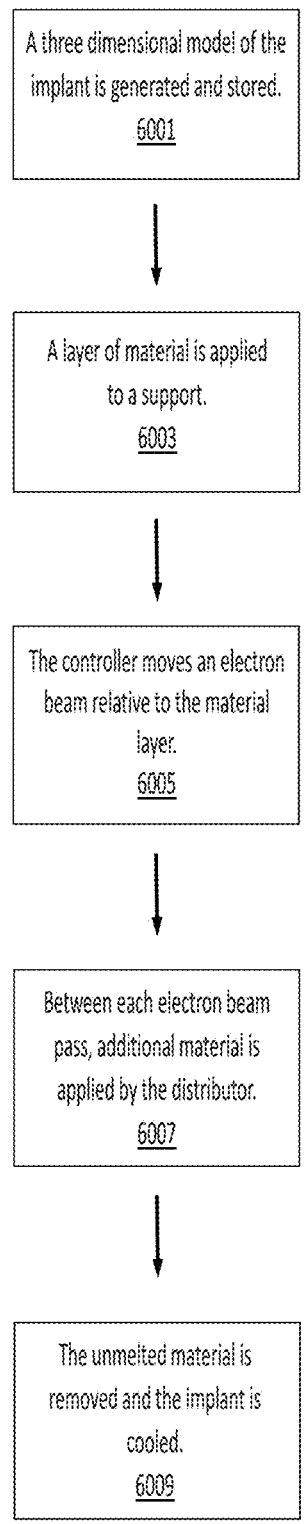
FIGS. 16A and 16B are two flowcharts of exemplary methods for making an implant, such as implant 1000, via 3-D printing technology.
Figure 16B:
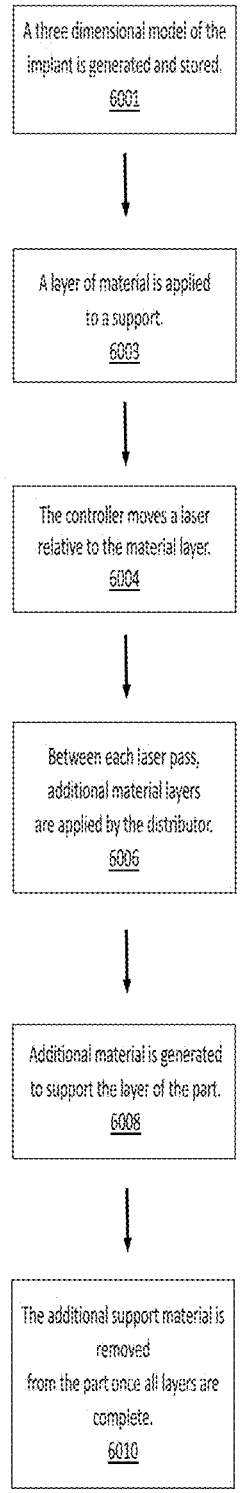

Optionally, the entire implant may be formed via 3-Dimensional printing, such as direct metal laser sintering (DMLS) or electron beam melting (EBM). Exemplary flowcharts of typical 3-D printing methods using EBM and DMLS are depicted in FIGS. 16A and 16B, respectively. At 6001, a three dimensional model of the implant is generated and stored in a storage medium accessible to a controller operable to control the implant production process. At 6003, a layer of material (e.g., a powder, liquid, etc.) is applied to a support. In some embodiments, the powder may include a titanium alloy, such as γTiAl (γTitanium Aluminides) or $Ti_6$—$Al_4$—V ELI, which may be a high strength/low weight material. However, other materials may also be used. The powder may be formed using a gas atomization process. The powder may be delivered to the support through a distributor (e.g., delivered from a storage container). The distributor and/or the support may move during distribution to apply a layer of powder to the support. In some embodiments, the layer may be approximately a uniform thickness (e.g., with an average thickness of 20 to 200 micrometers (μm)). In some embodiments, the distributor and support may not move (e.g., the material may be sprayed onto the support).

As depicted in FIG. 16A, in an EBM method, at 6005, the controller moves an electron beam relative to the material layer. In some embodiments, the electron beam generator may be moved, and in some embodiments the support may be moved. If the material is γTiAl, a melting temperature approximately in a range of 1200 to 1800° C. (e.g., 1500° C.) may be obtained between the electron beam and the material. At 6007, between each electron beam pass, additional material is applied by the distributor. At 6009, the unmelted material is removed and the implant is cooled (e.g., using a cool inert gas).

Alternatively, in a DMLS method, such as depicted in FIG. 16B, at 6004, the controller moves a laser relative to the material layer (FIG. 16B). At 6006, additional material layers are applied by the distributor between each laser pass. At 6008, additional material is generated to support the layer of the part. At 6010, the additional support material is removed from the part once all layers are complete. In some embodiments, the edges of the implant may be smoothed to remove rough edges. In some embodiments, the implant may include rough edges to increase friction between the implant and the surrounding bone to increase adhesion of the implant to the bone.

The implant may be customized for a particular patient or site within a patient. For example, three-dimensional measurements and/or shape of the implant may be used to construct one or more implants using 3-D printing techniques. As noted in FIG. 16A, the three-dimensional shape design of the implant may be entered into a computer system/controller that may control the electron beam melting process. In some embodiments, coil design and relative locations of the coils within other coils in the implant may be preset or predetermined by the computer system/controller. In some embodiments, a user may select the design to use. In some embodiments, the user may enter the outer dimensions of the three-dimensional shape and the computer system/controller may generate a three-dimensional implant that meets the space and site requirements.

In some embodiments, a computer system may include a memory medium(s) on which one or more computer programs or software components may be stored. For example, the memory medium may store one or more programs that are executable to perform the methods described herein. The memory medium may also store operating system software, as well as other software for operation of the computer system. The term "memory medium" encompasses two or more memory mediums that reside in different locations, e.g., in different computers that are connected over a network.

D. Uses

1. Spine

The implant can be configured for use as a spacer in any part of the spine, such as the thoracic, cervical, or lumbar regions of the spine. For example the implant can be configured to be used in a variety of spine surgeries, including but not limited to Anterior Cervical Discectomy Fusion (ACDF), Anterior Trans Thoracic, Posterolateral Approach Thoracic, Anterior Lumbar Interbody Fusion (ALIF), Transforaminal Lumbar Interbody Fusion (also called Oblique) (TLIF), Posterior Lumbar Interbody Fusion (PLIF), and Lateral Lumbar Interbody Fusion (also referred to as XLIF, eXtreme Lateral Interbody Fusion) (LLIF). In some preferred embodiments, the implant is an ALIF device.

Standard procedures that are typically used in spine surgeries can be followed with the implants described herein. Some of the typical steps are described below.

i. Preparation of Discs and Endplates

The discs are often prepared by the removal of the disc until only the anterior and lateral annuli remain. Scrapers, rasps, curettes, etc., may be used to assist in the removal of the nucleus pulpous and the superficial layer of the cartilaginous endplates. The superficial layers of the cartilaginous endplates may be removed to expose bleeding bone.

Adequate preparation of the endplates facilitates vascular supply to the bone graft.

ii. Distraction

Distraction blades suitable for use in spine surgeries include distractors available for posterior lumbar interbody fusion (PLIF) surgeries. Other distractors include distractors for minimally invasive spinal procedures that are used to distract the disc space. Commercially available suppliers of distractors include TeDan Surgical Innovations and Synthes Holding AG.

When distraction is needed, the distractor blades are inserted into the disc space until the blades rest in the vertebral body. Fluoroscopy may be used to confirm that the distractor blades are parallel to the endplates. Distractor blades are angled cranially when properly placed. The disc space is then distracted.

iii. Determination of Implant Size

A trial spacer may be inserted into the intervertebral space to select a correctly fitting implant. Fluoroscopy and tactile judgment may assist in confirming the fit of the trial spacer. If the trial spacer appears too loose or too tight, an alternatively sized and/or shaped implant should be tried until a secure fit is achieved. An implant corresponding to the correct trial spacer is then selected. The trial spacer assembly is removed. A slap hammer may be used to assist with removal.

iv. Packing Autologous Bone Graft

Optionally, the implant may be prefilled with a bone graft or bone graft substitute. The autologous bone graft, or bone graft substitute, may be packed within the opening(s) of the implant using a graft loading block.

Alternatively, bone graft, bone graft substitute, or one or more precursor materials for forming a bone graft substitute, may be delivered to the opening(s) in the implant, or a portion of the opening(s) after insertion of the implant.

v. Insertion of the Implant

An appropriately sized implant is inserted into the intervertebral space. Typically, the implant is attached to an insertion tool. For example, the implant may be threaded onto a threaded rod of an insertion handle. The implant and the tool are then oriented as needed and introduced into the prepared intervertebral space. In some embodiments, the implant is rotated until it reaches the desired site. If required, light impaction is used to seat the implant properly into the disc space. Once the implant is in the desired position, the insertion rod is unthreaded.

In some embodiments, a second implant of the same profile, length, width, and height (or of a different size) is inserted into the available disc space. Gentle impaction may be used as before.

vi. Supplemental Fixation

These implants may be used with a supplemental fixation system. For example, the fixation systems may contain one or more polyaxial screws and/or lateral connections.

2. Other Parts of the Body

The implants described herein can be configured for placement in a variety of locations in the body, including but not limited to in a large joint (e.g., a hip and/or knee implant), a small joint (e.g., shoulder, elbow and/or ankle implants), at a site of trauma (e.g., shoulder fracture, long bone reconstruction implants and/or intermedullary rod implants), craniomaxillofacial (e.g., implant for use in jaw replacement), or in the mouth (e.g. dental implants). Typical dimensions generally correspond with current implants used in these sites.

The implants described herein may be configured for use in repairing a bone fracture or may be inserted into a bone void.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An implant comprising a plurality of coils and an open space between and/or inside the plurality of coils;
    wherein the implant includes a superior outer surface, the superior outer surface formed by at least a portion of the plurality of coils; and
    wherein the plurality of coils have a substantially circular cross-sectional shape;
    wherein the plurality of coils include a plurality of flattened surfaces; and
    wherein the plurality of flattened surfaces collectively form at least a portion of the superior outer surface of the implant.

2. The implant of claim 1, wherein at least two of the plurality of coils intersect with each other at one or more intersection regions.

3. The implant of claim 2, wherein the intersection regions are at regular intervals along the length of two or more adjacent coils.

4. The implant of claim 2, wherein the implant further comprises an inferior outer surface and one or more outer side walls; and
    wherein the one or more intersection regions are located inside the outer surfaces of the implant.

5. The implant of claim 2, wherein the implant further comprises an inferior outer surface and one or more outer side walls; and
    wherein the one or more intersection regions connect with the one or more outer side walls.

6. The implant of claim 1, further comprising a side wall defining the outside perimeter of the implant.

7. The implant of claim 6, wherein the side wall has a smooth outer surface and is in the form of a peripheral ring.

8. The implant of claim 6, further comprising a central support portion that connects with the side wall.

9. The implant of claim 6, wherein the implant further includes an anterior plate attached to the side wall; and
    wherein the anterior plate is non-textured and non-porous.

10. The implant of claim 6, wherein the implant further includes a posterior plate attached to the side wall; and
    wherein the posterior plate is non-textured and non-porous.

11. The implant of claim 1, further comprising a central support portion that connects with one or more portions of the plurality coils.

12. The implant of claim 1, wherein the implant is symmetric about a transverse plane; and
    wherein the implant comprises at least two levels, wherein when the implant is divided about the transverse plane, at least a first level is located in the superior half and at least a second level is located in the inferior half; and
    wherein each level comprises at least two exterior coils and at least two interior coils.

13. The implant of claim 1, further comprising a central support portion; and wherein the central support portion comprises a base that lies in a median plane and connects at a first end with the anterior end of the implant and at a second end with the posterior end of the implant.

14. The implant of claim 13, wherein the central support portion further comprises one or more support rings, wherein the support rings intersect with the base at one or more connection ends.

15. The implant of claim 1, further including an additional coil;
wherein the shape of the additional coil is different than the shape of the plurality of coils.

16. The implant of claim 1, wherein the diameter of at least one of the plurality of coils varies within the coil.

17. The implant of claim 1, wherein a largest dimension of the cross section of at least one of the plurality of coils is different than the largest dimension of the cross section of at least another coil of the plurality of coils.

18. The implant of claim 1, wherein the open space is configured to allow bone growth inside the implant.

19. The implant of claim 1, wherein one or more surfaces of the implant include a texture.

20. The implant of claim 1, wherein one or more surfaces of the implant are porous.

21. The implant of claim 1, wherein the diameter of at least one of the plurality of coils is different than the diameter of at least another of the plurality of coils.

22. The implant of claim 1, wherein the implant contains a plurality of levels of coils or sets of coils, wherein each level contains two or more coils or sets of coils.

23. The implant of claim 1, further comprising one or more plates, wherein the one or more plates are integral with the side walls.

24. The implant of claim 1 in the form of an interbody fusion spacer.

25. The implant of claim 1, wherein volume of the open space comprises at least 40% of the total volume of the implant.

26. The implant of claim 1, wherein the substantially circular cross-sectional shape of the plurality of coils is spaced from the superior outer surface; and
wherein the plurality of coils transitions from the substantially circular cross-sectional shape to the plurality of flattened surfaces proximate the superior outer surface.

27. The implant of claim 1, further comprising at least one of an anterior plate and a posterior plate; and
wherein at least one coil of the plurality of coils includes an end that connects to at least one of the anterior plate and the posterior plate.

28. The implant of claim 27, wherein the at least one coil is integrally formed together with at least one of the anterior plate and the posterior plate.

29. An implant comprising a plurality of coils and an open space between and/or inside the plurality of coils;
wherein the implant includes an inferior outer surface, the inferior outer surface formed by at least a portion of the plurality of coils; and
wherein the plurality of coils have a substantially circular cross-sectional shape;
wherein the plurality of coils include a plurality of flattened surfaces; and
wherein the plurality of flattened surfaces collectively form at least a portion of the inferior outer surface of the implant.

30. The implant of claim 29, wherein the substantially circular cross-sectional shape of the plurality of coils is spaced from the inferior outer surface; and
wherein the plurality of coils transitions from the substantially circular cross-sectional shape to the plurality of flattened surfaces proximate the superior outer surface.

31. The implant of claim 29, further comprising at least one of an anterior plate and a posterior plate; and
wherein at least one coil of the plurality of coils includes an end that connects to at least one of the anterior plate and the posterior plate.

32. The implant of claim 31, wherein the at least one coil is integrally formed together with at least one of the anterior plate and the posterior plate.

33. An implant comprising:
a plurality of coils;
an open space between and/or inside the plurality of coils; and
at least one of an anterior plate and a posterior plate; and
wherein at least one coil of the plurality of coils includes an end that connects to at least one of the anterior plate and the posterior plate;
wherein the plurality of coils have a substantially circular cross-sectional shape;
wherein the plurality of coils include a plurality of flattened surfaces; and
wherein the plurality of flattened surfaces collectively form at least a portion of the outer surface of the implant.

34. The implant of claim 33, wherein the at least one coil is integrally formed together with at least one of the anterior plate and the posterior plate.

35. The implant of claim 33, wherein the outer surface is a superior outer surface or an inferior outer surface of the implant.

* * * * *